US012595275B2

(12) United States Patent
Duan et al.

(10) Patent No.: US 12,595,275 B2
(45) Date of Patent: Apr. 7, 2026

(54) FLUORINE-CONTAINING COMPOUND AND ANTI-CANCER MEDICAL USE THEREOF

(71) Applicant: ASCENTAWITS PHARMACEUTICALS, LTD., Shenzhen (CN)

(72) Inventors: Jianxin Duan, Shenzhen (CN); Anrong Li, Shenzhen (CN); Fanying Meng, San Francisco, CA (US); Xiaohong Cai, Shenzhen (CN)

(73) Assignee: ASCENTAWITS PHARMACEUTICALS, LTD., Shenzhen (CN)

( * ) Notice: Subject to any disclaimer, the term of this patent is extended or adjusted under 35 U.S.C. 154(b) by 963 days.

(21) Appl. No.: 17/606,476

(22) PCT Filed: May 12, 2020

(86) PCT No.: PCT/CN2020/089692
§ 371 (c)(1),
(2) Date: Oct. 26, 2021

(87) PCT Pub. No.: WO2020/228685
PCT Pub. Date: Nov. 19, 2020

(65) Prior Publication Data

US 2022/0119429 A1 Apr. 21, 2022

(30) Foreign Application Priority Data

May 13, 2019 (CN) ......................... 201910392606.7
Dec. 20, 2019 (CN) ......................... 201911324466.6

(51) Int. Cl.
*C07F 9/6558* (2006.01)
*A61K 31/664* (2006.01)
*A61P 35/00* (2006.01)
*C07F 9/564* (2006.01)

(52) U.S. Cl.
CPC ........ *C07F 9/65583* (2013.01); *A61K 31/664* (2013.01); *A61P 35/00* (2018.01); *C07F 9/564* (2013.01)

(58) Field of Classification Search
CPC ...... C07F 9/65583; C07F 9/564; A61P 35/00; A61K 31/664
See application file for complete search history.

(56) References Cited

U.S. PATENT DOCUMENTS 10,364,261 B2 * 7/2019 Duan ...................... C07F 9/564

FOREIGN PATENT DOCUMENTS

| | | |
|---|---|---|
| CA | 2979251 | 9/2016 |
| CN | 1706845 A | 12/2005 |
| CN | 107530556 A | 1/2018 |
| CN | 108290911 A | 7/2018 |
| EA | 6852 | 4/2003 |
| JP | 2018513876 | 5/2018 |
| JP | 2018517710 | 7/2018 |
| JP | 2018527301 | 9/2018 |
| JP | 2018511612 | 11/2019 |
| RU | 2414475 | 8/2006 |

(Continued)

OTHER PUBLICATIONS

Williams, E.M., Little, R.F., Mowday, A.M., Rich, M.H., Chan-Hyams, J.V., Copp, J.N., Smaill, J.B., Patterson, A.V. and Ackerley, D.F., 2015. Nitroreductase gene-directed enzyme prodrug therapy: insights and advances toward clinical utility. Biochemical journal , 471(2), pp. 131-153 (Year: 2015).*

(Continued)

*Primary Examiner* — James H Alstrum-Acevedo
*Assistant Examiner* — Carolyn L. Ladd
(74) *Attorney, Agent, or Firm* — Ballard Spahr LLP

(57) ABSTRACT

Described is a fluorine-containing compound shown in Formula II/III and its anti-cancer medical use. The present application creatively introduced the fluorine-containing groups such as special trifluoromethyl groups, fluorine-substituted aryl groups, or heteroaryl groups at special positions (such as the position between the nitrobenzene ring and the phosphate amine group) in the structures of the above compounds. After this modification, it was found that all of the resulting compounds were solids (including waxes).

II

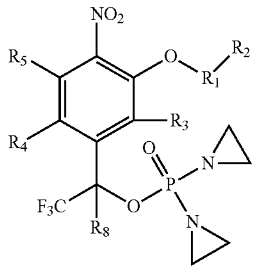

III

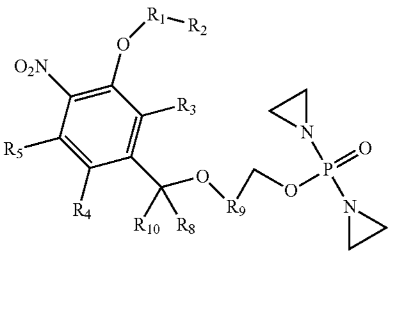

17 Claims, No Drawings

(56) References Cited

FOREIGN PATENT DOCUMENTS

| | | | | | |
|---|---|---|---|---|---|
| WO | WO-2010044686 | A1 * | 4/2010 | ............ | A61K 31/00 |
| WO | WO 2016/145092 | A1 | 3/2016 | | |
| WO | WO 2016145092 | | 9/2016 | | |
| WO | WO-2016210175 | A1 * | 12/2016 | .......... | A61K 31/396 |
| WO | WO 2017/087428 | A1 | 5/2017 | | |
| WO | WO 2017087428 | | 5/2017 | | |
| WO | WO 2019/062919 | A1 | 9/2018 | | |

OTHER PUBLICATIONS

Harbeson, S.L. and Tung, R.D., 2011. Deuterium in drug discovery and development. In Annual reports in medicinal chemistry (vol. 46, pp. 403-417). Academic Press (Year: 2011).*

Purser, S., Moore, P.R., Swallow, S. and Gouverneur, V., 2008. Fluorine in medicinal chemistry. Chemical Society Reviews, 37(2), pp. 320-330. (Year: 2007).*

Sorgi, K.L (2001). Diisopropylethylamine. In Encyclopedia of Reagents for Organic Synthesis (Year: 2001).*

Parker, K.A., Su, D.-S., Demchenko, A.V., Pelphrey, P.M., Wright, D.L. and Ladd, C.L. (2015). Silver(I) Oxide. In Encyclopedia of Reagents for Organic Synthesis (Year: 2015).*

Berge, S.M., Bighley, L.D. and Monkhouse, D.C., 1977. Pharmaceutical salts. Journal of pharmaceutical sciences, 66(1), pp. 1-19 ( Year: 1977).*

Dyck, L.E., Burden, D.A. and Boulton, A.A., 1986. Effects of Deuterium Substitution on the Catabolism of Î²âPhenylethylamine: An In Vivo Study. Journal of neurochemistry, 46(2), pp. 399-404 (Year: 1986).*

Gupta, D., Bhatia, D., Dave, V., Sutariya, V. and Varghese Gupta, S., 2018. Salts of therapeutic agents: chemical, physicochemical, and biological considerations. Molecules, 23(7), p. 1719 (Year: 2018).*

Brown, Dean G., and Jonas Bostrom. "Analysis of past and present synthetic methodologies on medicinal chemistry: where have all the new reactions gone? Miniperspective." Journal of medicinal chemistry 59, No. 10 (2016): 4443-4458. (Year: 2015).*

Hanahan, Douglas, and Robert A. Weinberg. "The Hallmarks of Cancer." Cell 100, No. 1 (2000): 57-70 (Year: 2000).*

Chang, T et al. "Expression of aldo-keto reductase family 1 member C3 (AKR1C3) in neuroendocrine tumors & adenocarcinomas of pancreas, gastrointestinal tract, and lung." International Journal of Clinical and Experimental Pathology 6, No. 11 (2013): 2419 (Year : 2013).*

Zhou, Wen, and Patrizia Limonta. "AKR1C3 inhibition therapy in castration-resistant prostate cancer and breast cancer: lessons from responses to SN33638." Frontiers in Oncology 4 (2014): 162) (Year: 2014).*

Khanim, F. et al."Selective AKR1C3 inhibitors do not recapitulate the anti-leukaemic activities of the pan-AKR1C inhibitor medroxyprogesterone acetate." British journal of cancer 110, No. 6 (2014): 1506-1516 (Year: 2014).*

Penning, Trevor M. "Aldo-Keto Reductase (AKR) 1C3 inhibitors: a patent review." Expert opinion on therapeutic patents 27, No. 12 (2017): 1329-1340) (Year: 2017).*

Hsaio, Y. Y., "Synthesis of New Bis(1-aziridinyl) phosphinate alkylating agents containing O-Phenyl N-Phenylcarbamate side chains", Journal of Medicinal Chemistry, 1973, 16, pp. 391-394.

International Search Report and Written Opinion mailed on Aug. 12, 2020 for Patent Application No. PCT/CN2020/089692 which was filed on May 12, 2020 and published as WO2020/228685A9 on Feb. 18, 2021 (Applicant—Ascentawits Pharmaceuticals, Ltd.) (11 pages).

* cited by examiner

FLUORINE-CONTAINING COMPOUND AND ANTI-CANCER MEDICAL USE THEREOF

CROSS-REFERENCE TO RELATED APPLICATIONS

This application is a U.S. National Phase Application of International Application No. PCT/CN2020/089692, filed May 12, 2020, which claims priority to Chinese Application No. 201910392606.7, filed May 13, 2019, and Chinese Application No. 201911324466.6, filed Dec. 20, 2019, each of which are hereby incorporated by reference in their entirety.

TECHNICAL FIELD

The present invention, belonging to the field of research and development of anticancer compounds, relates to a series of AKR1C3 enzyme-activated DNA alkylating agents obtained by further research and development of the compounds disclosed in Patent Application No. PCT/US2016/021581 (Publication No. WO2016145092A1), which corresponds to Chinese Patent Application No. 2016800150788 (Publication No. CN107530556A).

BACKGROUND ART

Chinese Invention Patent Application CN201910392606.7 entitled Fluorine-containing Compound and Anticancer Medical Use Thereof filed by the applicant on May 13, 2019, and Chinese Invention Patent Application CN201911324466.6 entitled Fluorine-containing Compound and Anticancer Medical Use Thereof filed by the applicant on Dec. 20, 2019 are incorporated herein by reference.

All the compounds in the DNA alkylating anticancer drugs targeting overexpressed aldo-keto reductase 1C3 (AKR1C3) (DNA alkylating agents in Patent Application No. PCT/US2016/021581 (Publication No. WO2016/145092), which corresponds to Chinese Patent Application No. CN2016800150788 (Publication No. CN107530556A)) developed by our company are yellow oils. Since these compounds are not solid, there are the following difficulties in the subsequent research and development of the formulation.

Separation and purification are complicated and costly. As oils, these compounds cannot be purified by high-efficiency/low-cost recrystallization or slurry purification, and can only be purified by column chromatography. This results in complex operation, and thus leads to high costs for the preparation of active pharmaceutical ingredients.

The formulation is inconvenient and has poor stability. Oils cannot be conveniently transported/metered. Importantly, oils make it impossible or inconvenient to develop and diversify the dosage form of the formulation. Generally, it can only be developed as lyophilized powder for injection or an injection solution for administration, with the administration method being less diversified and costly. In addition, some patients are not highly compliant with injection of lyophilized powder or an injection solution.

SUMMARY OF THE INVENTION

In order to solve the aforementioned technical problems, the present invention designs and synthesizes a series of fluorine-containing compounds by structurally modifying the compounds as disclosed in Patent Application No. PCT/US2016/021581 (Publication No. WO2016/145092), which corresponds to Chinese Patent Application No. CN2016800150788 (Publication No. CN107530556A) entitled “DNA Alkylating Agents”.

Accordingly, the aforementioned Patent Application No. PCT/US2016/021581 (Publication No. WO2016/145092), which corresponds to Chinese Patent Application No. CN2016800150788 (Publication No. CN107530556A), is incorporated herein by reference. Where any definition or concept provided herein is different from the definition or concept provided by the aforementioned application documents, the definition or concept provided herein shall prevail. Where any concept or definition provided herein is not clearly defined or limited, it shall be defined in accordance with the aforementioned application documents. Other concepts or definitions which are clearly defined or limited neither herein nor in the aforementioned application documents shall be interpretated in accordance with, among others, textbooks and handbooks of organic chemistry and medicinal chemistry.

It has been proven that the compounds 3424 disclosed in the patent applications PCT/US2016/021581, PCT/US2016/025665 and PCT/US2016/062114, as internationally original, small molecule targeted therapeutic drugs with high tumor selectivity, have shown excellent anticancer effects in various preclinical cells and animal models. These compounds, as specific substrates of the aldo-keto reductase AKR1C3, can be quickly and effectively reduced only in cancer cells which overexpress AKR1C3, thereby releasing cytotoxins to result in highly selective cancer cell killing effects.

As demonstrated by the documents (including, Document 1: Richard B. Lock, Kathryn Evans, Raymond Yung, Tara Pritchard, Beverly A. Teicher, JianXin Duan, Yuelong Guo, Stephen W. Erickson, Malcolm A. Smith. The AKR1C3-Activated Prodrug OBI-3424 Exerts Profound In Vivo Efficacy Against Preclinical Models of T-Cell Acute Lymphoblastic Leukemia(T-ALL); a Pediatric Preclinical Testing Consortiu LCM Study [abstract]. In: Proceedings of the AACR-NCI-EORTC International Conference: Molecular Targets and Cancer Therapeutics; 2017 Oct. 26-30; Philadelphia, PA. Philadelphia (PA): AACR; Mol Cancer Ther 2018; 17 (1Suppl): Abstractnr LB-B16; Document 2: Evans K, Duan J, Pritchard T, Jones C D, McDermott L, Gu Z, Toscan C E, El-Zein N, Mayoh C, Erickson S W, Guo Y, Meng F, Jung D, Rathi K S, Roberts K G, Mullighan C G, Shia C S, Pearce T, Teicher B A, Smith M A, Lock R B. OBI-3424, a novel AKR1C3-activated prodrug, exhibits potent efficacy against preclinical models of T-ALL. Clin Cancer Res. 2019 Apr. 23. pii:clin canres.0551.2019.doi: 10.1158/1078-0432.CCR-19-0551), compound AST-3424 (OBI-3424) (i.e., the S-isomer of compound 2870) has shown good effects on cancers such as leukemia and lung cancer in phase I clinical trials.

Since all the compounds of this series are oils which have lots of shortcomings as they cannot be conveniently stored, transported, or metered, it is necessary to develop similar compounds that are solid at room temperature.

The research group had thought of using such a solution: converting the oils into solid salts by salt formation. Nevertheless, it was found through experiments that the salt formation reaction between inorganic acids such as sulfuric acid/hydrochloric acid and a nitrogen-containing three-membered ring cannot lead to a desired salt: the experiments demonstrated that under acidic conditions, the nitrogen-containing three-membered ring of the compounds disclosed in aforementioned CN107530556A would open to form ring-opened by-products. Numerous experimental trials indicated that the aforementioned conventional methods are not feasible.

According to experiences and experimental results, the research group creatively introduced the fluorine-containing groups such as special trifluoromethyl groups, fluorine-substituted aryl groups, or heteroaryl groups at special positions (such as the position between the nitrobenzene ring and the phosphate amine group) in the structures of the above compounds. After this modification, it was found that all of the resulting compounds were solids (including solids and waxes).

Further in vitro experiments show that these compounds have strong activity of inhibiting proliferation of cancer cells in vitro. Moreover, the combination of the compounds and the AKR1C3 inhibitor TH3021 is found to have decreased inhibitory activity. This demonstrates that introducing a specific fluorine-containing group at a specific position can not only make the compound a solid to facilitate preparation of formulations and facilitate metering and storage, but can still obtain AKR1C3 enzyme-activated DNA alkylating agents.

There is provided a compound of formula I, II or III or a pharmaceutically acceptable salt, or a solvate thereof,

II

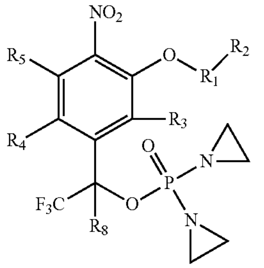

III

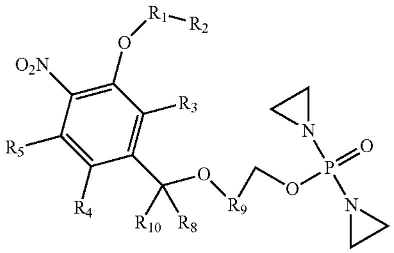

wherein $R_1$ is $C_6$-$C_{10}$ aryl or Z-substituted aryl, 4-15 membered heterocycle or Z-substituted heterocycle, 5-15 membered heteroaryl or Z-substituted heteroaryl, or a 7-15 membered fused ring or Z-substituted fused ring;

$R_2$ is hydrogen, a halogen atom, cyano or isocyano, hydroxy, sulfhydryl, amino, OTs, OLCMS, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered heterocycle or Z-substituted heterocycle, 5-15 membered heteroaryl or Z-substituted heteroaryl, ether having from 1 to 6 carbon atoms or Z-substituted alkoxy having from 1 to 6 carbon atoms, —$CONR^6R^7$, —$SO_2NR^6R^7$, —$SO_2R^6$, —OCOO—$R^6$, —$COOR^6$, —$NR^6COR^7$, —$OCOR^6$, —$NR^6SO_2R^7$ or —$NR^6SO_2NR^6R^7$, or $R^2$ together with the atom in the group $R_1$ to which it is bonded to form a 7-15 membered fused ring or Z-substituted fused ring;

$R_3$ is hydrogen, halogen, cyano or isocyano, hydroxy, sulfhydryl, amino, OTs, OLCMS, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered heterocycle or Z-substituted heterocycle, 5-15 membered heteroaryl or Z-substituted heteroaryl, $C_1$-$C_6$ alkoxy or Z-substituted $C_1$-$C_6$ alkoxy, —$CONR^6R^7$, —$SO_2NR^6R^7$, —$SO_2R^6$, —OCO—$R^6$, —OCOO—$R^6$, —$COOR^6$, —$NR^6COR^7$, —$OCOR^6$, or —$NR^6SO_2R^7$;

$R_4$ and $R_5$ are each independently hydrogen, a halogen atom, cyano or isocyano, hydroxy, sulfhydryl, amino, OTs, OLCMS, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered heterocycle or Z-substituted heterocycle, 5-15 membered heteroaryl or Z-substituted heteroaryl, $C_1$-$C_6$ alkoxy or Z-substituted $C_1$-$C_6$ alkoxy, —$CONR^6R^7$, —$SO_2NR^6R^7$, —$SO_2R^6$, —OCOO—$R^6$, —$COOR^6$, —$NR^6COR^6$, —$OCOR^6$ or —$NR^6SO_2R^7$, or $R_4$ and $R_5$ together with the atom in the benzene ring to which they are bonded to form a 7-15 membered fused ring or Z-substituted fused ring;

$R^6$ and $R^7$ are each independently hydrogen, cyano or isocyano, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered heterocycle or Z-substituted heterocycle, 5-15 membered heteroaryl or Z-substituted heteroaryl, or $C_1$-$C_6$ alkoxy or Z-substituted $C_1$-$C_6$ alkoxy, or $R^6$ and $R^7$ together with the atom to which they are bonded to form 5-7 membered heterocyclyl or Z-substituted 5-7 membered heterocyclyl;

$R_8$ and $R_{10}$ are each independently hydrogen, deuterium, aryl or Z-substituted aryl, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, and at least one of $R_8$ and $R_{10}$ must be hydrogen or deuterium;

$R_9$ is substituted $C_6$-$C_{10}$ aryl which is substituted with at least one fluorine atom or nitro group, substituted 4-15 membered heterocycle which is substituted with at least one fluorine atom or nitro group, or substituted 5-15 membered heteroaryl which is substituted with at least one fluorine atom or nitro group;

the substituent Z is a halogen atom, cyano or isocyano, hydroxy, sulfhydryl, amino, OTs, OLCMS, $C_1$-$C_3$ alkyl or substituted alkyl, $C_1$-$C_3$ alkoxy or substituted alkoxy, $C_2$-$C_3$ alkenyl or substituted alkenyl, $C_2$-$C_3$ alkynyl or substituted alkynyl, $C_3$-$C_8$ cycloalkyl or substituted cycloalkyl, an aromatic ring, heterocycle, a heteroaromatic ring and fused ring or a substituted aromatic ring, heterocycle, or a heteroaromatic ring and fused ring, the pattern of substitution being mono- or di-substitution;

the substitution in the substituted $C_6$-$C_{10}$ aryl, substituted 4-15 membered heterocycle or substituted 5-15 membered heteroaryl in $R_9$ is a halogen atom, nitro, cyano or isocyano, hydroxy, amino, $C_1$-$C_3$ alkyl or alkoxy, alkenyl, alkynyl, cycloalkyl or benzene ring, substituted benzene ring, $C_1$-$C_3$ alkoxy or halogen atom-substituted alkoxy.

The substitution has a broad meaning. It can be mono-substitution (only one H on a C atom in a benzene ring and the like can be substituted), or multi-substitution, which include multiple substitutions on a certain C atom, i.e., di-substitution and tri-substitution (such as gem-difluoromethyl and gem-trifluoromethyl) or separate substitution on different C atoms in a ring (such as perfluorobenzene).

Heterocycle and heteroaryl include three-membered rings, four-membered rings, five-membered rings, six-membered rings, and seven-membered rings. The examples are given below.

The three-membered rings include ethylene oxide, azirane and ethylene sulfide;

the four-membered rings include azetidine, oxaetidine, thiaetidine and etidine;

the five-membered rings include pyrrolidine, pyrroline, 1-pyrroline, 3-pyrroline, 2-pyrroline, pyrrole, pyrazolidine, 2-pyrazoline, imidazole, pyrazole, furan, tetrahydrofuran, dihydrofuran, tetrahydrothiophene, thiophene, sulfolane, phosphole, oxazole, 1,2,3-triazole, 1,2,4-triazole, and 1, 3, 4-thiadiazole;

the six-membered rings include piperidine, tetrahydropyran, tetrahydrothiopyran, pyridine, pyran, thiopyran, dihydropyridine, morpholine, piperazine, pyridazine, pyrazine, 1,3,5-triazine and 1,3,5-trithiane;

the seven-membered rings include azepane (azacycloheptane), oxaheptane, thiaheptane, azepine, oxepine, and thiepine.

The fused ring is defined as the fusion of the above heterocycle and heteroaryl or the fusion of the above heterocycle and heteroaryl with a cycloalkane structure. The fusion can be in the form of binding via a single bond or sharing one, two or even three atoms (i.e., spirocyclic, fused, or bridged rings). The following are some common fused ring structures: naphthalene, quinoline, indole, isoindole, isoquinoline, cinnoline, quinoxaline, biphenyl, coumarin, fluorene, diphenylcarran, carbazole, anthracene, acridine, thiophenazine, adamantane, azulene, phenanthrene, anthraquinone, flavonoids, and isoflavones.

Apparently, the above compounds also include compounds substituted with isotope Z. The typical pattern of substitution with Z is that the hydrogen halogen atom H is substituted with the heavy hydrogen atom deuterium (D).

In particular, the position substituted by deuterium is located on Ph-C*— in formulae II and III, as shown in the following formulae:

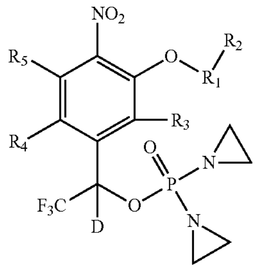

-continued

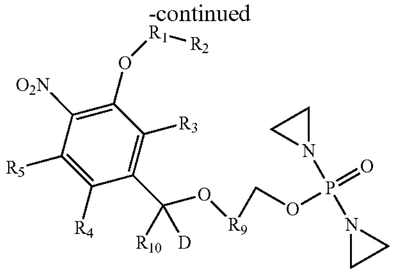

Furthermore, in the compounds provided above, $R_1$ is phenyl or Z-substituted phenyl, six-membered nitrogen-containing heterocycle or Z-substituted heterocycle, six-membered nitrogen-containing heteroaryl or Z-substituted heteroaryl, or 9-14 membered fused ring or Z-substituted fused ring;

$R_2$ is hydrogen, a halogen atom, cyano or isocyano, hydroxy, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered nitrogen-containing heterocycle or Z-substituted nitrogen-containing heterocycle, 5-15 membered nitrogen-containing heteroaryl or substituted nitrogen-containing heteroaryl, $C_1$-$C_6$ alkoxy or fluorine-substituted $C_1$-$C_6$ alkoxy, —$CONR^6R^7$, —$SO_2NR^6R^7$, —$SO_2R^6$, —OCOO—$R^6$, —$COOR^6$, —$NR^6COR^7$, —$OCOR^6$, —$NR^6SO_2R^7$ or —$NR^6SO_2NR^6R^7$;

$R^6$ and $R^7$ are each independently $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered heterocycle or Z-substituted heterocycle, 5-15 membered heteroaryl or Z-substituted heteroaryl, $C_1$-$C_6$ alkoxy or fluorine-substituted $C_1$-$C_6$ alkoxy, or $R^6$ and $R^7$ together with the nitrogen atom to which they are bonded to form a 5-7 membered heterocyclic group or a Z-substituted 5-7 membered heterocyclic group.

Furthermore, in the compounds provided above, $R_1$ is phenyl or Z-substituted phenyl, six-membered nitrogen-containing heterocycle or Z-substituted heterocycle, six-membered nitrogen-containing heteroaryl or Z-substituted heteroaryl, or 9-14 membered fused ring or Z-substituted fused ring;

$R_2$ is hydrogen, a halogen atom, cyano or isocyano, hydroxy, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered nitrogen-containing heterocycle or Z-substituted nitrogen-containing heterocycle, 5-15 membered nitrogen-containing heteroaryl or substituted nitrogen-containing heteroaryl, $C_1$-$C_6$ alkoxy or fluorine-substituted $C_1$-$C_6$ alkoxy, —$CONR^6R^7$, —$SO_2R^6$, —OCOO—$R^6$, —$COOR^6$, —$NR^6COR^6$, —$OCOR^6$, —$NR^6SO_2R^6$, or —$NR^6SO_2NR^6R^7$;

$R^6$ and $R^7$ are each independently $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered heterocycle or Z-substituted heterocycle, 5-15 membered heteroaryl or Z-substituted heteroaryl, $C_1$-$C_6$ alkoxy or fluorine-substituted $C_1$-$C_6$ alkoxy, or $R^6$ and $R^7$ together with the nitrogen atom to which they are bonded to form a 5-7 membered heterocyclic group or a Z-substituted 5-7 membered heterocyclic group.

Further, in the compounds provided above, $R_1$ is phenyl, tetrahydropyran, tetrahydrothiopyran, tetrahydrofuran, pyridine, furan, pyran, thiopyran, thiazole, dihydropyridine, morpholine, piperazine, pyridazine, pyrazine, 1,3,5-triazine, naphthalene, quinine, benzothiazole, benzothiopyran, benzofuran, benzimidazole, indole, imidazopyridine or Z-substituted phenyl, piperidine, tetrahydropyran, tetrahydrothiopyran, tetrahydrofuran, pyridine, furan, pyran, thiopyran, thiazole, dihydropyridine, morpholine, piperazine, pyridazine, pyrazine, 1,3,5-triazine, naphthalene, quinine, benzothiazole, benzothiopyran, benzofuran, benzimidazole, indole or imidazopyridine;

$R_2$ is —$CON(CH_3)_2$, —$SO_2CH_3$, —OCOO—$CH_3$, —$COOCH_3$, —$NHCOCH_3$, —$NMeCOCH_3$, —$NHCOCF_3$, —$OCOCH_3$, —$NHSO_2CH_3$, —$NMeSO_2CH_3$, —$NHSO_2CF_3$, —$NMeSO_2CF_3$, —$CF_3$, F, Cl, Me, benzene, fluorobenzene, chlorobenzene, —$OCF_3$, pyridyl, fluoropyridyl, chloropyridyl, furyl, thiopyran, —CONMePh, C5-C6 cycloalkyl or F-substituted $C_5$-$C_6$ cycloalkyl,

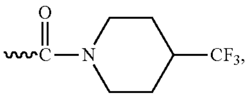,
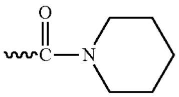,
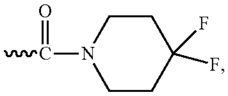,
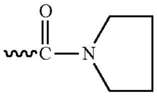,
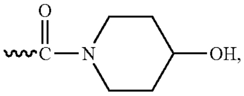,
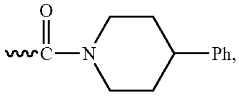,
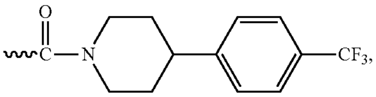,
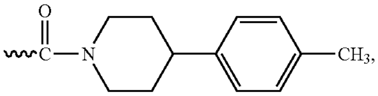,
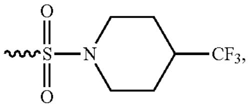,
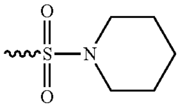,
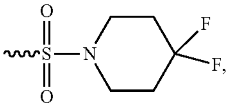,
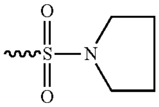,
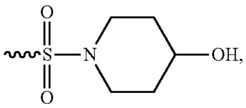,
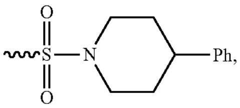,
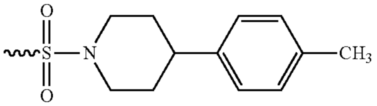 or
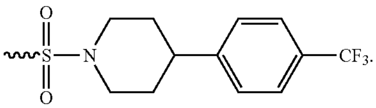.

The above wavy line represents a chemical bond, which on the left connects another atom at a position that can be any atom in the ring where the connected atom is located.

Further, in formula I $R_2$ is H.

Further, $R_3$, $R_4$, and $R_5$ are each independently H.

Further, $R_8$ and $R_{10}$ are each independently H.

Further, $R_9$ is monofluoro, fluorochloro, difluoro or tetrafluoro-substituted phenyl.

Further, $R_9$ is

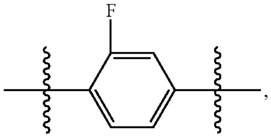,
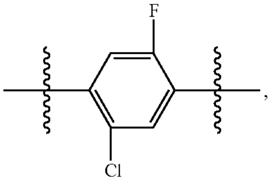,
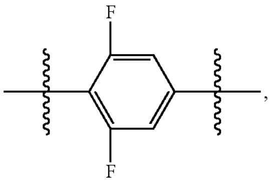, or
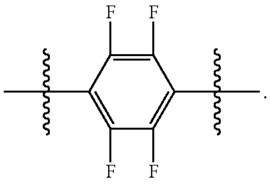.

The solid lines cut off by the above wavy lines represent chemical bonds. One end of the chemical bond connects another atom which is any atom in the ring or connects an atom to form any configuration (EZ or R/S).

Further, the compounds are selected from the following compounds:

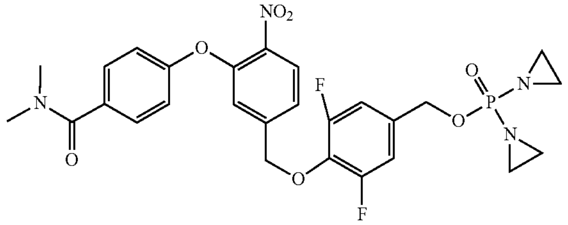

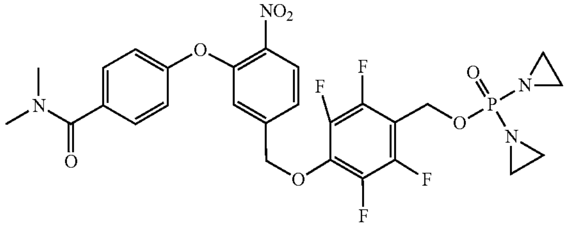

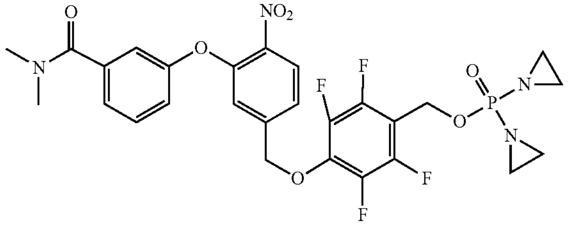

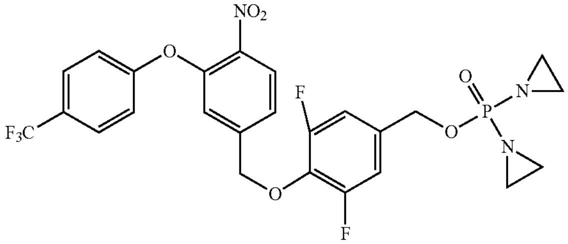

-continued
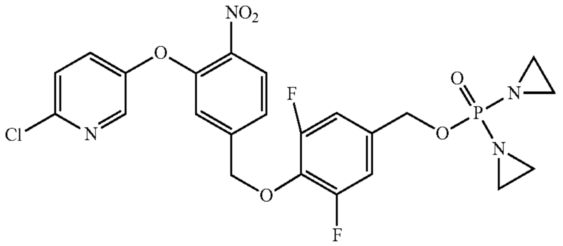
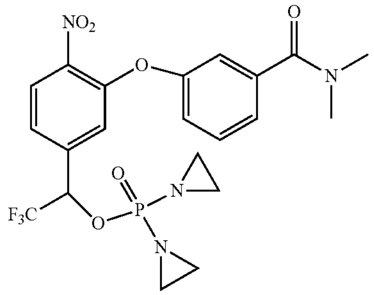
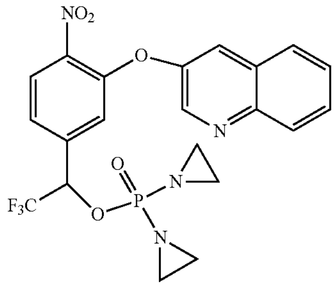
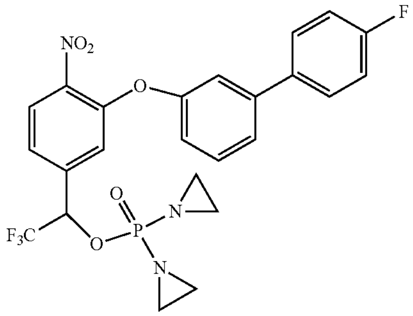
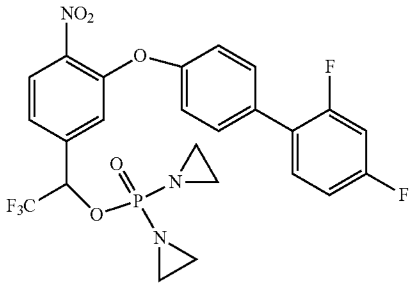
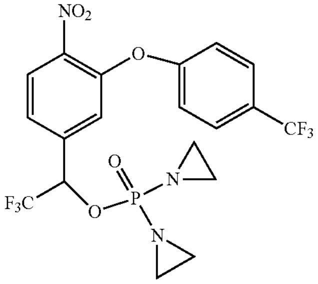
-continued
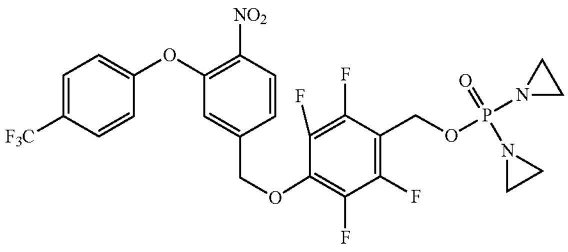
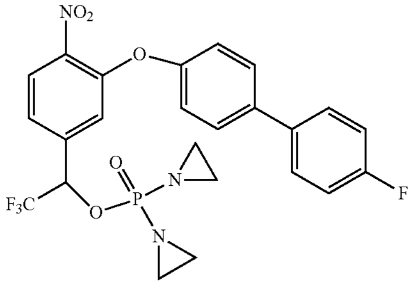
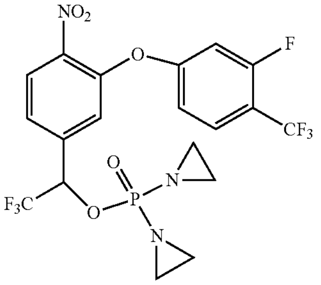
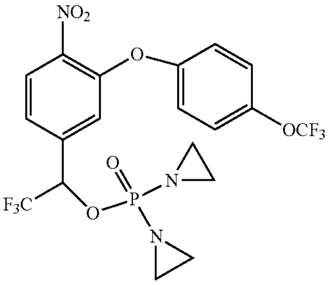
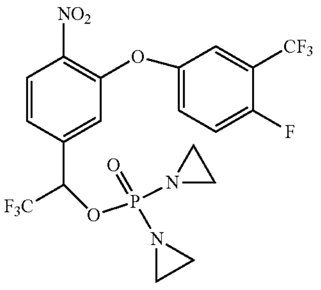
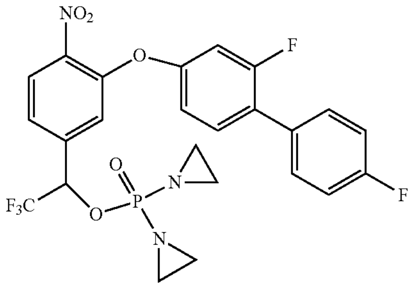

-continued
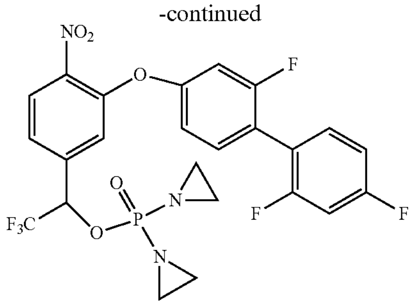
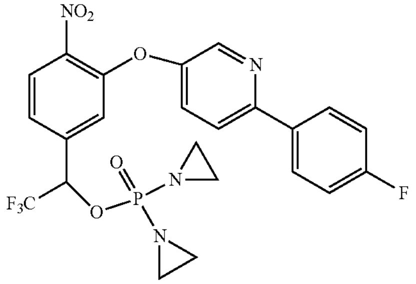
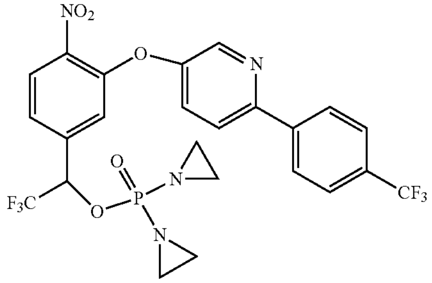
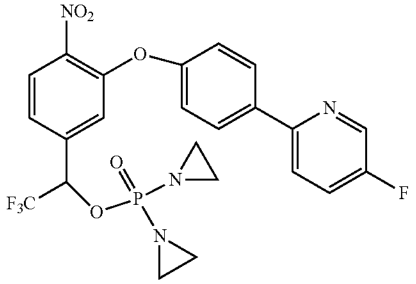
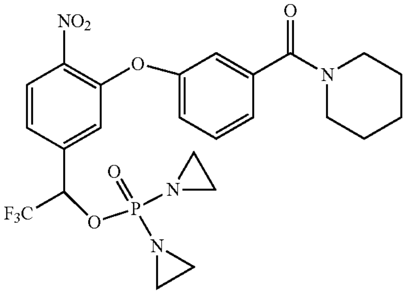
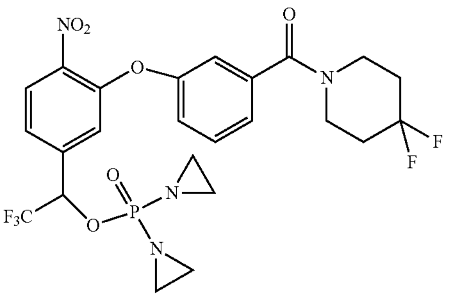
-continued
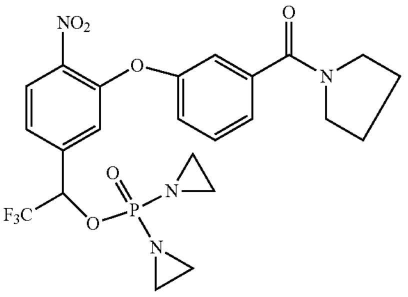
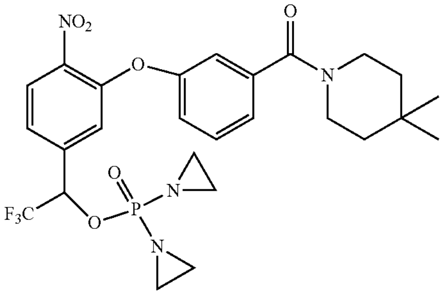
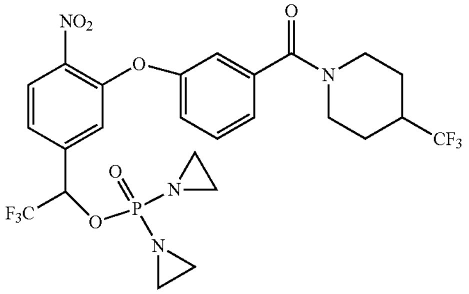
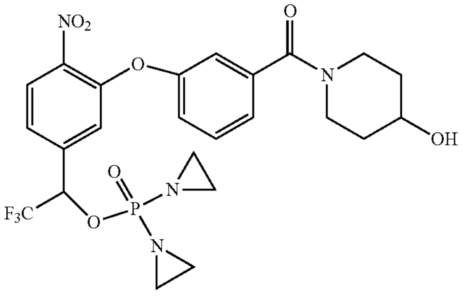
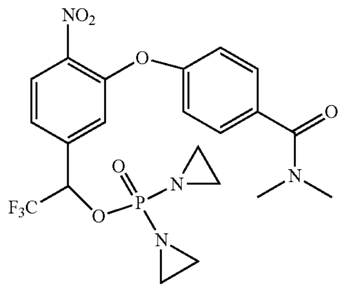

-continued
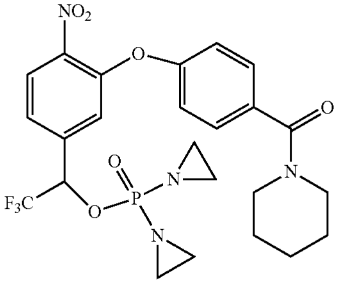
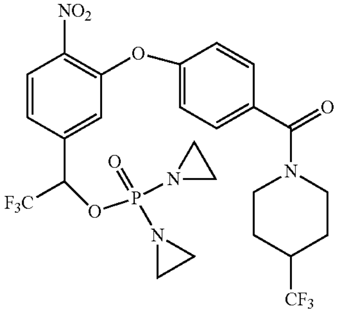
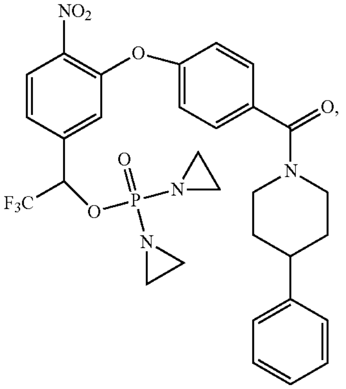
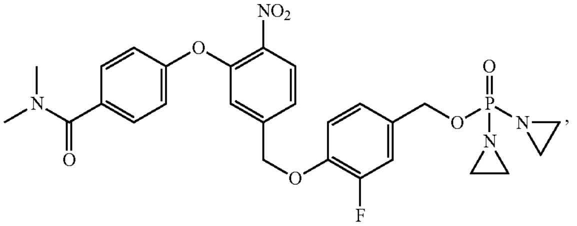
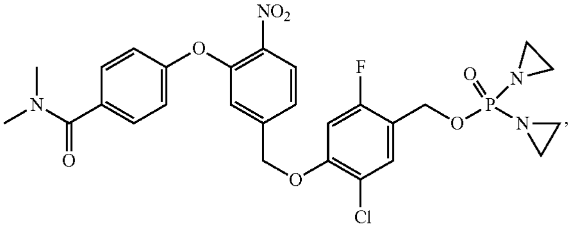
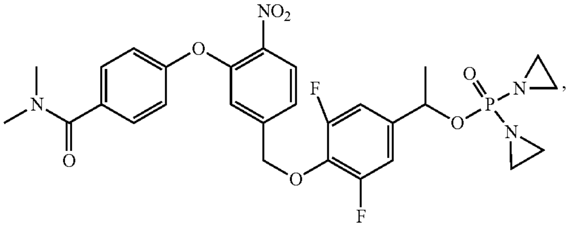
-continued
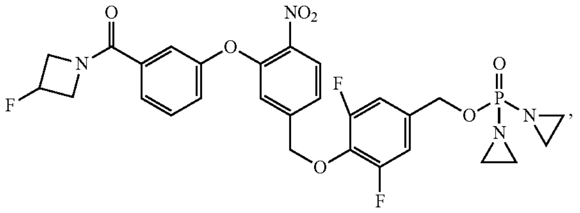
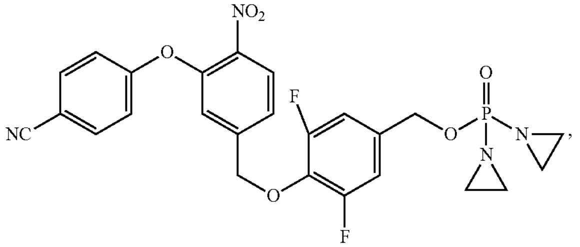
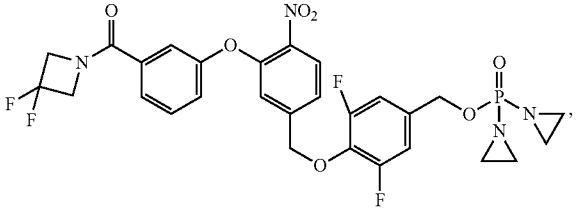
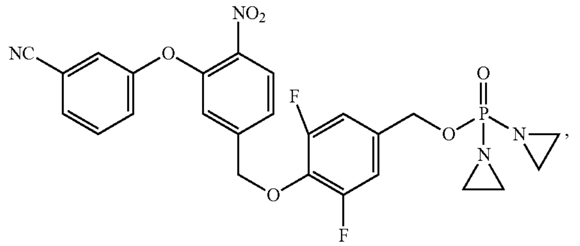
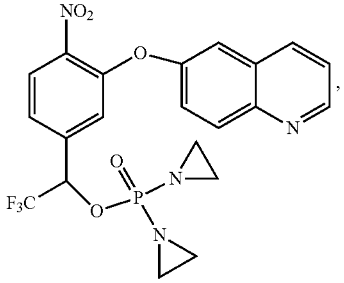
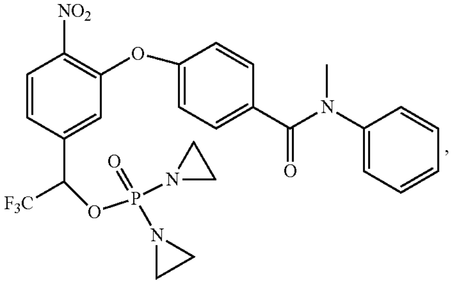

-continued

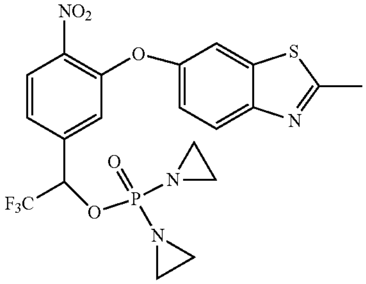
,

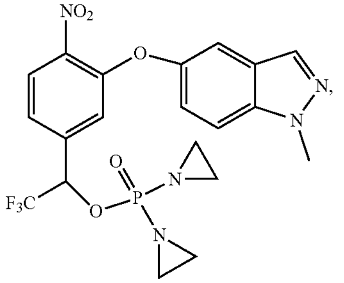
,

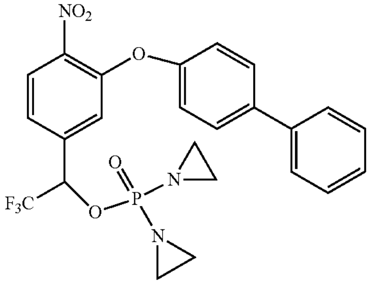
,

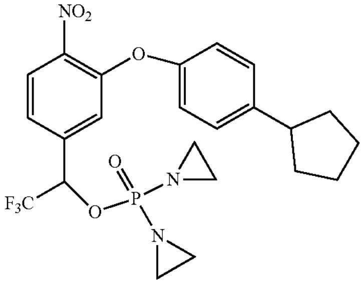

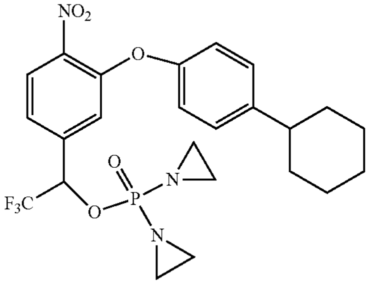
and

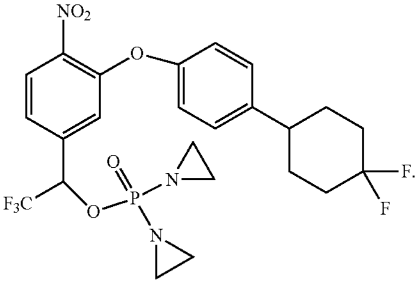
.

Further, regarding the compounds provided above, the salts may be basic salts or be acid salts.

The compounds described herein may also include the form of their salts of formula II or formula III. In other words, the present invention provides pharmaceutically acceptable salts of the compounds as shown herein. The salts may be basic salts, including the salts of the compounds with an inorganic base (such as alkali metal hydroxide and alkaline earth metal hydroxide) or with an organic base (such as monoethanolamine, diethanolamine or triethanolamine). Alternatively, the salts may be acid salts, including the salts of the compounds with an inorganic acid (such as hydrochloric acid, hydrobromic acid, hydroiodic acid, nitric acid, perchloric acid, sulfuric acid or phosphoric acid) or with an organic acid (such as methanesulfonic acid, trifluoromethanesulfonic acid, ethanesulfonic acid, benzenesulfonic acid, p-toluenesulfonic acid, fumaric acid, oxalic acid, maleic acid and citric acid). It is a well-known technology in the art to select and prepare an acceptable salt, a solvate, and the like of a compound.

Further, regarding the compounds provided above, the solvate is hydrate, alcoholate and the like.

The compounds described herein may also be used in the form of solvates. In other words, the present invention provides pharmaceutically acceptable solvates of the compounds of formula II or III as shown herein. The solvate is hydrate, alcoholate and the like, wherein the alcoholate includes ethanolate.

Further, the present invention also provides use of the aforementioned compounds of formula II or formula III in the manufacture of a medicament for treating tumors and cancers.

Further, the present invention also provides a medicament or formulation comprising the aforementioned compounds of formula II or formula III, for use in treating tumors and cancer diseases in patients.

The tumors and cancers include lung cancer, non-small cell lung cancer, liver cancer, pancreatic cancer, stomach cancer, bone cancer, esophagus cancer, breast cancer, prostate cancer, testicular cancer, colon cancer, ovarian cancer, bladder cancer, cervical cancer, melanoma, squamous cell carcinoma, basal cell carcinoma, adenocarcinoma, sweat gland carcinoma, sebaceous gland carcinoma, papillary carcinoma, papillary adenocarcinoma, cystic adenocarcinoma, cystic carcinoma, medullary carcinoma, bronchial carcinoma, osteocyte carcinoma, epithelial carcinoma, carcinoma of bile duct, choriocarcinoma, embryonal carcinoma, seminoma, Wilm's tumor, glioblastoma, astrocytoma, medulloblastoma, craniopharyngioma, ependymoma, pineal tumor, hemocytoblastoma, vocal cords neuroma, meningioma, neuroblastoma, optic neuroblastoma, retinoblastoma, neurofibroma, fibrosarcoma, fibroblastoma, fibroma, fibroadenoma, fibrochondroma, fibrocystoma, fibromyxoma, fibroosteoma, fibromyxosarcoma, fibropapilloma, myxosarcoma, myxocystoma, myxochondroma, myxochondrosarcoma, myxochondrofibrosarcoma, myxadenoma, myxoblastoma, liposarcoma, lipoma, lipoadenoma, lipoblastoma, lipochondroma, lipofibroma, lipoangioma, myxolipoma, chondrosarcoma, chondroma, chondromyoma, chordoma, choriocarcinoma, chorioepithelioma, chorioblastoma, osteosarcoma, osteoblastoma, osteochondrofibroma, osteochondrosarcoma, osteochondroma, osteocystoma, osteodentinoma, osteofibroma, fibrosarcoma of bone, angiosarcoma, hemangioma, angiolipoma, angiochondroma, hemangioblastoma, angiokeratoma, angioglioma, angioendothelioma, angiofibroma, angiomyoma, angiolipoma, angiolymphangioma, angiolipoleiomyoma, angiomyolipoma, angiomyoneuroma, angiomyxoma, angioreticuloma, lymphangiosarcoma, lymphogranuloma, lymphangioma, lymphoma, lymphomyxoma, lymphosarcoma, lymphangiofibroma, lymphocytoma, lymphoepithelioma, lymphoblastoma, endothelioma, endoblastoma, synovioma, synovial sarcoma, mesothelioma, connective tissue tumor, Ewing's tumor, leiomyoma, leiomyosarcoma, leiomyoblastoma, leiomyofibroma, rhabdomyoma, rhabdomyosarcoma, rhabdomyomyxoma, acute lymphatic leukemia, acute myelogenous leukemia, anemia of chronic disease, polycythemia, lymphoma, endometrial cancer, glioma, colorectal cancer, thyroid cancer, urothelial cancer or multiple myeloma; preferably, the cancers or turners are cancers or tumors of central nervous system.

Experiments have confirmed that some of the compounds of the present invention have relatively good cell membrane penetrability, and may be able to traverse the blood brain barrier relatively well into the central nervous system. Therefore, these compounds can more easily act on tumors and cancers in the cranial cavity of the brain, and the spinal cord of the central nervous system.

The present invention provides a method for treating cancer or tumor, comprising a step of applying the aforementioned medicament or formulation; and a step of determining an AKR1C3 reductase content or expression level of cancer cells in a patient using an AKR1C3 antibody, and administering the aforementioned medicament or formulation to the patient if the measured AKR1C3 reductase content or expression level is equal to or greater than a predetermined value.

The AKR1C3 reductase content can be determined using methods including ELISA and ICH methods.

Liquid samples such as plasma and blood can be directly detected using a commercially available human aldo-keto reductase 1c3 (AKR1C3) ELISA assay kit. Other samples are detected after being treated.

The immunohistochemical (ICH) method is suitable for detecting solid tumor samples.

The present invention provides a method for treating cancer or tumor, comprising a step of applying the aforementioned medicament or formulation; and a step of adjusting an AKR1C3 reductase content, and administering the aforementioned medicament or formulation to the patient when the AKR1C3 reductase content is adjusted to be equal to or greater than a predetermined value.

Studies show that after radiotherapy, the content of AKR1C3 enzymes in the tumor tissue of patients with head and neck cancer is increased. Therefore, it is possible to increase the expression level of AKR1C3 enzymes by irradiating the patients' tumor tissue with radioactive rays used in radiotherapy. The radioactive rays includes α, β, γ rays produced by radioisotopes, and x-rays, electron rays, proton beams and other particle beams produced by various x-ray treatment machines or accelerators.

This method is mainly for the situation where the content of AKR1C3 reductase in a patient is relatively low, and is performed by adjusting the content level of AKR1C3 reductase in the patient to an appropriate level through a certain adjustment treatment/administration process.

The present invention also provides the schemes for preparation of the following compounds:

Compounds V and VI are subjected to condensation reaction to close rings to provide the compounds of above formulae II and III:

V

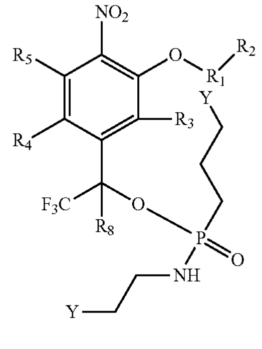

VI

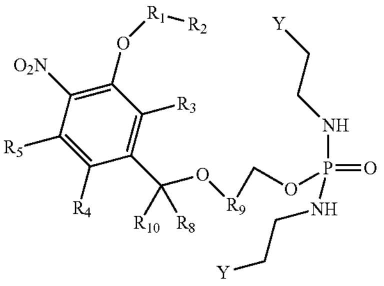

wherein Y is a leaving group, and the remaining variables are defined as those in compounds of formulae II and III.

Further, in the aforementioned preparation method,

Y is Cl, Br, I, —OTs, —$ONO_2$, —OLCMS or —OTf, and in the condensation reaction, organic amines are used as acid-binding agents, and obviously inorganic bases can also be used as acid-binding agents. Inorganic bases include as alkali metal hydroxides, alkaline earth metal hydroxides, carbonates and bicarbonates.

Further, in the above preparation method, Y is Br, and in the condensation reaction, N,N-diisopropylethylamine (DIPEA) is used as an acid-binding agent, and silver oxide ($Ag_2O$) is used as a catalyst.

The present invention also provides the following preparation schemes:

a method for preparing the aforementioned compound, characterized by making

VII

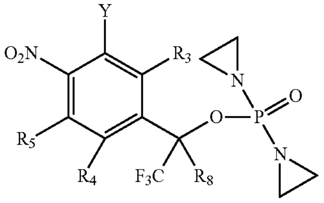

-continued

VIII

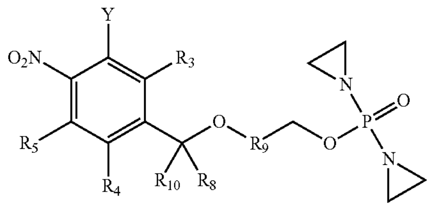

VII react with $R_2R_1OH$ to give II, and making VIII react with $R_2R_1OH$ to give III, or making

IX

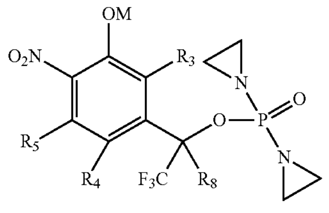

X

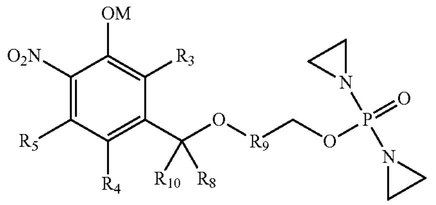

react with $YR_1R_2$ to obtain II and III, wherein Y is a leaving group, M is H or an alkali metal, and the remaining substituents are as defined in the above schemes.

Further, in the above preparation method, Y is F, Cl, Br, I, —OTs, —$ONO_2$, —OLCMS or —OTf, and a base is added during the reaction.

The base here can be an organic base (including organic amine) or an inorganic base (MOH, M being alkali metal or alkaline earth metal): carbonate, bicarbonate, sulfite, and bisulfite of alkali metal or alkaline earth metal, hydroxide and hydride of alkali metal or alkaline earth metal, or other dehydrogenation reagents: alkali metal alkylate (RM, R being an alkyl group, M being an alkali metal), and alkali metal alcoholate (MOR, R being a hydrocarbyl group and M being an alkali metal).

Regarding the medicament or formulation described herein, the prepared medicament contains a specific dosage range of the shown compounds or salts or solvates thereof, and/or the prepared medicament is in a specific dosage form and is administered using a specific mode of administration.

Regarding the use described herein, the prepared medicament may also contain pharmaceutically acceptable auxiliaries or excipients. The medicament can be any dosage form for clinical administration, such as tablets, suppositories, dispersible tablets, enteric-coated tablets, chewable tablets, orally disintegrating tablets, capsules, sugar coated agents, granules, dry powders, oral solutions, a small needle for injection, lyophilized powder for injection, or infusion solutions. According to the specific dosage form and the mode of administration, the pharmaceutically acceptable auxiliaries or excipients in the medicament may include one or more of the following: diluent, solubilizer, disintegrant, suspension, lubricant, adhesive, filler, flavoring agent, sweetener, antioxidant, surfactant, preservative, wrapping agent and pigment.

Preferably, the patient is a mammal, more preferably a human.

DETAILED DESCRIPTION OF THE INVENTION

The present invention will be described below with reference to specific examples. Those skilled in the art could understand that these examples are only used for describing the invention and do not in any way limit its scope.

The experimental methods in the following examples are all conventional methods unless otherwise specified. The raw materials of the medicaments, the reagents and the like used in the following examples are all commercially available products unless otherwise specified.

"Patient" and "subject" are used interchangeably to refer to a mammal in need of treatment for cancer. Generally, the patient is a human. Generally, the patient is a human diagnosed with cancer. In certain embodiments, a "patient" or "subject" may refer to a non-human mammal used in screening, characterizing, and evaluating drugs and therapies, such as, a non-human primate, a dog, cat, rabbit, pig, mouse or a rat.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

"Solid tumor" refers to solid tumors including, but not limited to, metastatic tumors in bone, brain, liver, lungs, lymph node, pancreas, prostate, skin and soft tissue (sarcoma).

"Therapeutically effective amount" of a drug refers to an amount of a drug that, when administered to a patient with cancer, will have the intended therapeutic effect, e.g., alleviation, amelioration, palliation or elimination of one or more manifestations of cancer in the patient A therapeutic effect does not necessarily occur by administration of one dose, and may occur only after administration of a series of doses. Thus, a therapeutically effective amount may be administered in one or more administrations.

"Treatment of" a condition or patient refers to taking steps to obtain beneficial or desired results, including clinical results. For purposes of this invention, beneficial or desired clinical results include, but are not limited to, alleviation or improvement of one or more symptoms of cancer; diminishment of extent of disease; delay or slowing of disease progression; alleviation, palliation, or stabilization of the disease state; or other beneficial results. Treatment of cancer may, in some cases, result in partial response or stable disease.

"Tumor cells" refers to tumor cells of any appropriate species, e.g., mammalian such as murine, canine, feline, equine or human.

The above description of embodiments of the present invention does not limit the present invention. Those skilled in the art can make various modifications and changes according to the present invention, and any modification and change within the spirit of the present invention shall be covered in the scope of the claims appended to the present invention.

1. Test Data on Inhibition of H460 Cancer Cells

In vitro human tumor cell line cytotoxicity assays.

In vitro proliferation data on the H460 non-small cell lung cancer human tumor cell line is reported below in the compound table.

$IC_{50}$ values are reported in nanomolar and are result from exposure of compounds at various concentrations for 2 hrs followed by a wash step and addition of fresh media followed by growth and cell viability staining and comparison to control only treated with media.

Specifically, exponentially growing cells were seeded at a density of $4\times10^3$ cells per well in a 96 well plate and incubated at 37° C. in 5% $CO_2$, 95% air and 100% relative humidity for 24 hours prior to addition of test compounds. Compounds were solubilized in 100% DMSO at 200 times the desired final test concentration. At the time of drug addition, compounds were further diluted to 4 times the desired final concentration with complete medium. Aliquots of 50 μl of compound at specified concentrations were added to microtiter wells already containing 150 μl of medium, resulting in the final drug concentration reported. After drug addition, the plates were incubated for an additional 2 hours at 37° C., 5% $CO_2$, 95% air, and 100% relative humidity, then the drug was washed off and fresh medium was added and the plates were incubated for addition 70 hrs at 37° C., 5% $CO_2$, 95% air and 100% relative humidity. At the end of this incubation, the viable cells were quantified using the AlamarBlue assay. The drug concentration resulting in growth inhibition of 50% ($IC_{50}$) was calculated using computer software, and the results were listed in the table below.

Similarly, in order to further verify that the compounds are activated by human AKR1C3 (aldosterone reductase family 1 member $C_3$), the effect of some of the compounds on the proliferation of H460 cancer cells was tested in the presence of a specific AKR1C3 enzyme inhibitor (at 3 micromolar concentration). The inhibitor-added compound solution was added to the cell culture two hours before the treatment with the compound. The inhibitor used was compound 36, i.e.,

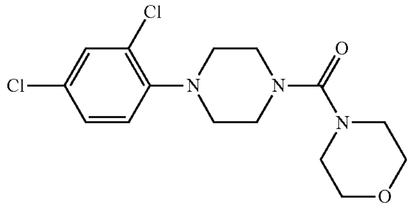 [SMILES: O=C(N1CCOCC1)N1CCN(c2ccc(Cl)cc2Cl)CC1]

(TH-3021) in Flanagan et al., *Bioorganic and Medicinal Chemistry* (2014), pages 962-977.

| No. | Compounds | $IC_{50}$ (nM) | $IC_{50}$ (nM) obtained when the AKR1C3 inhibitor TH-3021 was added |
|---|---|---|---|
| 1 | 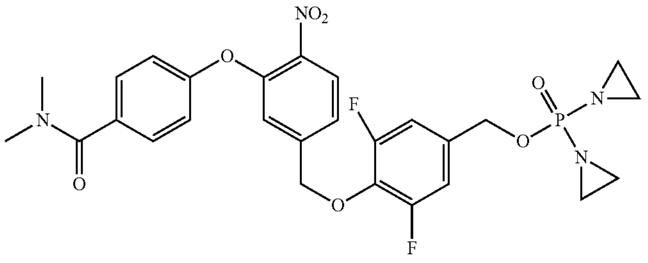 [SMILES: CN(C)C(=O)c1ccc(Oc2cc(COc3c(F)cc(COP(=O)(N4CC4)N4CC4)cc3F)ccc2[N+](=O)[O-])cc1] | 1.97 | 460 |
| 2 | 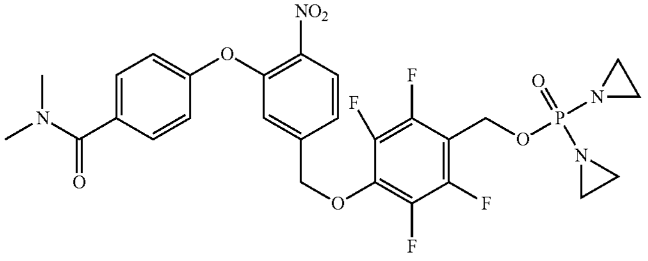 [SMILES: CN(C)C(=O)c1ccc(Oc2cc(COc3c(F)c(F)c(COP(=O)(N4CC4)N4CC4)c(F)c3F)ccc2[N+](=O)[O-])cc1] | 0.3518 | >1000 |

-continued
| No. | Compounds | $IC_{50}$ (nM) | $IC_{50}$ (nM) obtained when the AKR1C3 inhibitor TH-3021 was added |
|---|---|---|---|
| 3 | 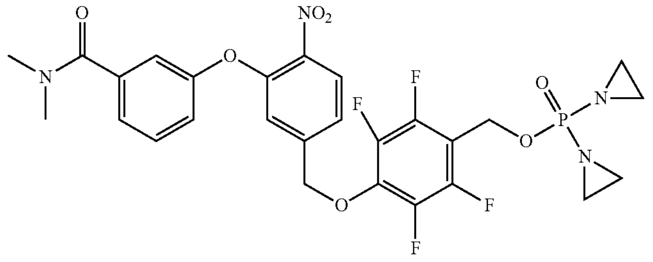 [SMILES: CN(C)C(=O)c1cccc(Oc2cc(COc3c(F)c(F)c(COP(=O)(N4CC4)N4CC4)c(F)c3F)ccc2[N+](=O)[O-])c1] | 0.4172 | >1000 |
| 4 | 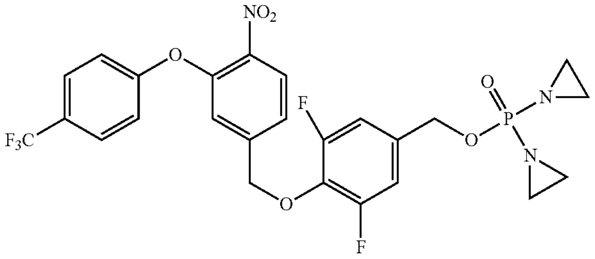 [SMILES: O=[N+]([O-])c1ccc(COc2c(F)cc(COP(=O)(N3CC3)N3CC3)cc2F)cc1Oc1ccc(C(F)(F)F)cc1] | 9.308 | >1000 |
| 5 | 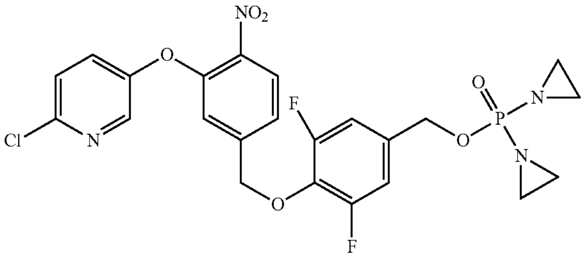 [SMILES: O=[N+]([O-])c1ccc(COc2c(F)cc(COP(=O)(N3CC3)N3CC3)cc2F)cc1Oc1ccc(Cl)nc1] | 5.874 | 228.1 |
| 6 | 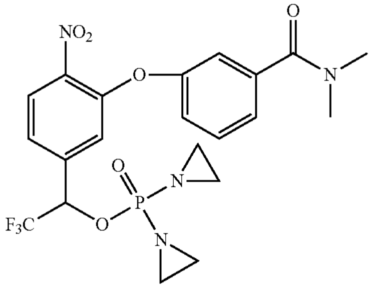 [SMILES: CN(C)C(=O)c1cccc(Oc2cc(C(OP(=O)(N3CC3)N3CC3)C(F)(F)F)ccc2[N+](=O)[O-])c1] | 1.268 | 813.1 |
| 7 | 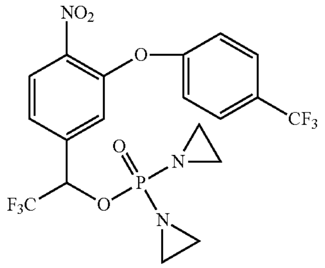 [SMILES: O=[N+]([O-])c1ccc(C(OP(=O)(N2CC2)N2CC2)C(F)(F)F)cc1Oc1ccc(C(F)(F)F)cc1] | 25.57 | >1000 |

-continued
| No. | Compounds | $IC_{50}$ (nM) | $IC_{50}$ (nM) obtained when the AKR1C3 inhibitor TH-3021 was added |
|---|---|---|---|
| 8 | 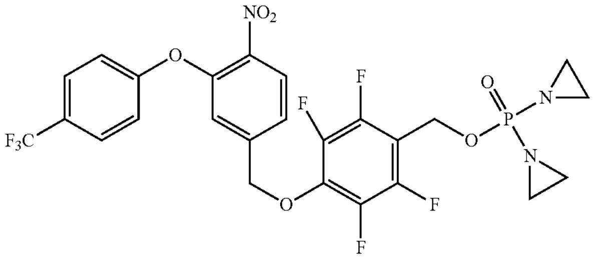 [SMILES: O=[N+]([O-])c1ccc(COc2c(F)c(F)c(COP(=O)(N3CC3)N3CC3)c(F)c2F)cc1Oc1ccc(C(F)(F)F)cc1] | 0.5265 | >1000 |
| 9 | 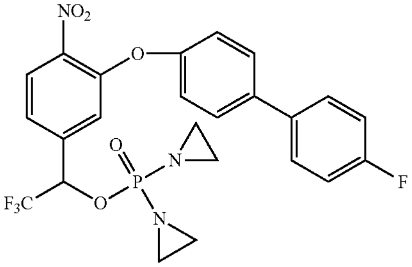 [SMILES: O=[N+]([O-])c1ccc(C(OP(=O)(N2CC2)N2CC2)C(F)(F)F)cc1Oc1ccc(-c2ccc(F)cc2)cc1] | 18.45 | >1000 |
| 10 | 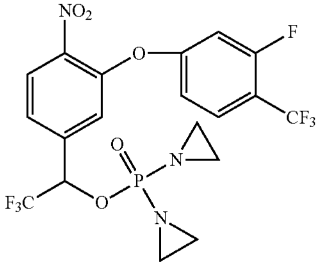 [SMILES: O=[N+]([O-])c1ccc(C(OP(=O)(N2CC2)N2CC2)C(F)(F)F)cc1Oc1ccc(C(F)(F)F)c(F)c1] | Not tested | Not tested |
| 11 | 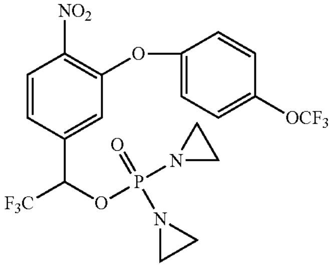 [SMILES: O=[N+]([O-])c1ccc(C(OP(=O)(N2CC2)N2CC2)C(F)(F)F)cc1Oc1ccc(OC(F)(F)F)cc1] | 137.2 | >1000 |
| 12 | 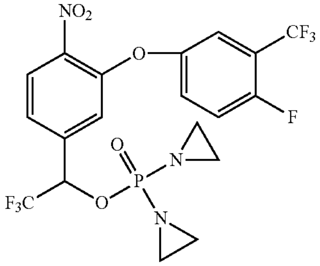 [SMILES: O=[N+]([O-])c1ccc(C(OP(=O)(N2CC2)N2CC2)C(F)(F)F)cc1Oc1ccc(F)c(C(F)(F)F)c1] | 87.3 | >1000 |

-continued
| No. | Compounds | $IC_{50}$ (nM) | $IC_{50}$ (nM) obtained when the AKR1C3 inhibitor TH-3021 was added |
|---|---|---|---|
| 13 | 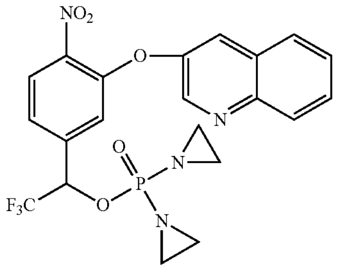 [SMILES: O=[N+]([O-])c1ccc(C(OP(=O)(N2CC2)N2CC2)C(F)(F)F)cc1Oc1cnc2ccccc2c1] | 42.25 | >1000 |
| 14 | 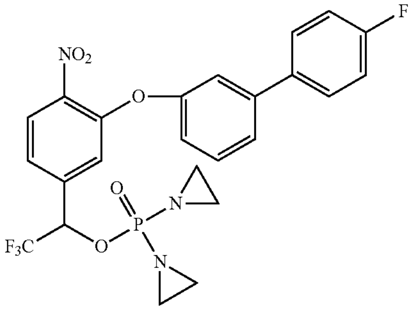 [SMILES: O=[N+]([O-])c1ccc(C(OP(=O)(N2CC2)N2CC2)C(F)(F)F)cc1Oc1cccc(-c2ccc(F)cc2)c1] | 29.99 | >1000 |
| 15 | 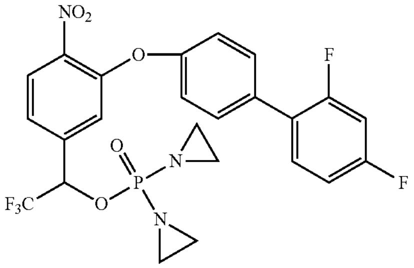 [SMILES: O=[N+]([O-])c1ccc(C(OP(=O)(N2CC2)N2CC2)C(F)(F)F)cc1Oc1ccc(-c2ccc(F)cc2F)cc1] | 11.39 | >1000 |
| 16 | 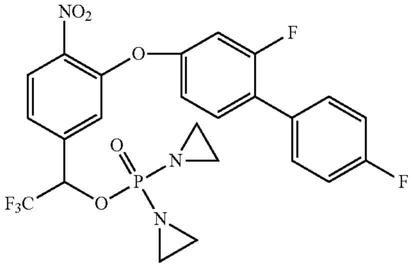 [SMILES: O=[N+]([O-])c1ccc(C(OP(=O)(N2CC2)N2CC2)C(F)(F)F)cc1Oc1ccc(-c2ccc(F)cc2)c(F)c1] | 6.782 | >1000 |
| 17 | 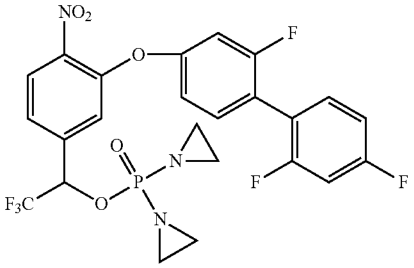 [SMILES: O=[N+]([O-])c1ccc(C(OP(=O)(N2CC2)N2CC2)C(F)(F)F)cc1Oc1ccc(-c2ccc(F)cc2F)c(F)c1] | 7.258 | >1000 |

-continued
| No. | Compounds | $IC_{50}$ (nM) | $IC_{50}$ (nM) obtained when the AKR1C3 inhibitor TH-3021 was added |
|---|---|---|---|
| 18 | 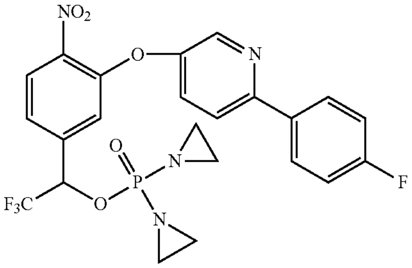 [SMILES: O=[N+]([O-])c1ccc(C(OP(=O)(N2CC2)N2CC2)C(F)(F)F)cc1Oc1ccc(-c2ccc(F)cc2)nc1] | 35.45 | >1000 |
| 19 | 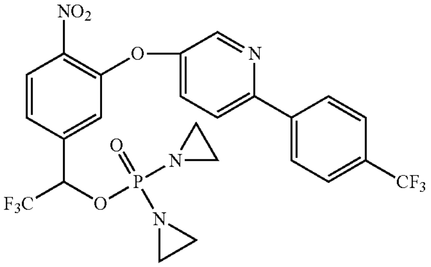 [SMILES: O=[N+]([O-])c1ccc(C(OP(=O)(N2CC2)N2CC2)C(F)(F)F)cc1Oc1ccc(-c2ccc(C(F)(F)F)cc2)nc1] | 312.9 | >1000 |
| 20 | 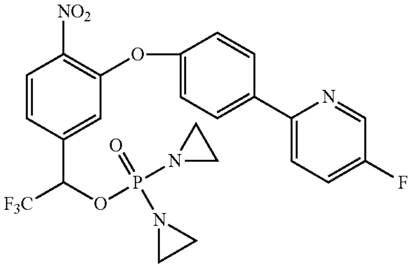 [SMILES: O=[N+]([O-])c1ccc(C(OP(=O)(N2CC2)N2CC2)C(F)(F)F)cc1Oc1ccc(-c2ccc(F)cn2)cc1] | 46.81 | >1000 |
| 21 | 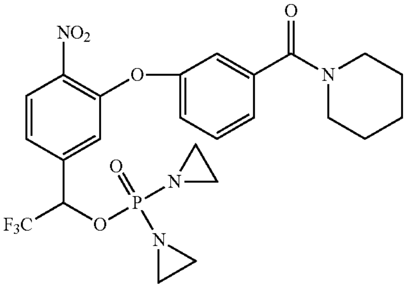 [SMILES: O=C(c1cccc(Oc2cc(C(OP(=O)(N3CC3)N3CC3)C(F)(F)F)ccc2[N+](=O)[O-])c1)N1CCCCC1] | 6.984 | 176.2 |
| 22 | 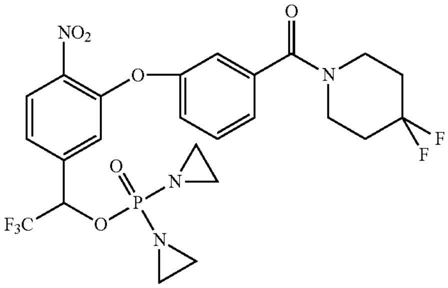 [SMILES: O=C(c1cccc(Oc2cc(C(OP(=O)(N3CC3)N3CC3)C(F)(F)F)ccc2[N+](=O)[O-])c1)N1CCC(F)(F)CC1] | 1.374 | 139.2 |

-continued
| No. | Compounds | $IC_{50}$ (nM) | $IC_{50}$ (nM) obtained when the AKR1C3 inhibitor TH-3021 was added |
|---|---|---|---|
| 23 | 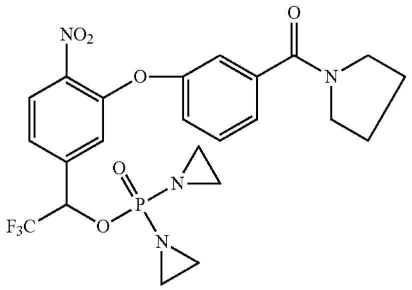 [SMILES: O=C(c1cccc(Oc2cc(C(OP(=O)(N3CC3)N3CC3)C(F)(F)F)ccc2[N+](=O)[O-])c1)N1CCCC1] | 6.04 | 794.8 |
| 24 | 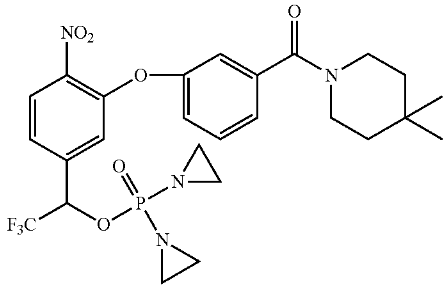 [SMILES: CC1(C)CCN(C(=O)c2cccc(Oc3cc(C(OP(=O)(N4CC4)N4CC4)C(F)(F)F)ccc3[N+](=O)[O-])c2)CC1] | 4.325 | >1000 |
| 25 | 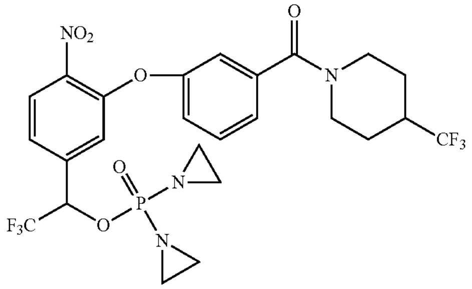 [SMILES: O=C(c1cccc(Oc2cc(C(OP(=O)(N3CC3)N3CC3)C(F)(F)F)ccc2[N+](=O)[O-])c1)N1CCC(C(F)(F)F)CC1] | 1.859 | 179.1 |
| 26 | 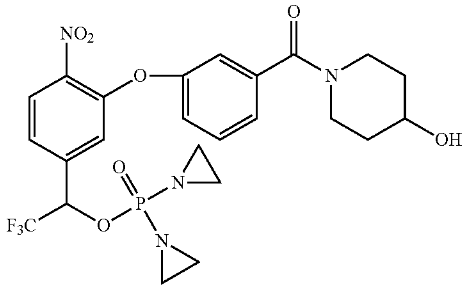 [SMILES: O=C(c1cccc(Oc2cc(C(OP(=O)(N3CC3)N3CC3)C(F)(F)F)ccc2[N+](=O)[O-])c1)N1CCC(O)CC1] | 1.199 | 175.2 |
| 27 | 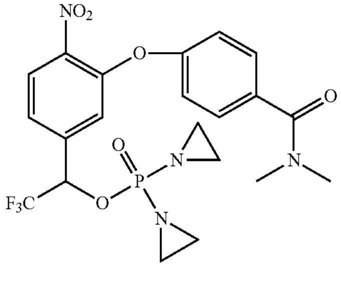 [SMILES: CN(C)C(=O)c1ccc(Oc2cc(C(OP(=O)(N3CC3)N3CC3)C(F)(F)F)ccc2[N+](=O)[O-])cc1] | 9.316 | >1000 |

-continued
| No. | Compounds | $IC_{50}$ (nM) | $IC_{50}$ (nM) obtained when the AKR1C3 inhibitor TH-3021 was added |
|---|---|---|---|
| 28 | 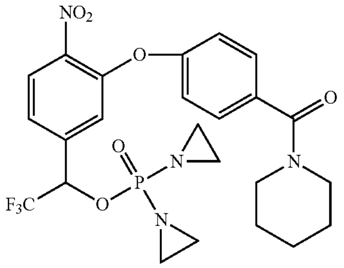 [SMILES: O=C(c1ccc(Oc2cc(C(OP(=O)(N3CC3)N3CC3)C(F)(F)F)ccc2[N+](=O)[O-])cc1)N1CCCCC1] | 2.364 | 649.2 |
| 29 | 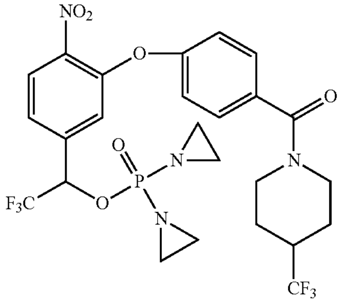 [SMILES: O=C(c1ccc(Oc2cc(C(OP(=O)(N3CC3)N3CC3)C(F)(F)F)ccc2[N+](=O)[O-])cc1)N1CCC(C(F)(F)F)CC1] | 60.08 | >1000 |
| 30 | 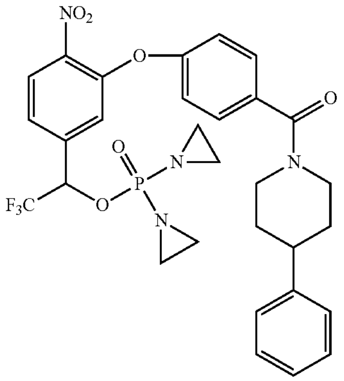 [SMILES: O=C(c1ccc(Oc2cc(C(OP(=O)(N3CC3)N3CC3)C(F)(F)F)ccc2[N+](=O)[O-])cc1)N1CCC(c2ccccc2)CC1] | 79.9 | >1000 |
| 33 | 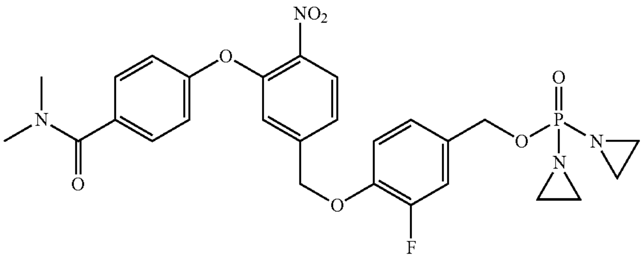 [SMILES: CN(C)C(=O)c1ccc(Oc2cc(COc3ccc(COP(=O)(N4CC4)N4CC4)cc3F)ccc2[N+](=O)[O-])cc1] | Not tested | Not tested |
| 34 | 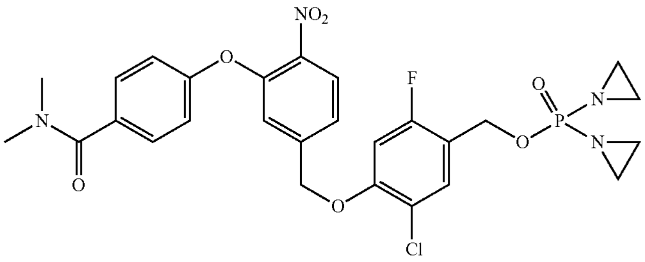 [SMILES: CN(C)C(=O)c1ccc(Oc2cc(COc3cc(F)c(COP(=O)(N4CC4)N4CC4)cc3Cl)ccc2[N+](=O)[O-])cc1] | 38.54 | >1000 |

-continued
| No. | Compounds | $IC_{50}$ (nM) | $IC_{50}$ (nM) obtained when the AKR1C3 inhibitor TH-3021 was added |
|---|---|---|---|
| 35 | 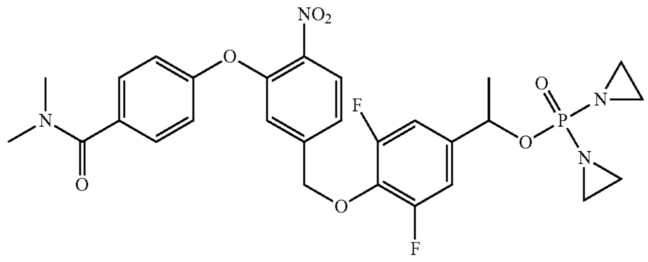 [SMILES: CC(OP(=O)(N1CC1)N1CC1)c1cc(F)c(OCc2ccc([N+](=O)[O-])c(Oc3ccc(C(=O)N(C)C)cc3)c2)c(F)c1] | Not tested | Not tested |
| 36 | 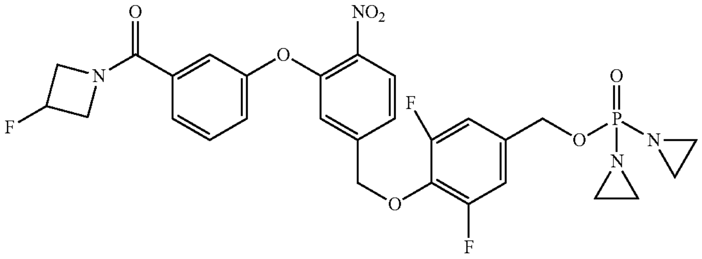 [SMILES: O=C(c1cccc(Oc2cc(COc3c(F)cc(COP(=O)(N4CC4)N4CC4)cc3F)ccc2[N+](=O)[O-])c1)N1CC(F)C1] | <4.37 | 237.5 |
| 37 | 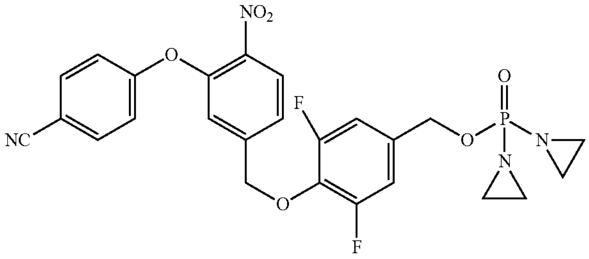 [SMILES: N#Cc1ccc(Oc2cc(COc3c(F)cc(COP(=O)(N4CC4)N4CC4)cc3F)ccc2[N+](=O)[O-])cc1] | 12.34 | 136 |
| 38 | 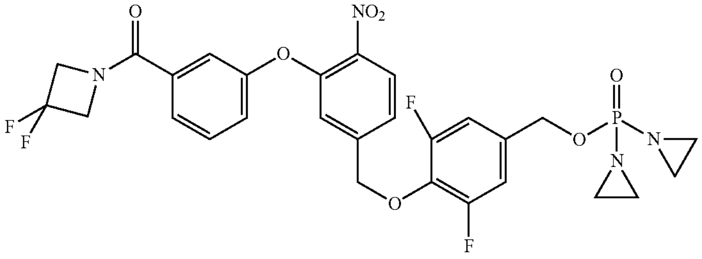 [SMILES: O=C(c1cccc(Oc2cc(COc3c(F)cc(COP(=O)(N4CC4)N4CC4)cc3F)ccc2[N+](=O)[O-])c1)N1CC(F)(F)C1] | 5.526 | 267.1 |
| 39 | 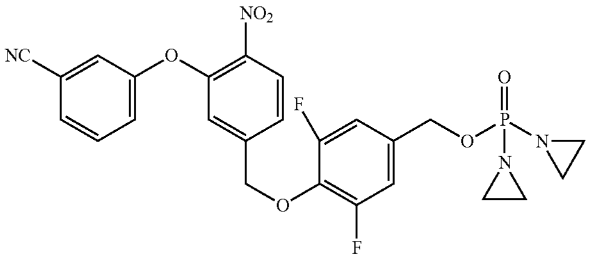 [SMILES: N#Cc1cccc(Oc2cc(COc3c(F)cc(COP(=O)(N4CC4)N4CC4)cc3F)ccc2[N+](=O)[O-])c1] | 7.794 | 137.3 |

-continued
| No. | Compounds | IC$_{50}$ (nM) | IC$_{50}$ (nM) obtained when the AKR1C3 inhibitor TH-3021 was added |
|---|---|---|---|
| 40 | 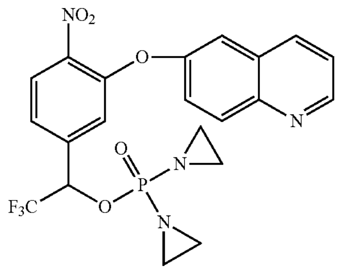 [SMILES: O=[N+]([O-])c1ccc(C(OP(=O)(N2CC2)N2CC2)C(F)(F)F)cc1Oc1ccc2ncccc2c1] | 14.72 | >1000 |
| 41 | 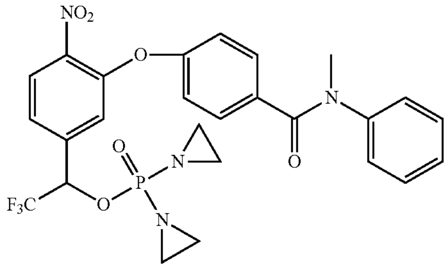 [SMILES: CN(C(=O)c1ccc(Oc2cc(C(OP(=O)(N3CC3)N3CC3)C(F)(F)F)ccc2[N+](=O)[O-])cc1)c1ccccc1] | 2.541 | 341.2 |
| 42 | 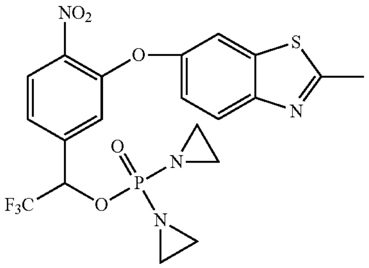 [SMILES: Cc1nc2ccc(Oc3cc(C(OP(=O)(N4CC4)N4CC4)C(F)(F)F)ccc3[N+](=O)[O-])cc2s1] | 29.3 | >1000 |
| 43 | 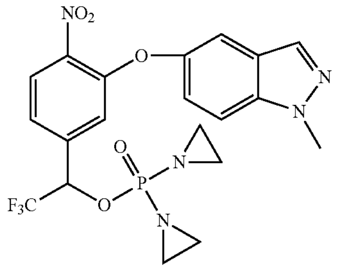 [SMILES: Cn1ncc2cc(Oc3cc(C(OP(=O)(N4CC4)N4CC4)C(F)(F)F)ccc3[N+](=O)[O-])ccc21] | 30.42 | 102 |
| 44 | 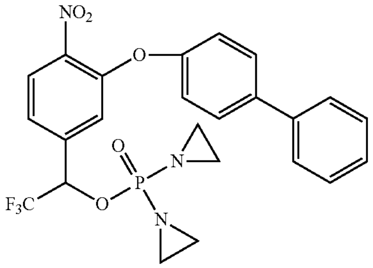 [SMILES: O=[N+]([O-])c1ccc(C(OP(=O)(N2CC2)N2CC2)C(F)(F)F)cc1Oc1ccc(-c2ccccc2)cc1] | 9.418 | >1000 |

-continued

| No. | Compounds | $IC_{50}$ (nM) | $IC_{50}$ (nM) obtained when the AKR1C3 inhibitor TH-3021 was added |
|---|---|---|---|
| 47 | 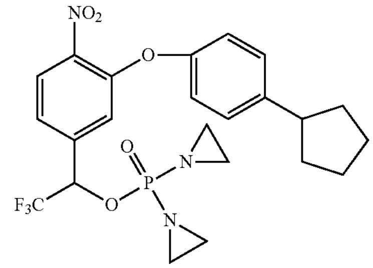 [SMILES: O=[N+]([O-])c1ccc(C(OP(=O)(N2CC2)N2CC2)C(F)(F)F)cc1Oc1ccc(C2CCCC2)cc1] | 8.135 | Not tested |
| 48 | 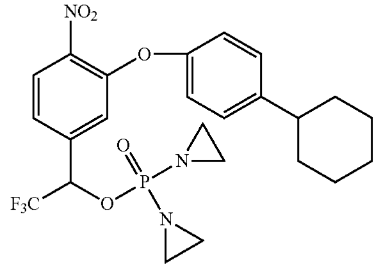 [SMILES: O=[N+]([O-])c1ccc(C(OP(=O)(N2CC2)N2CC2)C(F)(F)F)cc1Oc1ccc(C2CCCCC2)cc1] | 3.697 | Not tested |
| 49 | 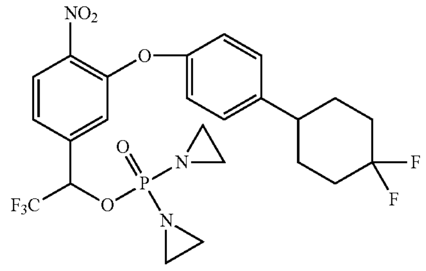 [SMILES: O=[N+]([O-])c1ccc(C(OP(=O)(N2CC2)N2CC2)C(F)(F)F)cc1Oc1ccc(C2CCC(F)(F)CC2)cc1] | 9.605 | >1000 |

The experiment demonstrates that human AKR1C3 promotes the activation of the above compounds, and at the same time the compounds of this series have the activity of inhibiting the proliferation of cancer cells.

2. Examples of Synthesis of Compounds

THF stands for tetrahydrofuran; DCM stands for dichloromethane; EA or EtOAC stands for ethyl acetate; TEA stands for triethylamine; HPLC stands for high-performance liquid chromatography; MTBE stands for methyl tert-butyl ether; DMAP stands for 4-dimethylaminopyridine; DBAD stands for di-tert-butyl azodicarboxylate; TFA stands for trifluoroacetic acid; LCMS stands for liquid chromatography mass spectrometry; EtOH stands for ethanol; t-BuOH stands for tert-butanol; DMF stands for dimethylformamide; PE stands for petroleum ether; eq. stands for equivalent, i.e., molar ratio; TBAF stands for tetrabutylammonium fluoride; and DIPEA stands for N, N-diisopropylethylamine;

In the synthesis process, all the chemical reagents and medicaments whose sources were not indicated were analytically or chemically pure and were purchased from commercial reagent companies.

Other English abbreviations mentioned herein are subject to the interpretation in the field of organic chemistry.

Synthesis of Compound No. 1

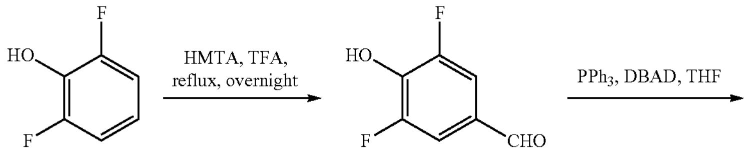

1-D 1-E

-continued

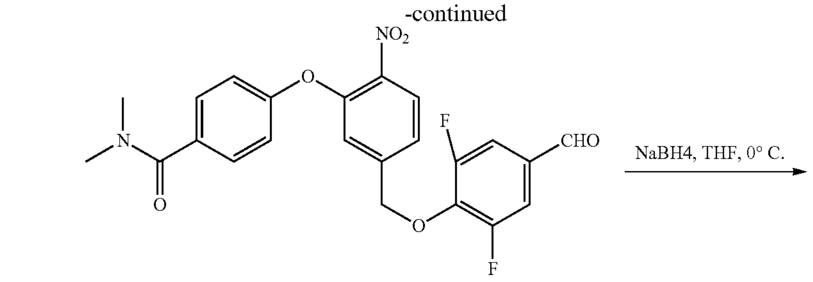

1-F

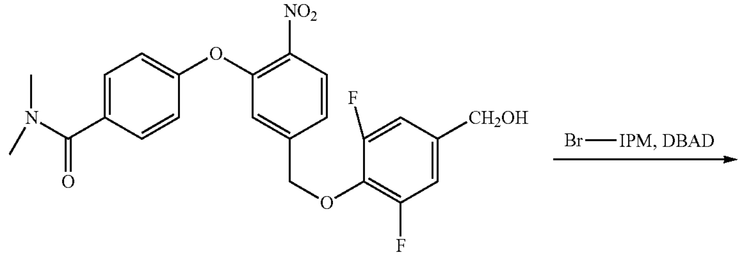

1-B

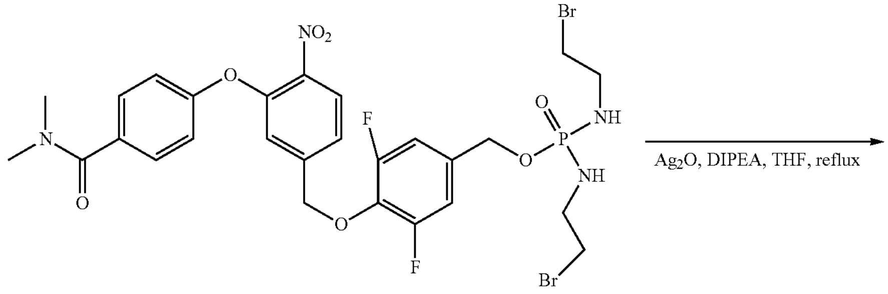

1-C

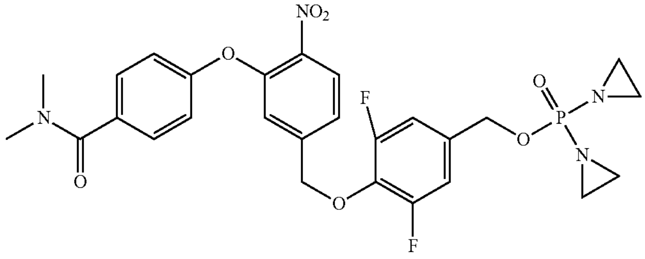

1

1-D (5 g, 38.4 mmol) was dissolved in TFA (40 mL), and urotropine (5.6 g, 38.4 mmol, 1 eq., commercially available) was added, and refluxed overnight. After the reaction was complete, the temperature was reduced to room temperature. The solvent was removed by concentration. The residue was dissolved in DCM (70 mL), washed with $NaHCO_3$ solution, and then was adjusted to a pH of 1 with concentrated hydrochloric acid. The aqueous phase was extracted with DCM (50 mL×2), and the organic phases were combined, dried with $Na_2SO_4$ and concentrated to give 1-E (2.5 g, with a yield of 41.3%) which is a white solid. $^1$H-NMR (300M, $CDCl_3$): δ ppm 9.82 (s, 1H), 7.49 (d, J=6.6 Hz, 2H). LCMS: Calculated 158.1, found 157.0 ([M−H]$^-$).

Under the protection of nitrogen,

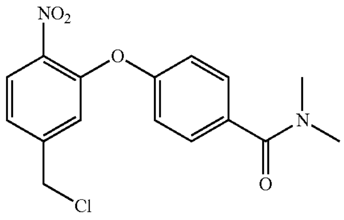 [SMILES: CN(C)C(=O)c1ccc(Oc2cc(CCl)ccc2[N+](=O)[O-])cc1]

(1 g, 3.16 mmol) and 1-E (1 g, 6.32 mmol) were dissolved in ultra-dry THF (15). Triphenylphosphine (1.66 g, 6.32 mml, 2 eq.) was added. A THF solution (6 mL) of DBAD (1.46 g, 6.32 mmol, 2 eq.) was added dropwise at 0° C. The reaction was carried out at room temperature overnight. 8 mL of water was added dropwise at 0° C. Extraction was performed with DCM (20 ml×3) followed by drying and concentration. The sample was mixed and passed through a column (200-300 mesh silica gel, petroleum ether:EA=3:1) to obtain 1-F (680 mg, with a yield of 47% and a content of 80%) as a light yellow solid.

Under the protection of nitrogen, 1-F (510 mg, 1.11 mmol) was dissolved in THF (5 mL). The temperature was reduced to 0° C. Sodium borohydride (84 mg, 2.22 mmol, 2 eq.) was added in batches, and the temperature was kept at 0° C. The reaction was performed for 1 hour. After the reaction was complete, saturated ammonium chloride aqueous solution (3 mL) was added dropwise. Extraction was performed with EA (10 mL×3) followed by washing with brine, drying, concentration, and column separation (100-200 mesh silica gel, DCM:methanol=50:1) to obtain the product 1-B (300 mg, yield=58.9%) as a light yellow solid. $^1$H-NMR (300M, $CDCl_3$): δ ppm 8.01 (d, J=8.4 Hz, 1H), 7.43 (d, J=8.7 Hz, 2H), 7.34-7.37 (m, 1H), 6.86 (d, J=8.4 Hz, 1H), 5.14 (s, 2H), 4.60 (s, 2H), 3.09 (brs, 6H). LCMS: Calculated 458.4, found 459.0 ([M+H]+).

Under the protection of nitrogen, 1-B (300 mg, 0.65 mmol) was dissolved in THF (5 mL). Triphenylphosphine (375 mg, 1.43 mmol, 2.2 eq.), and a bromoisophosphoramide nitrogen mustard intermediate (Br-IPM, 442 mg, 1.43 mmol, 2.2 eq., commercially available) were added. The temperature was reduced to 0° C. DBAD (329 mg, 1.43 mmol, 2.2 eq.) in THF (3 mL) was added dropwise, and reacted at room temperature for 3 h. 3 mL water was added dropwise. Extraction was performed with DCM (10 mL×3) followed by drying, concentration, and column separation (200-300 mesh silica gel, DCM:methanol=30:1) to obtain the product (400 mg, with a yield of 82%) as a reddish brown solid. $^1$H-NMR (300M, $CDCl_3$): δ ppm 7.99 (d, J=8.4 Hz, 1H), 7.48-7.46 (m, 2H), 7.33-7.31 (m, 1H), 7.12 (s, 1H), 7.00 (d, J=8.1 Hz, 2H), 6.93 (d, J=8.4 Hz, 2H), 5.16 (s, 2H), 4.93 (d, J=8.4 Hz, 2H), 3.45-3.43 (m, 4H), 3.37-3.32 (m, 4H), 3.07 (brs, 6H). LCMS: Calculated 750.3, found 750.8 ([M+1]+).

Under the protection of nitrogen, 1-C (400 mg, 0.533 mmol) was dissolved in ultra-dry THF (4 mL). Silver oxide (1.46 g, 6.29 mmol, 11.8 eq.) was added, and diisopropylethylamine (345 mg, 2.67 mmol, 5 eq.) was added dropwise. The temperature was increased to reflux temperature, the reaction was monitored by LCMS, and the reaction was complete in 2.5 h. Suction filtration through Celite® was performed followed by washing with THF several times, and concentration at low temperature to give Compound No. 1 (19 mg, with a yield of 6.07%) as a white solid. $^1$H-NMR (400M, $CDCl_3$): δ ppm 7.99 (d, J=7.2 Hz, 1H), 7.45 (d, J=7.8 Hz, 2H), 7.32 (d, J=8.4 Hz, 1H), 7.16 (d, J=1.6 Hz, 1H), 7.04-7.06 (m, 2H), 6.95 (d, J=8.4 Hz, 2H), 5.15 (s, 2H), 5.05 (d, J=8.0 Hz, 2H), 3.11 (s, 3H), 3.03 (s, 3H), 2.23-2.13 (m, 8H). LCMS: Calculated 588.0, found 589.0 ([M+H]+).

Synthesis of Compound No. 2

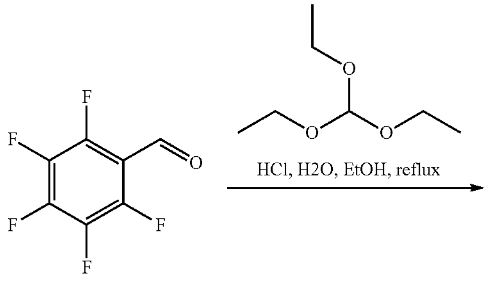

2-A1

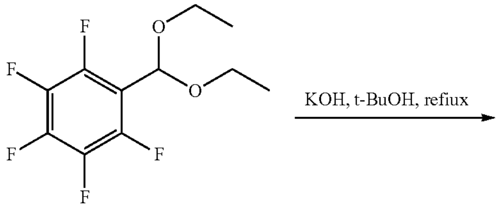

2-A2

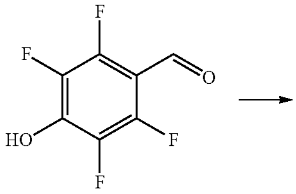

2-A3

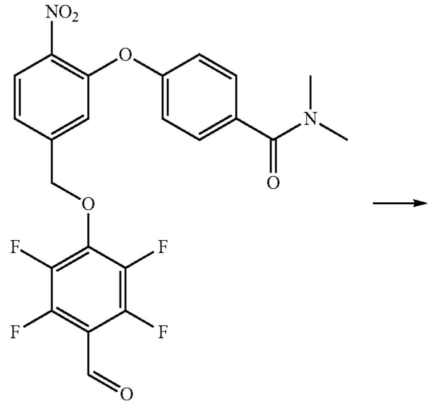

2-A4

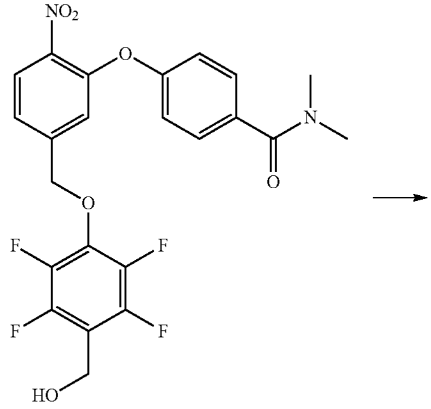

2-A5

-continued

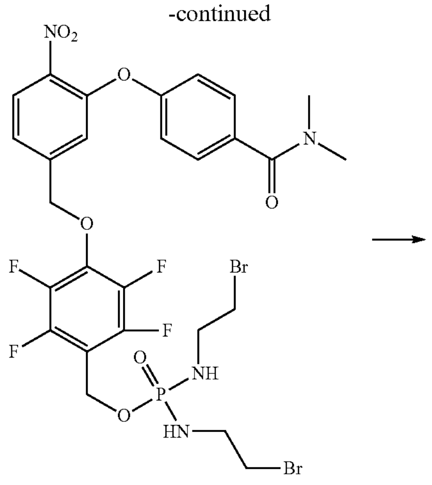

2-A6

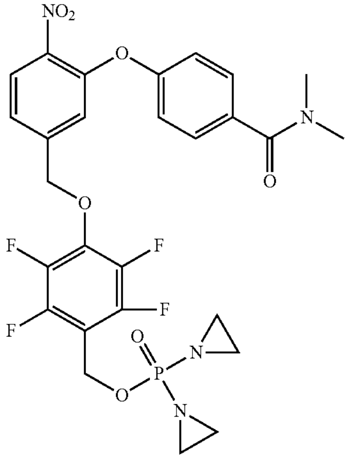

2

2-A1 (10.0 g, 50.99 mmol), triethyl orthoformate (9.8 g, 66.07 mmol, 1.32 eq.), 12N HCl (0.15 ml) were added to EtOH (30 ml), and refluxed overnight. After the completion of the reaction, the solvent was spin-dried to obtain 2-A2 (11.2 g, a crude product).

2-A2 (11.2 g, a crude product, 51.0 mmol) and KOH (2.3 g, 204.0 mmol, 4 eq.) were refluxed in t-BuOH (150 ml) for 4 h before the completion of the reaction. The temperature was reduced to room temperature, water (100 ml) was added, and extraction was performed with EtOAc (100 ml×3). The aqueous phase was adjusted to pH of 3-4 with 12N HCl and stirred overnight. After that it was extracted with EtOAc (100 ml×3), dried with $Na_2SO_4$, spin-dried and then slurried with petroleum ether (PE) (20 ml) to obtain 2-A3 (4.4 g, with an yield of 4.4%) as a off-white solid. $^1$H-NMR (400M, $CDCl_3$): δ ppm 10.21 (s, 1H), 6.46 (s, 1H). LCMS: Calculated 194.0, found 192.8 ([M−H]−).

Under the protection of nitrogen, 2-B1 (500 mg, 1.5 mmol), i.e.,

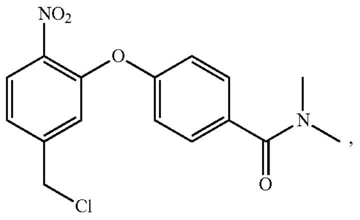 [SMILES: CN(C)C(=O)c1ccc(Oc2cc(CCl)ccc2[N+](=O)[O-])cc1]

2-A3 (1.45 g, 7.5 mmol, 5 eq.), and DIEA (965 mg, 7.5 mmol, 5 eq.) were added to DMF (5 ml) and heated to 50° C. overnight. The conversion of the reaction no longer increased after reaching about 50%. After cooling down to room temperature, $H_2O$ (20 ml) was added and extraction was performed with EtOAc (20 ml×3). The organic phase was washed with brine (15 ml×3), and washed with water (15 ml×5). The organic phase was dried with $Na_2SO_4$ and spin-dried to remove the solvent, and passed through a 200-300 silica gel column (PE:EtOAc=3:1) to obtain 2-A4 (290 mg, yield=33.9%) as a light yellow solid. $^1$H-NMR (400M, $CDCl_3$): δ ppm 10.15 (s, 1H), 7.94 (d, J=8.4 Hz, 1H), 7.41 (d, J=8.4 Hz, 2H), 7.23 (d, J=8.4 Hz, 1H), 7.04-6.99 (m, 3H), 5.31 (s, 2H), 3.06 (s, 3H), 2.96 (s, 3H). LCMS: Calculated 492.1, found 493.1 ([M+H]+).

Under the protection of nitrogen, 2-A4 (270 mg, 0.548 mmol) was dissolved in THF (3 ml) before the temperature was reduced to 0° C. Then, $NaBH_4$ (42 mg, 1.1 mmol, 2 eq.) was added to the system in batches, and the reaction was complete in 30 min. $H_2O$ (5 ml) was added dropwise and extraction was performed with DCM (10 ml×3). The organic phase was washed with water (10 ml×3), and the organic phase was dried with anhydrous $Na_2SO_4$, spin-dried, and passed through a column (PE:EtOAc=1:1) to obtain 2-A5 (95 mg, yield=35.0%) as a yellow solid. $^1$H-NMR (400M, $CDCl_3$): δ ppm 8.01 (d, J=8.4 Hz, 1H), 7.45 (d, J=8.4 Hz, 2H), 7.33-7.30 (m, 1H), 7.00 (d, J=8.4 Hz, 2H), 6.94 (s, 1H), 5.20 (s, 2H), 4.74 (s, 2H), 3.10 (s, 3H), 3.05 (s, 3H). LCMS: Calculated 495.1, found 495.1 ([M+H]$^+$).

Under the protection of nitrogen, $POCl_3$ (100 mg, 0.405 mmol, 2 eq.) was dissolved in DCM (2 ml) and then the temperature was reduced to −40° C. Ten, 2-A5 (100 mg, 0.202 mmol, 1 eq.) and TEA (51 mg, 0.506 mmol, 2.5 eq.) were added to the system, and held at −40° C. for 6 h until the completion of the reaction. 2-Bromoethylamine hydrobromide (338 mg, 1.618 mmol, 8 eq.) was added to the system, and then TEA (164 mg, 1.618 mmol, 8 eq.) was added dropwise to the system. After completion, the temperature was kept at −40° C. and the reaction was complete in 30 min. After the temperature was increased to room temperature, $NH_4Cl$ solution (15 ml) was added dropwise and extraction was performed with DCM (10 ml×3). The organic phase was washed with water (10 ml×3), and the organic phase was dried with anhydrous $Na_2SO_4$. After spin-dried, it was passed through a 200-300 silica gel column (EtOAc) to obtain AST-2-A6 (50 mg, with a content of 70% and a yield of 31.4%) as a yellow solid.

Under the protection of nitrogen, 2-A6 (30 mg, 0.038 mmol, 1 eq.), $Ag_2O$ (44 mg, 0.191 mmol, 5 eq.) and DIEA (26 mg, 0.191 mmol, 5 eq.) were added into THF (1 ml), heated to 65° C. and refluxed. The reaction was complete in 2 h. After cooled to room temperature, the system was filtered with suction through silica gel, and washed with THF. After the mother liquor was spin-dried, it was separated through neutral preparative liquid chromatography, extracted with DCM, spin-dried and lyophilized to obtain Compound No. 2 (6 mg, yield=25.2%) as a brown solid. $^1$H-NMR (400M, MeOD): δ 8.34 (d, J=8.4 Hz, 1H), 7.50 (d, J=8.8 Hz, 2H), 7.45-7.43 (m, 1H), 7.30 (s, 1H), 7.08 (d, J=8.8 Hz, 2H), 5.38 (s, 2H), 5.25 (d, J=7.6 Hz, 2H), 3.10 (s, 3H), 3.05 (s, 3H), 2.20-2.15 (m, 8H). LCMS: Calculated 624.1, found 625.2 ([M+H]$^+$).

Synthesis of Compound No. 3

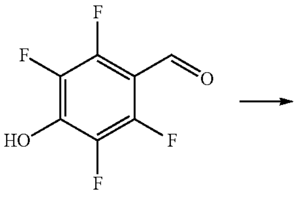

3-A0

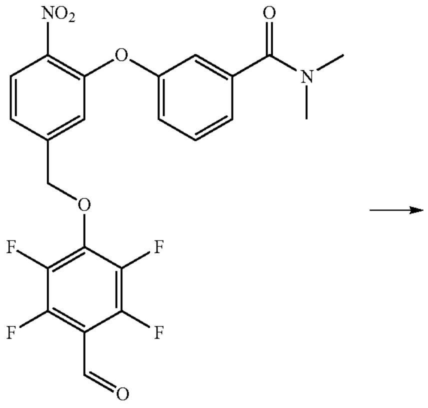

3-A1

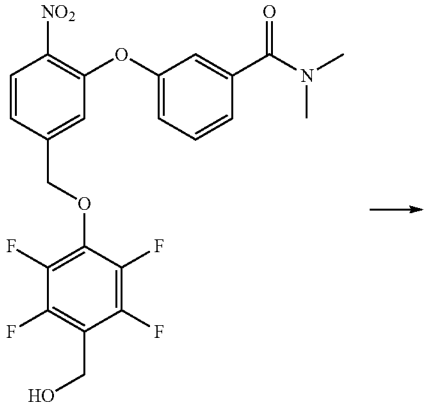

3-A2

-continued

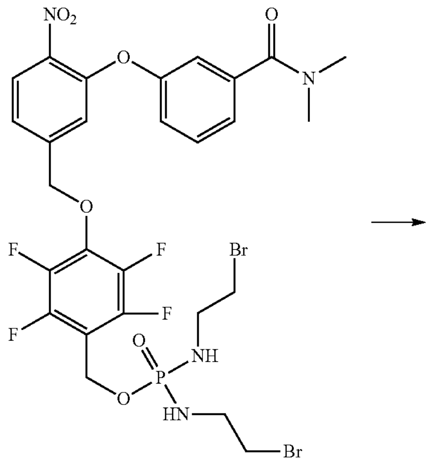

3-A3

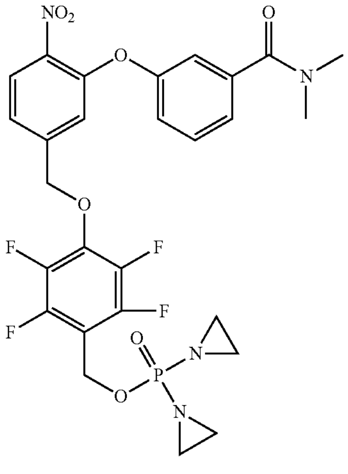

3

Under the protection of nitrogen, 3-B1 (500 mg, 1.49 mmol,

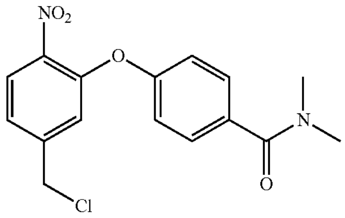

),

3-A0 (1.45 g, 7.470 mmol, 5 eq.) and DIEA (965 mg, 7.470 mmol, 5 eq.) were added to DMF (10 ml) and heated to 50° C. overnight. The conversion of the reaction no longer increased after reaching about 50%. After cooling down to room temperature, $H_2O$ (20 ml) was added and extraction was performed with EtOAc (20 ml×3). The organic phase was washed with water (15 ml×5), and washed with saturated brine (15 ml×3). The organic phase was dried and spin-dried, and passed through a 200-300 silica gel column (PE:EtOAc=3:1) to obtain 3-A1 (295 mg, yield=40.1%) as a light yellow solid. $^1$H-NMR (400M, $CDCl_3$): δ ppm 10.22 (s, 1H), 8.00 (d, J=8.4 Hz, 1H), 7.46-7.42 (m, 1H), 7.30 (d, J=8.4 Hz, 1H), 7.26-7.24 (m, 1H), 7.10-7.08 (m, 3H), 5.37 (s, 2H), 3.11 (s, 3H), 2.99 (s, 3H). LCMS: Calculated 492.1, found 493.1 ([M+H]$^+$).

Under the protection of nitrogen, 3-A1 (290 mg, 0.589 mmol) was dissolved in THF (3 ml) before the temperature was reduced to 0° C. Then, $NaBH_4$ (45 mg, 1.178 mmol, 2 eq.) was added to the system in batches, and the reaction was complete in 30 min. $H_2O$ (5 ml) was added dropwise to the system and extraction was performed with DCM (10 ml×3). The organic phase was washed with water (10 ml×3), and the organic phase was dried and spin-dried and passed through a column (PE:EtOAc=1:1) to obtain 3-A2 (m=100 mg, yield=35.0%) as a yellow solid. $^1$H-NMR (400M, $CDCl_3$): δ ppm 7.99 (d, J=8.4 Hz, 1H), 7.44 (t, J=8.4 Hz, 1H), 7.31 (d, J=7.6 Hz, 1H), 7.22 (d, J=7.6 Hz, 1H), 7.13 (dd, d, J=8.0, 1.6 Hz, 1H), 7.05 (s, 1H), 6.91 (s, 1H), 5.24 (s, 2H), 4.73 (s, 2H), 3.02 (m, 6H). LCMS: Calculated 494.1, found 495.1 ([M+H]$^+$).

Under the protection of nitrogen, $POCl_3$ (61 mg, 0.202 mmol) was dissolved in DCM (2 ml) and then cooled to −40° C. Then, 3-A2 (50 mg, 0.101 mmol) and TEA (26 mg, 0.253 mmol, 2.5 eq.) were added to the system, and held at −40° C. for 6 h until the completion of the reaction. 1-Bromoethylamine hydrobromide (169 mg, 0.81 mmol) was added to the system, and then TEA (82 mg, 0.809 mmol, 8 eq.) was added dropwise to the system. After completion, the temperature was kept at −40° C. for 30 min before the completion of the reaction. After the temperature was increased to room temperature, $NH_4Cl$ solution (10 ml) was added dropwise and extraction was performed with DCM (8 ml×3). The organic phase was washed with water (5 ml×3), and the organic phase was dried and spin-dried, and passed through a 200-300 silica gel column (EtOAc) to obtain 3-A3 (62 mg, 80.0%, with a content of 70%) as a yellow solid, which was used in the subsequent step.

Under the protection of nitrogen, 3-A3 (60 mg, 0.08 mmol, 1 eq.), $Ag_2O$ (88 mg, 0.382 mmol, commercially available) and DIEA (49 mg, 0.38 mmol) were added into THF (2 ml), heated to 65° C. and refluxed. The reaction was complete in 2 h. After cooled to room temperature, the system was filtered with suction through silica gel, and washed with THF. The mother liquor was spin-dried, prepared, extracted with DCM, spin-dried and lyophilized to obtain Compound No. 3 (10 mg, yield=12%) as a brown solid. $^1$H-NMR (400M, MeOD): δ 8.03 (d, J=8.4 Hz, 1H), 7.51 (t, J=8.0 Hz, 1H), 7.43 (d, J=8.0 Hz, 1H), 7.28-7.25 (m, 2H), 7.13-7.10 (m, 2H), 5.37 (s, 2H), 5.25 (d, J=7.6 Hz, 2H), 3.09 (s, 3H), 3.00 (s, 3H), 2.21-2.16 (m, 8H). LCMS: Calculated 624.1, found 625.1 ([M+H]$^+$).

Synthesis of Compound No. 4

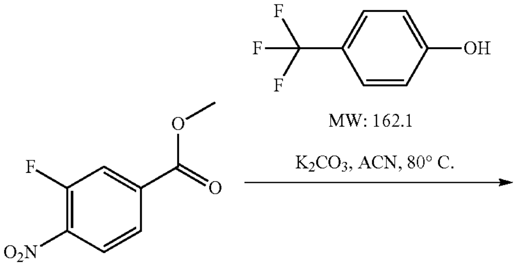

4-A1

-continued

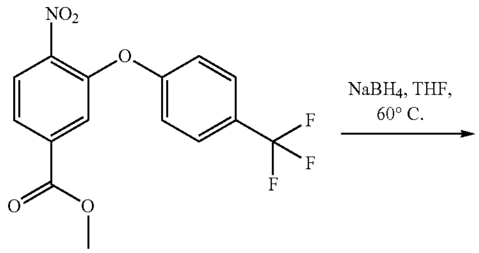

4-A2

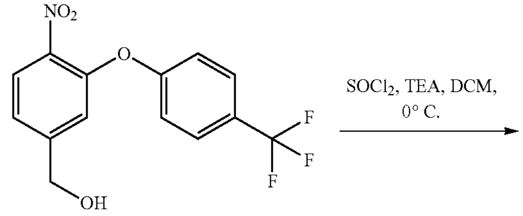

4-A3

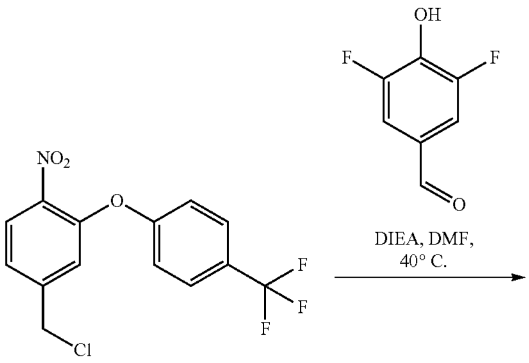

4-A4

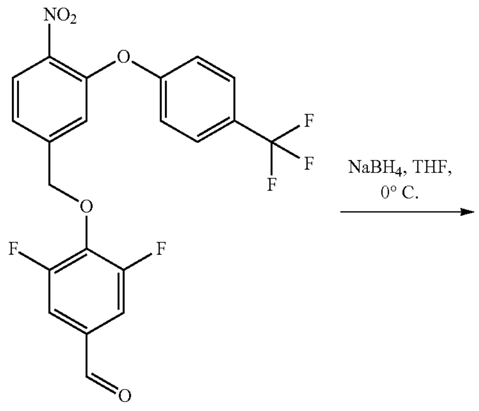

4-A5

-continued

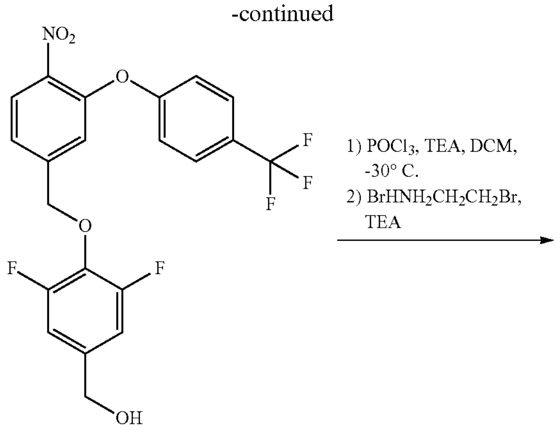

4-A6

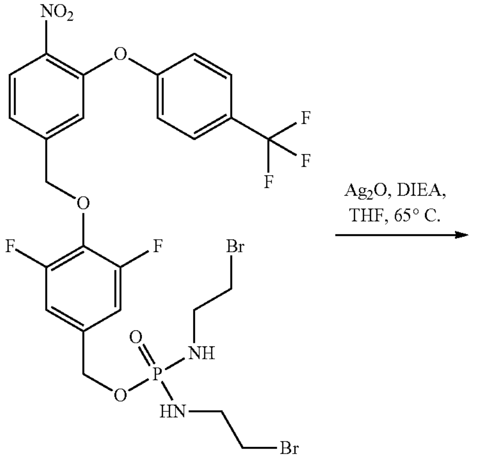

4-A7

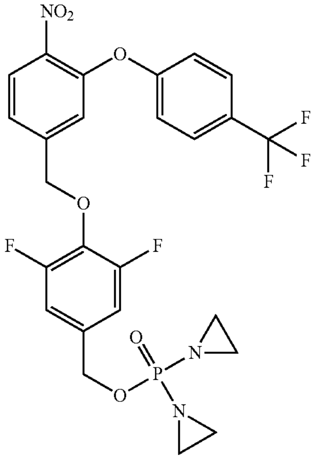

4

Under the protection of nitrogen, 4-A1 (3.7 g, 18.45 mmol) and p-trifluoromethylphenol (2 g, 12.3 mmol, commercially available) were dissolved in ACN (30 mL). $K_2CO_3$ (3.4 g, 24.6 mmol) was added, heated to 80° C. and stirred overnight. After the completion of the reaction, the system was subjected to suction filtration through Celite®), and concentrated to obtain the crude product 4-A2 (5.6 g, 97.2%) as a yellow solid, which was directly used in the subsequent step. $^1$H-NMR (400M, $CDCl_3$): δ ppm 8.03-7.95 (mi, 2H), 7.76 (d, J=1.6 Hz, 1H), 7.66 (d, J=8.8 Hz, 2H), 7.11 (d, J=8.8 Hz, 2H), 3.94 (s, 3H). LCMS: Calculated 341.1, found 342.1 ([M+H]$^+$).

Under the protection of nitrogen, 4-A2 (1.6 g, 4.7 mmol) was dissolved in THF (30 mL). $NaBH_4$ (1.4 g, 37.6 mmol) was added in batches, heated to 60° C. and stirred overnight. After the completion of the reaction, the temperature was reduced to 5° C., and saturated $NH_4Cl$ aqueous solution (15 mL) was added dropwise. Extraction was performed with DCM (20 ml) followed by washing with water (4×5 mL), drying, and concentration to obtain the crude product 4-A3 (1.6 g) as a yellow oily liquid, which was directly used in the subsequent step. $^1$H-NMR (400M, $CDCl_3$): δ ppm 8.02 (d, J=8.4 Hz, 1H), 7.62 (d, J=8.8 Hz, 2H), 7.31-7.28 (m, 1H), 7.15 (s, 1H), 7.08 (d, J=8.4 Hz, 2H), 4.77 (s, 2H), 1.86 (s, 1H). LCMS: Calculated 313.1, found 314.0342.1 ([M+H]$^+$).

Under the protection of nitrogen, the crude product 4-A3 (600 mg, 1.92 mmol) in the above step was dissolved in ultra-dry DCM (10 mL). The temperature was reduced to 0° C. and $SOCl_2$ (457 mg, 3.84 mmol) was slowly added dropwise. After 1 h, additional 1 eq. of TEA (194 mg, 1.92 mmol) was added, and the reaction was complete in 30 min. The temperature was reduced and saturated $NaHCO_3$ solution (10 mL) was added dropwise. Extraction was performed with DCM (15 mL×2) followed by washing with water (5 mL×3), drying, and concentration to obtain the crude product 4-A4 (580 mg) as a light yellow liquid, which was directly used in the subsequent step.

Under the protection of nitrogen, 4-A4 (580 mg, 1.75 mmol) and

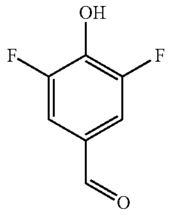 [SMILES: O=Cc1cc(F)c(O)c(F)c1]

(692 mg, 4.375 mmol) were dissolved in DMF (10 ml), and then DIEA (1.4 g, 10.5 mmol) was added, and reaction was performed overnight at 40° C. After the completion of the reaction, extraction was performed with EA (15 mL×2) followed by washing with water (5 mL×6), drying, concentration and column separation (200-300 mesh silica gel, N-heptane:EA=10:1 to 5:1) to obtain the product 4-A5 (300 mg, 55.0%) as a yellow oily liquid. $^1$H-NMR (400M, $CDCl_3$): δ ppm 9.84-9.85 (m, 1H), 8.04 (d, J=8.4 Hz, 1H), 7.64 (d, J=8.8 Hz, 2H), 7.46 (d, J=8.2 Hz, 2H), 7.38 (d, J=8.4 Hz, 1H), 7.21 (s, 1H), 7.09 (d, J=8.4 Hz, 2H), 5.32 (s, 2H).

Under the protection of nitrogen, 4-A5 (300 mg, 0.66 mmol) was dissolved in THF (6 mL). The temperature was reduced to 0° C. $NaBH_4$ (50 mg, 1.32 mmol, commercially available) was added in batches. The reaction was complete in 30 min. Saturated $NH_4Cl$ solution (5 mL) was added dropwise at 0° C. Extraction was performed with DCM (15 mL×2) followed by washing with water (5 mL×3), drying, concentration and column separation (200-300 mesh silica gel, Heptane:EA=10:1 to 5:1) to obtain the product 4-A6 (190 mg, 90.6%) as a light yellow solid. $^1$H-NMR (400M, $CDCl_3$): δ ppm 8.02 (d, J=8.4 Hz, 1H), 7.63 (d, J=8.4 Hz, 2H), 7.36-7.38 (m, 1H), 7.23 (s, 1H), 7.07 (d, J=8.4 Hz, 2H), 6.90 (d, J=8.8 Hz, 2H), 5.17 (s, 2H), 4.63 (s, 2H).

Under the protection of nitrogen, $POCl_3$ (130 mg, 0.84 mmol, commercially available) was dissolved in ultra-dry DCM (5 mL). The temperature was reduced to −30° C. A DCM (5 ml) solution of 4-A6 (190 mg, 0.42 mmol) was added dropwise, then TEA (106 mg, 1.05 mmol) was added dropwise, and the temperature was kept at −30° C. for 6 h until the raw materials disappeared completely. 2-Bromoethylamine hydrobromide (688 mg, 3.36 mmol) was added at −30° C., and then TEA (340 mg, 3.36 mmol) was added dropwise. After the completion of the reaction, the temperature was reduced to 0° C., and saturated $NH_4Cl$ solution (10 mL) was added. Extraction was performed with DCM (15 mL×2) followed by washing with water (5 mL×4), drying, concentration and column separation (200-300 mesh silica gel, Heptane:EA=1:2 to EA) to obtain the product (120 mg, yield=57.6%) as a yellow solid. $^1$H-NMR (400M, $CDCl_3$): δ ppm 8.03 (d, J=8.4 Hz, 1H), 7.64 (d, J=8.8 Hz, 2H), 7.37 (d, J=8.0 Hz, 1H), 7.24 (s, 1H), 7.08 (d, J=8.4 Hz, 2H), 6.95 (d, J=8.4 Hz, 2H), 5.18 (s, 2H), 4.94 (d, J=8.4 Hz, 2H), 3.14-3.46 (m, 4H), 3.33 (m, 4H), 3.14 (m, 2H). LCMS: Calculated 747.0, found 748.0 ([M+H]$^+$).

Under the protection of nitrogen, 4-A7 (120 mg, 0.16 mmol) was dissolved in THF (10 mL), and $Ag_2O$ (222 mg, 0.96 mmol, commercially available) and N,N-diisopropylethylamine (124 mg, 0.96 mmol, commercially available) were added. The temperature was increased to 65° C. to carry out the reaction. The reaction was complete in 2 h. After that, suction filtration was performed through Celite®. The solid was washed with DCM (20 mL), the mother liquor was concentrated, and a pure product (14.3 mg, 28.4%) was obtained as a yellow waxy solid by high-performance liquid chromatography. $^1$H-NMR (400M, $CDCl_3$): δ ppm 8.02 (d, J=8.4 Hz, 1H), 7.64 (d, J=8.8 Hz, 2H), 7.37 (d, J=8.4 Hz, 1H), 7.24 (s, 1H), 7.08 (d, J=8.8 Hz, 2H), 6.96 (d, J=8.4 Hz, 2H), 5.18 (s, 2H), 5.06 (d, J=8.4 Hz, 2H), 2.13-2.23 (m, 8H). LCMS: Calculated 585.1, found 586.1 ([M+H]$^+$).

Synthesis of Compound No. 5

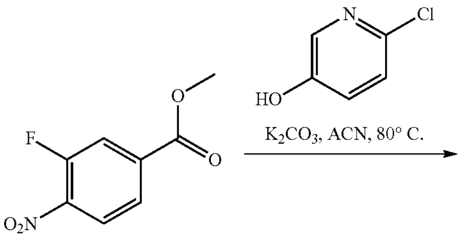

5-A1

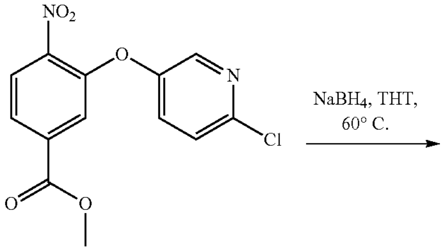

5-A2

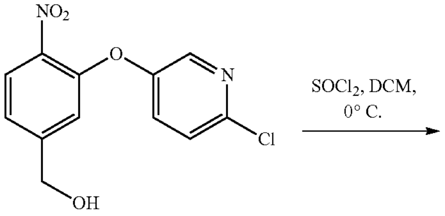

5-A3

-continued

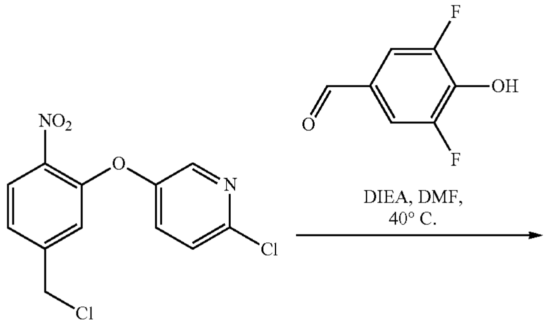

5-A4

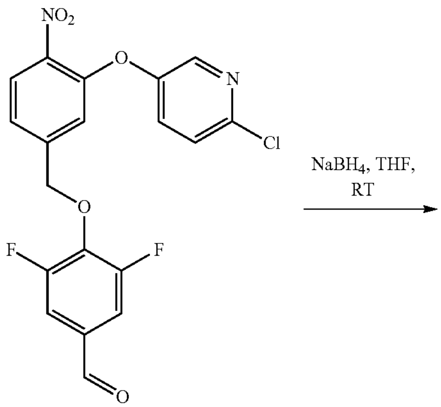

5-A5

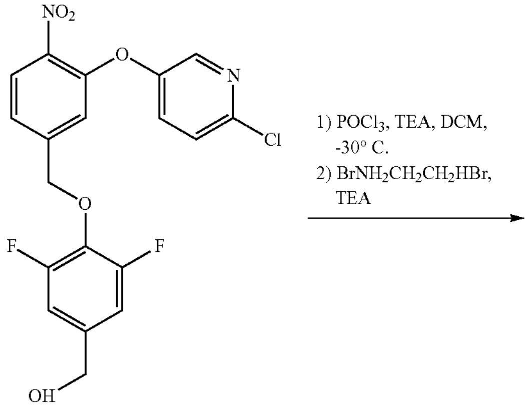

5-A6

-continued

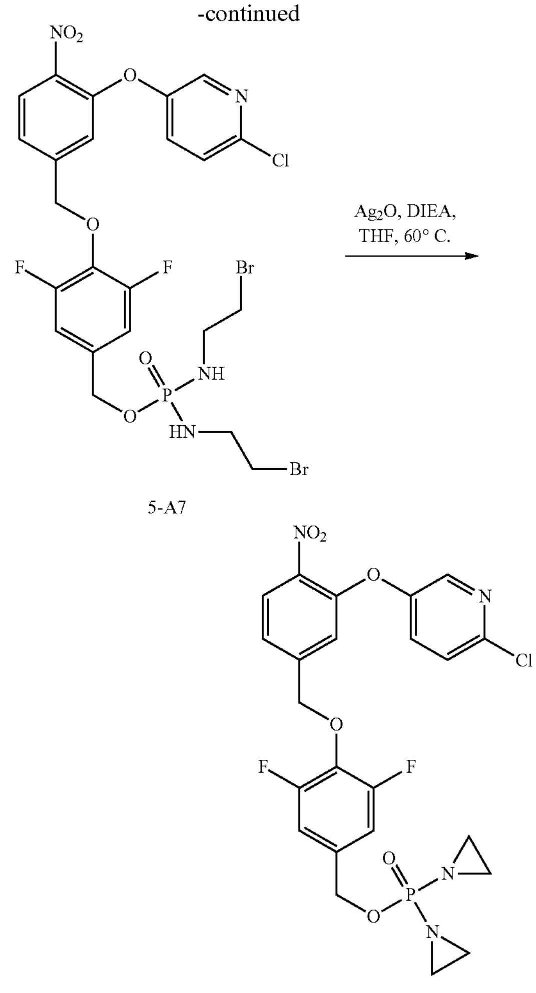

5-A7

5

Under the protection of nitrogen, 5-A1 (5.8 g, 28.9 mmol) and 2-chloro-5-hydroxypyridine (2.5 g, 19.3 mmol) were dissolved in acetonitrile (50 mL). After potassium carbonate (5.3 g, 38.6 mmol) was added, the temperature was increased to 80° C. and stirring was performed overnight. After the completion of the reaction, suction filtration was performed through Celite®. The mother liquor was concentrated, slurried with n-heptane, and filtered with suction to give the pure product 5-A2 (5.7 g, 95.7%) as a light yellow solid. $^1$H-NMR (400M, $CDCl_3$): ppm 8.20 (s, 1H), 7.94-8.03 (m, 2H), 7.69 (s, 1H), 7.37 (s, 2H), 3.93 (s, 3H). LCMS: Calculated 308.0, found 309.0 ([M+H]+) Under the protection of nitrogen, 5-A2 (2 g, 6.5 mmol) was dissolved in THF (30 mL), then $NaBH_4$ (1.97 g, 52 mmol) was added in batches. The temperature was increased to 60° C. and stirring was performed overnight. After the completion of the reaction, the temperature was reduced and saturated $NH_4Cl$ aqueous solution (15 mL) was added dropwise. Extraction was performed with DCM (20 mL) followed by washing with water (4×5 mL), drying, concentration and column separation (200-300 mesh silica gel, n-heptane: EA=5:1 to 1:1) to obtain the product 5-A3 (m=800 mg, yield=44.4%) as a light yellow solid. $^1$H-NMR (400M, $CDCl_3$): ppm 8.16 (s, 1H), 8.02 (d, J=8.4 Hz, 1H), 7.34 (s, 2H), 7.29 (d, J=8.4 Hz, 1H), 7.12 (s, 1H), 4.77 (s, 2H), 1.84 (s, 1H). LCMS: Calculated 280.0, found 281.0 ([M+H]$^+$).

Under the protection of nitrogen, 5-A3 (800 mg, 2.85 mmol) was dissolved in ultra-dry DCM (10 ml). The temperature was reduced to 0° C., and $SOCl_2$ (1.19 g, 9.98 mmol) was slowly added dropwise. The reaction was complete in 4 h. The temperature was reduced and saturated $NaHCO_3$ solution (10 mL) was added dropwise. Extraction was performed with DCM (15 mL×3). The organic phase was washed with $NaHCO_3$ solution (5 mL×2), dried, and concentrated to obtain the product 5-A4 (440 mg, a light yellow liquid, 51.6%), which was used directly in the next step.

Under the protection of nitrogen, 5-A4 (440 mg, 1.47 mmol) and

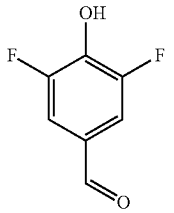 [SMILES: O=Cc1cc(F)c(O)c(F)c1]

(581 mg, 3.675 mmol) were dissolved in DMF (10 ml), and then DIEA (1.14 g, 8.82 mmol) was added. The reaction was performed overnight. After the completion of the reaction, extraction was performed with EA (15 mL×2) followed by washing with water (5 mL×6), drying, concentration and column separation (200-300 mesh silica gel, n-heptane: EA=10:1 to 5:1) to obtain the product 5-A5 (m=340 mg, yield=55.0%) as a yellow oily liquid. $^1$H-NMR (400M, $CDCl_3$): ppm 9.85 (t, J=1.6 Hz, 1H), 8.16 (d, J=1.2 Hz, 1H), 8.03 (d, J=8.4 Hz, 1H), 7.46 (d, J=8.0 Hz, 2H), 7.34-7.38 (m, 3H), 7.18 (s, 1H), 5.32 (s, 2H). LCMS: Calculated 420.0, found 421.0 ([M+H]$^+$).

Under the protection of nitrogen, 5-A5 (340 mg, 0.81 mmol) was dissolved in THF (6 mL). The temperature was reduced to 0° C., and sodium borohydride (61 mg, 1.62 mmol) was added in batches. The reaction was complete in 30 min. Saturated $NH_4Cl$ solution (5 mL) was added dropwise at 0° C. Extraction was performed with DCM (10 mL×2) followed by washing with water (5 mL×3), drying, and concentration to obtain the product 5-A6 (310 mg, a light yellow solid, 90.6%), which was used directly in the next step. $^1$H-NMR (400M, DMSO-$d_6$): ppm 8.03 (d, J=8.4 Hz, 1H), 7.55 (d, J=2.8 Hz, 1H), 7.46-7.34 (m, 2H), 7.01 (d, J=1.2 Hz, 1H), 6.90-6.87 (m, 2H), 5.17 (s, 2H), 4.61 (d, J=6.4 Hz, 2H). LCMS: Calculated 422.0, found 423.0 ([M+H]$^+$).

Under the protection of nitrogen, phosphorus oxychloride (224 mg, 1.46 mmol) was added dropwise to ultra-dry DCM (5 mL). The temperature was reduced to −30° C. DCM (5 ml) solution of 5-A6 (310 mg, 0.73 mmol) was added dropwise, then triethylamine (185 mg, 1.825 mmol) was added dropwise, and the temperature was kept at −30° C. for 5 h until the raw materials disappeared completely. 2-Bromoethylamine hydrobromide (1.2 g, 5.84 mmol) was added at −30° C., and then triethylamine (591 mg, 5.84 mmol) was added dropwise. After the completion of the reaction, extraction was performed with DCM (15 mL×2) followed by washing with water (5 mL×4), drying, concentration and column separation (200-300 mesh silica gel) to obtain the product 5-A4 (300 mg, yield=57.6%) as a light yellow oil. $^1$H-NMR (400M, $CDCl_3$): ppm 8.10 (s, 1H), 8.00 (d, J=8.4 Hz, 1H), 7.34-7.35 (m, 3H), 7.18 (s, 1H), 6.93 (d, J=8.4 Hz, 2H), 5.29 (s, 2H), 5.17 (s, 2H), 4.92 (d, J=8.4 Hz, 2H), 3.42-3.48 (m, 4H), 3.29-3.36 (m, 4H), 3.20-3.22 (m, 2H). LCMS: Calculated 713.9, found 714.9 ([M+H]$^+$).

Under the protection of nitrogen, 5-A7 (300 mg, 0.42 mmol) was dissolved in THF (10 mL), and silver oxide (584 mg, 2.52 mmol, commercially available) and N,N-diisopropylethylamine (326 mg, 2.52 mmol) were added. The temperature was increased to 60° C. to carry out the reaction. The reaction was complete in 2.5 h. After that, suction filtration through Celite® was performed. The solid was washed with DCM (20 mL), the mother liquor was concentrated, and pure Compound No. 5 (66 mg, 28.4%) was obtained as a light yellow solid by high-performance liquid preparative chromatography. $^1$H-NMR (400M, $CDCl_3$): ppm 8.16 (d, J=2.4 Hz, 1H), 8.02 (d, J=8.4 Hz, 1H), 7.31-7.37 (m, 3H), 7.20 (s, 1H), 6.96 (d, J=8.4 Hz, 2H), 5.17 (s, 2H), 5.06 (d, J=8.0 Hz, 2H), 2.24-2.14 (m, 8H). LCMS: Calculated 552.1, found 553.1 ([M+H]+).

Synthesis of Compound No. 6

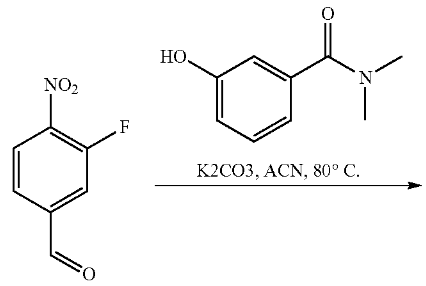

6-A1

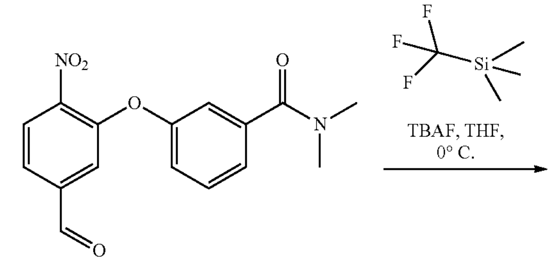

6-A2

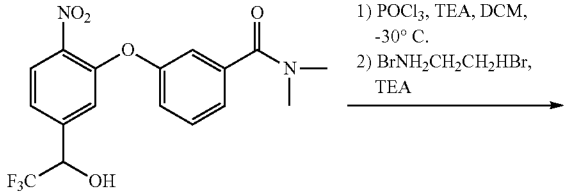

6-A3

-continued

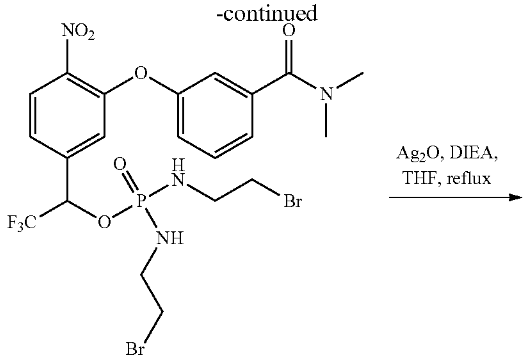

6-A4

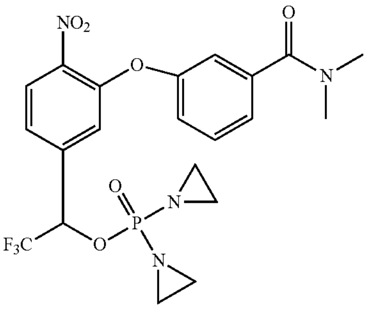

6

Under the protection of nitrogen, 6-A1 (1.5 g, 9.15 mmol, commercially available) and

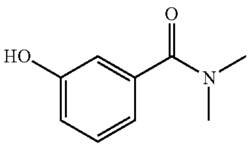

(1 g, 6.10 mmol) were dissolved in acetonitrile (20 mL). The temperature was increased to 80° C. and the reaction was complete in 5 h. The temperature was reduced to room temperature, suction filtration through Celite® was performed, and the filter cake was washed with EA The mother liquor was concentrated, and isolated by silica gel column (200-300 mesh silica gel, Heptane:EA=2:1 to 1:1) to obtain the product 6-A2 (1.2 g, yield=63.2%) as a light yellow oily liquid. $^1$H-NMR (400M, $CDCl_3$): δ ppm 9.96 (s, 1H), 8.04 (d, J=8.2 Hz, 1H), 7.73 (dd, J=8.2, 1.5 Hz, 1H), 7.51 (d, J=1.4 Hz, 1H), 7.49-7.43 (m, 1H), 7.35-7.27 (m, 1H), 7.14 (dd, J=7.9, 1.3 Hz, 2H), 3.09 (s, 3H), 2.99 (s, 3H). LCMS: Calculated 314.1, found 315.1 ([M+H]$^+$).

Under the protection of nitrogen, 6-A2 (550 mg, 1.75 mmol) was dissolved in THF (10 ml), and (trifluoromethyl)-trimethylsilane (373 mg, 2.62 mmol) was added. The temperature was reduced to 0° C., and tetrabutylammonium fluoride (0.04 mL, 0.04 mmol, 1 MinTHF) was added dropwise. After 2 hours, 3N hydrochloric acid (0.5 mL) was added dropwise. Extraction was performed with DCM (10 mL×2) followed by washing with $NaHCO_3$ solution (5 mL×3), washing with water, washing with brine, drying, and concentration to obtain 600 mg of the crude product 6-A3 as a light yellow oily liquid, which was directedly used in the next step.

Under the protection of nitrogen, phosphorus oxychloride (376 mg, 2.45 mmol) was added to ultra-dry DCM (15 ml).

The temperature was reduced to −30° C. DCM solution (5 mL) of 6-A3 (470 mg, 1.22 mmol, crude) was added dropwise, then triethylamine (312 mg, 3.03 mmol) was added dropwise, and the temperature was kept at −30° C. for 4 h until the raw materials were completely converted. 2-Bromoethylamine hydrobromide (2.0 g, 9.78 mmol) was added at −30° C., and then triethylamine (940 mg, time 9.78 mmol) was added dropwise. The temperature was kept at −30° C. The reaction was complete in 1 h. At 0° C., saturated ammonium chloride aqueous solution (8 mL) was added dropwise. Extraction was performed with dichloromethane (15 mL×2) followed by washing with water, drying, concentration and column separation (200-300 mesh silica gel, PE:EA=1:2-EA) to obtain the product 6-A4 (440 mg, yield=53.4%) as a yellow oily liquid. $^1$H-NMR: 6 ppm 7.98 (d, J=8.3 Hz, 1H), 7.49-7.46 (m, 1H), 7.29-7.21 (m, 4H), 7.07 (s, 1H), 5.71-5.67 (m, 1H), 3.46-3.12 (m, 10H), 3.07 (s, 3H), 2.99 (s, 3H). MS: Calculated MS: 676.0, found: 677.0 ([M+1]+).

Under the protection of nitrogen, 6-A4 (440 mg, 0.65 mmol) was dissolved in THF (25 mL), silver oxide (910 mg, 3.92 mmol) was added and then DIEA (510 mg, 3.92 mmol) were added. The temperature was increased to 65° C. The reaction was complete in 2 h. The temperature was reduced to room temperature. Suction filtration through Celite® was performed. The solid was washed with DCM, the mother liquor was concentrated, and pure Compound No. 6 (90.0 mg, 27%) was obtained as a white solid by high-performance liquid preparative chromatography. $^1$H-NMR (400M, $CDCl_3$): δ ppm 8.00 (d, J=8.4 Hz, 1H), 7.52-7.32 (m, 2H), 7.26-7.23 (m, 2H), 7.08-7.06 (m, 2H), 5.72 (dq, J=12.2, 6.1 Hz, 1H), 3.09 (s, 3H), 2.97 (s, 3H), 2.32-1.89 (m, 8H). LCMS: Calculated 514.1, found 515.1 [(M+H)+].

Synthesis of Compound No. 7

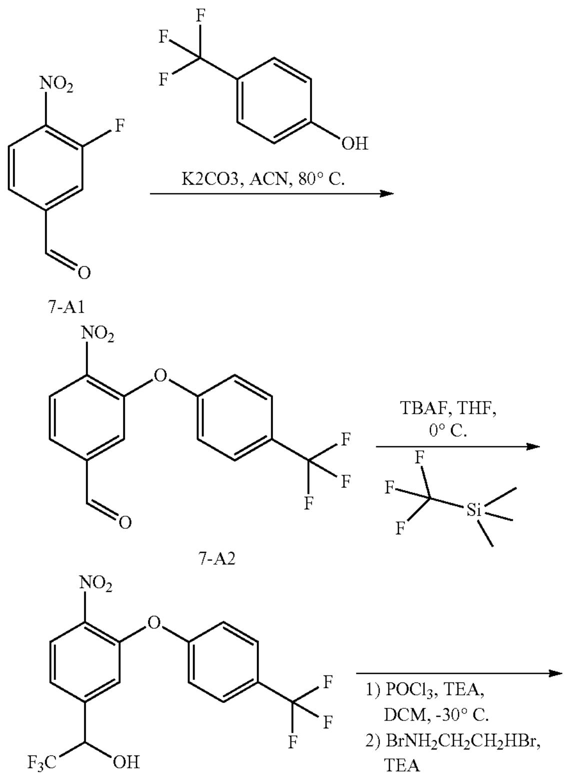

7-A1
7-A2
7-A3

-continued

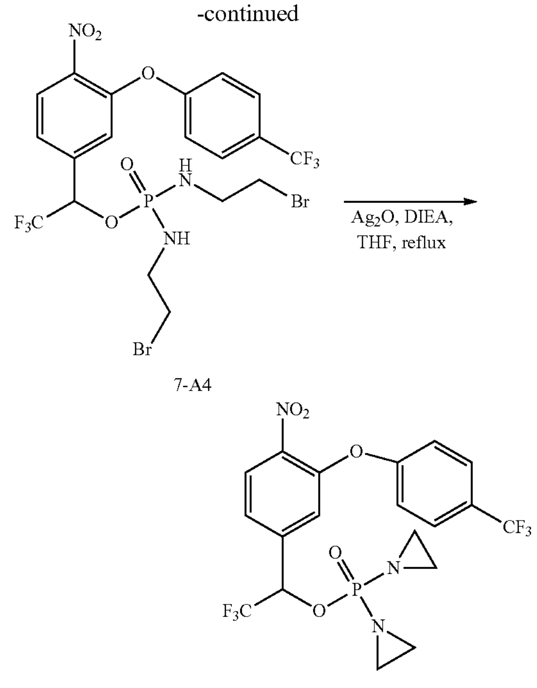

7-A4
7

Under the protection of nitrogen, 7-A1 (1.5 g, 9.15 mmol, commercially available) and p-trifluoromethylphenol (990 mg, 6.10 mmol) were dissolved in acetonitrile (20 mL). Potassium carbonate (1.7 g, 12.2 mmol, commercially available) was added. The temperature was increased to 80° C. and the reaction was complete in 2.5 h. The temperature was reduced to room temperature, suction filtration through Celite®) was performed, and the filter cake was washed with EA. The mother liquor was concentrated, and column separation (200-300 mesh silica gel, Heptane:EA=5:1 to 1:1) to obtain the product 7-A2 (1.1 g, yield=38.6%) as a light yellow solid. $^1$H-NMR (400M, $CDCl_3$): δ ppm 10.01 (s, 1H), 8.09 (d, J=8.2 Hz, 1H), 7.79 (dd, J=8.2, 1.6 Hz, 1H), 7.68 (d, J=8.6 Hz, 2H), 7.57 (d, J=1.5 Hz, 1H), 7.15 (d, J=8.6 Hz, 2H).

Under the protection of nitrogen, 7-A2 (400 mg, 1.29 mmol) was dissolved in THF (10 mL), and (trifluoromethyl)-trimethylsilane (274 mg, 1.93 mmol)) was added. The temperature was reduced to 0° C., and tetrabutylamimonium fluoride (0.04 mL, 0.04 mmol, 1 mol/L THF solution) was added dropwise. After 2 hours, 3N hydrochloric acid (0.5 mL) was added dropwise. Extraction was performed with DCM (10 mL×2) followed by washing with $NaHCO_3$ solution (5 mL×3), washing with water, washing with brine, drying, and concentration to obtain 450 mg of the crude product 7-A3 as a light yellow oily liquid, which was directedly used in the next step. $^1$H-NMR (400M, $CDCl_3$): δ ppm 8.04 (d, J=7.8 Hz, 1H), 7.64 (d, J=7.9 Hz, 2H), 7.45 (d, J=7.7 Hz, 1H), 7.30 (s, 1H), 7.09 (d, J=8.0 Hz, 2H), 5.09 (s, 1H), 3.26 (s, 1H). LCMS: Calculated 381.2, found 382.0 ([M+1]+).

Under the protection of nitrogen, phosphorus oxychloride (362 mg, 2.36 mmol) was added to ultra-dry DCM (15 ml). The temperature was reduced to −30° C. DCM solution (5 mL) of 7-A3 (450 mg, 1.18 mmol, crude) was added dropwise, then triethylamine (300 mg, 2.95 mmol) was added dropwise, and the temperature was kept at −30° C. for 4 h until the raw materials were completely converted.

2-Bromoethylamine hydrobromide (1.9 g, 9.44 mmol) was added at −30° C., and then triethylamine (960 mg, 9.44 mmol) was added dropwise. The temperature was kept at −30° C. the reaction was complete in 1 h. At 0° C., saturated ammonium chloride aqueous solution (6 mL) was added dropwise. Extraction was performed with DCM (15 mL×2) followed by washing with water, drying, concentration and column separation (200-300 mesh silica gel, Heptane: EA=1:1 to 0:1) to obtain the product 7-A4 (440 mg, 55.4%) as a yellow oily liquid. $^1$H-NMR (400 MHz, $CDCl_3$): δ ppm 8.05 (d, J=8.4 Hz, 1H), 7.65 (d, J=8.6 Hz, 2H), 7.44 (d, J=8.5 Hz, 1H), 7.23 (s, 1H), 7.10 (d, J=8.5 Hz, 2H), 5.72-5.64 (m, 1H), 3.40-3.10 (m, 10H). LCMS: Calculated 672.9, found 673.9 ([M+1]$^+$).

Under the protection of nitrogen, 7-A4 (400 mg, 0.59 mmol) was dissolved in THF (25 mL), silver oxide (826 mg, 3.57 mmol) was added and then DIEA (461 mg, 3.57 mmol) were added. The temperature was increased to 65° C. The reaction was complete in 2 h. The temperature was reduced to room temperature. Suction filtration through Celite® was performed. The solid was washed with DCM, the mother liquor was concentrated, and pure Compound No. 7 (68 mg, yield=22.5%) was obtained as a white solid by high-performance liquid preparative chromatography. $^1$H-NMR (400M, $CDCl_3$): δ ppm 8.05 (d, J=8.5 Hz, 1H), 7.65 (d, J=8.6 Hz, 2H), 7.45 (d, J=8.5 Hz, 1H), 7.27 (s, 1H), 7.09 (d, J=8.5 Hz, 2H), 5.75 (d, J=4.4 Hz, 1H), 2.33-1.98 (m, 8H). LCMS: Calculated LCMS: 511.1, found 512.0 ([M+H]$^+$).

Synthesis of Compound No. 8

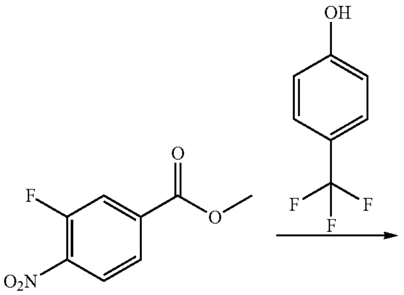

8-A1

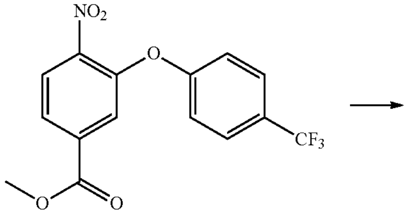

8-A2

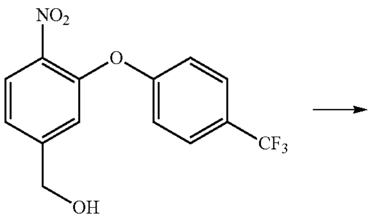

8-A3

-continued

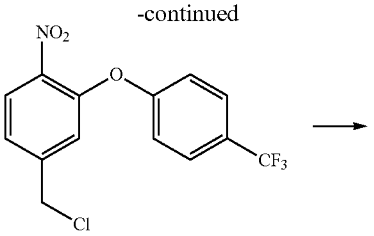

8-A4

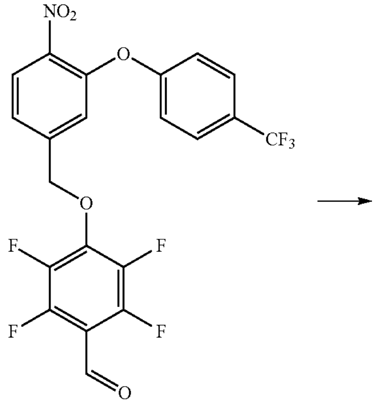

8-A5

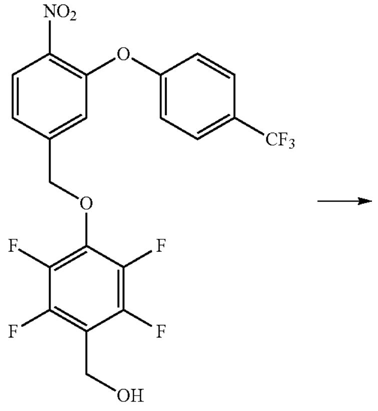

8-A6

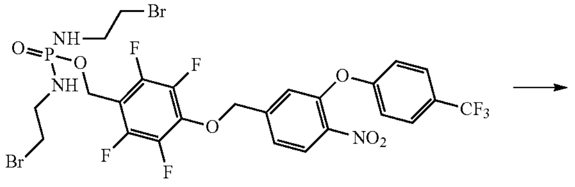

8-A7

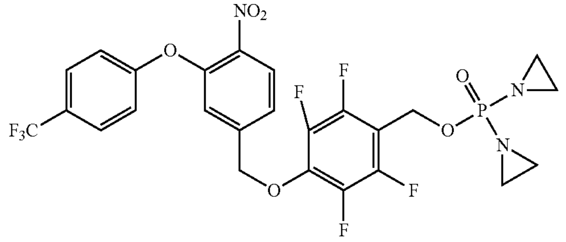

8

8-A1 (5.5 g, 27.6 mmol) and p-trifluoromethylphenol (3.0 g, 18.5 mmol, commercially available) were dissolved in acetonitrile (30 mL). $K_2CO_3$ (5.1 g, 37.0 mmol, commercially available) was added. The temperature was increased to 80° C. and stirring was performed overnight before the completion of the reaction. The temperature was naturally reduced to room temperature, suction filtration through Celite® was performed, and the filter cake was washed with EA (10 ml×3). The mother liquor was concentrated, and the crude product 8-A2 (4.6 g, 72.9%) was obtained as a yellow solid by crystallization from methyl tert-butyl ether. This crude product was directly used in the subsequent reaction.

8-A2 (2.5 g, 7.33 mmol) was dissolved in THF, sodium borohydride (2.2 g, 58.7 mmol, commercially available) was added in batches, and stirring was performed at room temperature for 30 min. The temperature was increased to 65° C., stirring was performed, and the progress of the reaction was monitored. The reaction was complete in 2 h. The system was cooled to 0° C., $H_2O$ (20 ml) was added dropwise, and stirring was performed for 20 min. Extraction was performed with DCM (50 mL×3) followed by washing with water, drying with anhydrous $Na_2SO_4$, and concentration to obtain the crude product 8-A3 (1.5 g, 65.4%) as a light yellow solid.

Under the protection of nitrogen, 8-A3 (1.5 g, 4.79 mmol) was dissolved in DCM (20 ml). The temperature was reduced to 0° C., and $SOCl_2$ (1.1 g, 9.58 mmol) and TEA (485 mg, 4.79 mmol) were added dropwise and stirred. The progress of the reaction was monitored. The reaction was complete in 1 h. At 0° C., saturated $NaHCO_3$ aqueous solution (5 mL) was added dropwise. Extraction was performed with DCM (20 mL×3) followed by washing with $NaHCO_3$ aqueous solution, drying with anhydrous $Na_2SO_4$, and concentration to obtain the crude product 8-A5 (1.3 g, 81.8%) as a reddish brown liquid, which was directedly used in the next step.

8-A4 (220 mg, 0.66 mmol) and 2,3,5,6-tetrafluoro-4-hydroxybenzaldehyde (513 mg, 2.65 mmol) were dissolved in DMF (5 mL). DIEA (430 mg, 3.32 mmol) was added dropwise and stirred. The temperature was increased to 45° C. The progress of the reaction was monitored. The reaction was complete in 3 h. $H_2O$ (10 mL) was added and the temperature was naturally reduced to room temperature. Extraction was performed with EA (8 mL×3) followed by drying with anhydrous $Na_2SO_4$, and concentration to obtain the crude product 8-A5 (70 mg) as a light yellow liquid, which was directedly used in the next step.

8-A5 (70 mg, 0.14 mmol) was dissolved in THF (5 mL). The temperature was reduced to 0° C. $NaBH_4$ (11 mg, 0.37 mmol) was added in batches. The progress of the reaction was monitored. The reaction was complete in 0.5 h. At 0° C., $H_2O$ (3 mL) was added dropwise and stirred for 20 min. Extraction was performed with DCM (10 mL×3) followed by washing with water, drying with anhydrous $Na_2SO_4$, and concentration to obtain 50 mg of the crude product 8-A6 as a light yellow liquid, which was directedly used in the next step.

$POCl_3$ (31 mg, 0.20 mmol, commercially available) was dissolved in DCM (3 mL). The temperature was reduced to −30° C. DCM solution (1 mL) of 8-A6 (50 mg, 0.10 mmol) was added dropwise, and then DCM solution (1 mL) of triethylamine (26 mg, 0.26 mmol) was added dropwise. The temperature was kept at −30° C. to carry out the reaction. The progress of the reaction was monitored. The raw materials disappeared in 2 h. The temperature was reduced to −40° C. 2-Bromoethylamine hydrobromide (167 mg, 0.82 mmol) and TEA (83 mg, 0.82 mmol) were added. The temperature was kept at −40° C. The reaction was complete in 30 min. After the temperature was increased to 5° C., $H_2O$ (5 mL) was added and extraction was performed with DCM (5 mL×3) followed by washing with water (3 mL×2), drying with anhydrous $Na_2SO_4$, concentration, and column chromatography separation (200-300 mesh silica gel, n-heptane: EA=1:1) to obtain the product 8-A7 (50 mg, 62.7%) as a light yellow liquid. 8-A7 (50 mg, 0.064 mmol) was dissolved in THF (5 mL) and $Ag_2O$ (74 mg, 0.32 mmol, commercially available), and DIEA (41 mg, 0.32 mmol) were added. The temperature was increased to 65° C. The progress of the reaction was monitored. The reaction was complete in 1 h. The temperature was reduced to room temperature, suction filtration through Celite® was performed, and the solid was washed with THF (2 ml×3). The mother liquor was concentrated, and a product (2.2 mg, 5.5%) was separated and obtained as a white wax by high-performance liquid chromatography. $^1$H-NMR (400M, $CDCl_3$) δ 8.04 (d, J=8.4 Hz, 1H), 7.65 (d, J=8.6 Hz, 2H), 7.36 (dd, J=8.4, 1.6 Hz, 1H), 7.20 (d, J=1.5 Hz, 1H), 7.09 (d, J=8.5 Hz, 2H), 5.28 (s, 2H), 5.23 (d, J=6.1 Hz, 2H), 2.26-2.15 (m, 8H). LCMS: Calculated 621.1, found 622.1 ($[M+H]^+$).

Synthesis of Compound No. 9

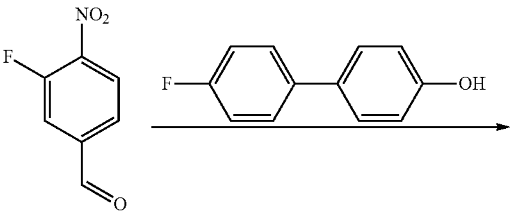

9-A1

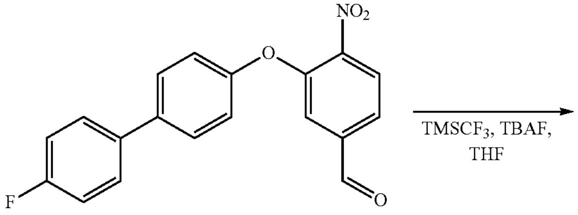

9-A2

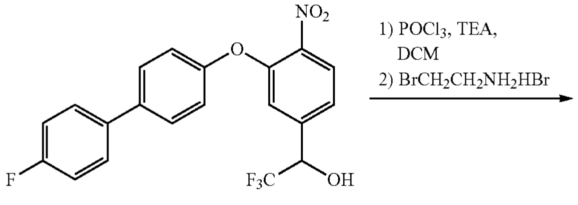

9-A3

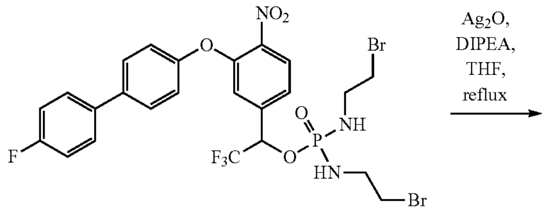

9-A4

-continued

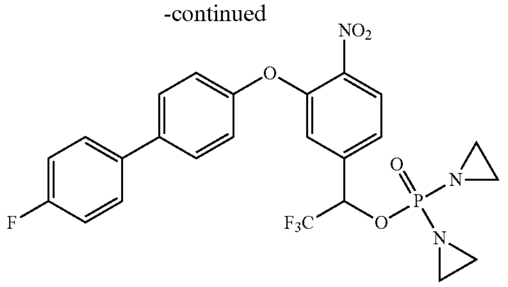

9

Under the protection of nitrogen, 9-A1 (500 mg, 2.97 mmol) and 4-fluoro-4'-hydroxybiphenyl (723 mg, 3.84 mmol, commercially available pharmaceuticals) were dissolved in acetonitrile (10 mL). Potassium carbonate (820 mg, 5.94 mmol, commercially available) was added. The temperature was increased to 85° C. and the stirring was performed for 2 h before the completion of the reaction. The temperature was reduced to room temperature, and suction filtration was performed. The mother liquor was concentrated, and isolation was performed by column chromatography (200-300 mesh silica gel, heptane:EA=20:1) to obtain a product (420 mg, yield=42.0%) as a light yellow solid. $^1$H-NMR (400M, $CDCl_3$): δ ppm 9.98 (s, 1H), 8.05 (d, J=8.0 Hz, 1H), 7.70 (dd, $J_1$=8.0 Hz, $J_2$=1.6 Hz, 1H), 7.56-7.60 (m, 2H), 7.52-7.56 (m, 3H), 7.12-7.17 (m, 4H).

Under the protection of nitrogen, 9-A2 (400 mg, 1.19 mmol) was dissolved in anhydrous THF (8 mL), and then (trifluoromethyl)-trimethylsilane (254 mg, 1.79 mmol) was added dropwise. The temperature was reduced to 0° C., and TBAF (0.03 mL, 1 MinTHF) was added dropwise. The temperature was kept at 0° C. for 1.5 h until the completion of the reaction. 2 mL of 3N hydrochloric acid was added dropwise. The temperature was naturally increased to room temperature. Stirring was performed for 1 h. 5 mL of water was added. Extraction was performed with DCM (10 m×3) followed by washing with water (5 mL×3), drying, concentration and column separation (200-300 mesh silica gel, n-heptane:EA=10:1) to obtain the product 9-A3 (380 mg, yield=78.4%) as a light yellow solid. $^1$H-NMR (400M, $CDCl_3$): δ ppm 8.00 (d, J=8.4 Hz, 1H), 7.51-7.57 (m, 4H), 7.35 (d, J=8.4 Hz), 7.24 (s, 1H), 7.10-7.16 (m, 4H), 5.04-5.06 (m, 1H). LCMS: Calculated 407.0, found 430.0 ([M+Na]$^+$).

Under the protection of nitrogen, phosphorus oxychloride (285 mg, 1.866 mmol) was added dropwise to anhydrous DCM (10 mL). The temperature was reduced to −40° C. DCM solution (4 mL) of 9-A3 (380 mg, 0.933 mmol) was added dropwise, then triethylamine (236 mg, 2.333 mmol) was added dropwise, and the temperature was kept at a temperature between −40° C. and −35° C. for 2 h. As monitored by LC-LCMS, 9-A3 disappeared and was converted to an intermediate. 2-Bromoethylamine hydrobromide (1.53 g, 7.464 mmol) was added at −40° C., and then DCM solution (2 ml) of triethylamine (755 mg, 7.464 mmol) was added dropwise. The temperature was kept at −40° C. for 1 h, and the intermediate was completely converted. The temperature was naturally increased to 0° C., and saturated ammonium chloride aqueous solution (5 mL) was added dropwise. Extraction was performed with DCM (10 mL×3) followed by washing with pure water (3 mL×3), drying, concentration and column separation (200-300 mesh silica gel, n-heptane:EA=1:1) to obtain a product (m=350 mg, yield=53.7%) as an off-white solid. $^1$H-NMR (400M, $CDCl_3$): δ ppm 8.01 (d, J=8.4 Hz, 1H), 7.52-7.58 (m, 4H), 7.34 (d, J=8.4 Hz, 1H), 7.11-7.18 (m, 5H), 5.61-5.68 (m, 1H), 3.13-3.81 (m, 10H). LCMS Calculated: 699.0, found 700.0 ([M+H]$^+$).

Under the protection of nitrogen, 9-A4 (350 mg, 0.5 mmol) was dissolved in THF (10 mL), and then silver oxide (700 mg, 3.0 mmol) and DIPEA (390 mg, 3.0 mmol) were added. The temperature was increased to 65° C. and stirring was performed for 3 h. After the reaction was complete, the temperature was reduced to room temperature. Suction filtration through Celite® was performed. The solid was washed with DCM, the mother liquor was concentrated, and a pure product (m=31.4 mg, a white solid, yield=11.7%) was obtained by preparative chromatography. $^1$H-NMR (400M, $CD_3OD$): δ ppm 8.08 (d, J=8.4 Hz, 1H), 7.63-7.69 (m, 4H), 7.50 (d, J=8.4 Hz, 1H), 7.31 (s, 1H), 7.16-7.20 (m, 4H), 5.99-6.04 (m, 1H), 2.03-2.24 (m, 8H). LCMS: Calculated 537.0, found 538.0 ([M+H]$^+$).

Synthesis of Compound No. 11

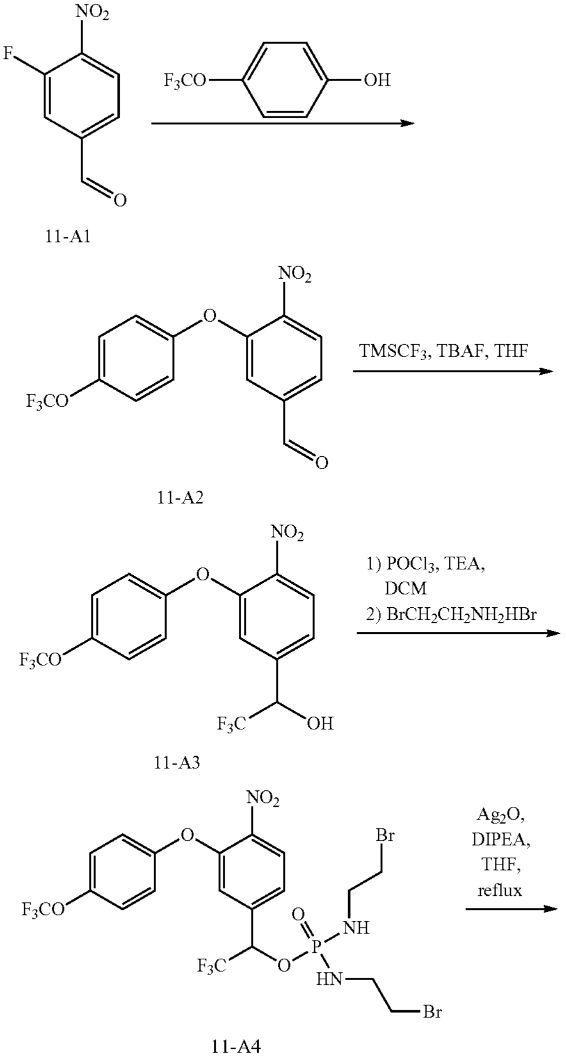

11-A1

11-A2

11-A3

11-A4

-continued

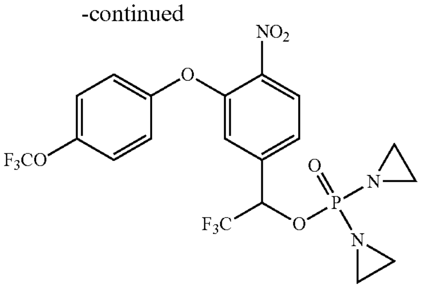

11

Under the protection of nitrogen, 11-A1 (500 mg, 2.97 mmol) and p-trifluoromethoxyphenol (684 mg, 3.84 mmol, commercially available pharmaceuticals) were dissolved in acetonitrile (10 mL). Potassium carbonate (820 mg, 5.94 mmol, commercially available) was added. The temperature was increased to 85° C. and the stirring was performed for 2 h before the completion of the reaction. The temperature was reduced to room temperature, and suction filtration was performed. The mother liquor was concentrated, and isolation was performed by column chromatography (200-300 mesh silica gel, n-heptane:EA=30:1) to obtain the product 11-A2 (totaling 520 mg, a light yellow solid, yield=53.5%). $^1$H-NMR (400M, $CDCl_3$): δ ppm 9.99 (s, 1H), 8.06 (d, J=8.4 Hz, 1H), 7.73 (dd, $J_1$=8.4 Hz, $J_2$=1.6 Hz, 1H), 7.50 (d, $J_2$=1.2 Hz, 1H), 7.29 (d, J=8.4 Hz, 1H), 7.10-7.14 (m, 2H).

Under the protection of nitrogen, 11-A2 (500 mg, 1.528 mmol) was dissolved in anhydrous THF (8 mL), and then (trifluoromethyl)-trimethylsilane (370 mg, 2.598 mmol) was added dropwise. The temperature was reduced to 0° C., and TBAF (0.03 mL, 1 MinTHF) was added dropwise. The temperature was kept at 0° C. for 1.5 until the completion of the reaction. 2 mL of 3N hydrochloric acid was added dropwise. The temperature was naturally increased to room temperature. Stirring was performed for 1 h. 5 mL of water was added. Extraction was performed with DCM (10 ml×3) followed by washing with water (5 mL×3), drying, concentration and column separation (200-300 mesh silica gel, n-heptane:EA=20:1 to 10:1) to obtain a product (400 mg, yield=65.9%) as a yellow oil. $^1$H-NMR (400M, $CDCl_3$): δ ppm 8.00 (d, J=8.4 Hz, 1H), 7.38 (d, J=8.4 Hz, 1H), 7.25 (d, J=8.8 Hz, 2H), 7.21 (s, 1H), 7.06 (d, J=8.8 Hz, 2H), 5.04-5.09 (m, 1H), 3.05 (brs, 1H)

Under the protection of nitrogen, phosphorus oxychloride (310 mg, 2.014 mmol) was added dropwise to anhydrous DCM (10 mL). The temperature was reduced to −40° C. DCM solution (4 mL) of 11-A3 (400 mg, 1.007 mmol) was added dropwise, then triethylamine (255 mg, 2.518 mmol) was added dropwise, and the temperature was kept at a temperature ranging from −40° C. to −35° C. for 2 h. As monitored by LC-LCMS, 11-A3 disappeared and was converted to an intermediate. 2-Bromoethylamine hydrobromide (1.65 g, 8.056 mmol) was added at −40° C., and then DCM solution (2 ml) of triethylamine (815 mg, 8.056 mmol) was added dropwise. The temperature was kept at −40° C. for 1 h, and the intermediate was completely converted. The temperature was naturally increased to 0° C., and saturated ammonium chloride aqueous solution (5 mL) was added dropwise. Extraction was performed with DCM (10 mL×3) followed by washing with pure water (3 mL×3), drying, concentration and column separation (200-300 mesh silica gel, n-heptane:EA=1:1-100% EA) to obtain the product 11-A4 (m=160 mg, yield=23.1%) as a yellow oily liquid. $^1$H-NMR (400M, $CDCl_3$): δ ppm 8.02 (d, J=8.4 Hz, 1H), 7.38 (d, J=8.4 Hz, 1H), 7.27 (d, J=8.8 Hz, 2H), 7.14 (s, 1H), 7.08 (d, J=8.8 Hz, 2H), 5.63-5.68 (m, 1H), 3.46-3.49 (m, 2H), 3.34-3.42 (m, 2H), 3.26-3.32 (m, 2H), 3.02-3.25 (m, 4H). LCMS: Calculated LCMS: 688.9, found 689.8 ([M+H]$^+$).

Under the protection of nitrogen, 11-A4 (160 mg, 0.230 mmol) was dissolved in THF (10 mL), and then silver oxide (323 mg, 1.393 mmol) and DIPEA (180 mg, 1.393 mmol) were added. The temperature was increased to 65° C. and stirring was performed for 3 h. After the reaction was complete, the temperature was reduced to room temperature. Suction filtration through Celite® was performed. The solid was washed with DCM, the mother liquor was concentrated, and pure Compound No. 11 (m=26.3 mg, yield=21.7%) was obtained as a yellow wax. $^1$H-NMR (400M, $CDCl_3$): δ ppm 8.01 (d, J=8.4 Hz 1H), 7.39 (d, J=8.4 Hz, 1H), 7.26 (d, J=8.8 Hz, 2H), 7.18 (s, 1H), 7.05-7.08 (m, 2H), 5.60-5.74 (m, 1H), 2.00-2.26 (m, 8H). LCMS: Calculated 527.1, found 528.0 ([M+H]$^+$).

Synthesis of Compound No. 12

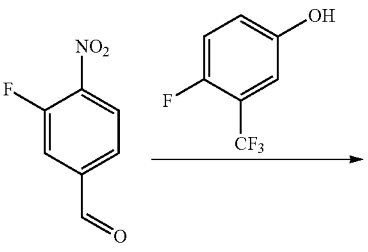

12-A1

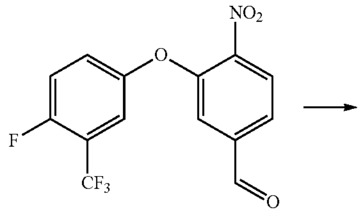

12-A2

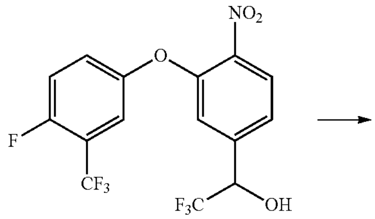

12-A3

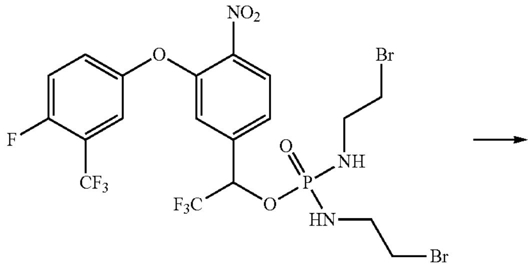

12-A4

-continued

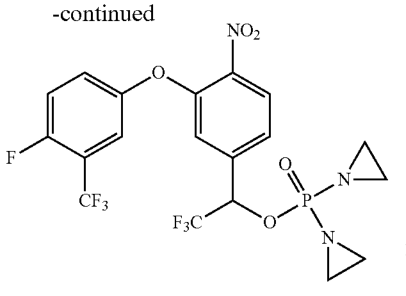

12

12-A1 (1.0 g, 5.9 mmol) and 4-fluoro-3 (trifluoromethyl) phenol (2.1 g, 11.8 mmol, 2 eq., commercially available) were dissolved in acetonitrile (20 mL) Under nitrogen, $K_2CO_3$ (1.6 g, 11.8 mmol, 2 eq.) was added to the system. The temperature was increased to 80° C. After monitored for 1 h, the raw materials disappeared and the reaction was complete. Post-treatment was performed as follows. After cooled to room temperature, the system was subjected to suction filtration through Celite®, and washed with DCM. After the mother liquor was spin-dried, the sample was mixed with 300-400 silica gel (10 times) and passed through a flash column (n-heptane:EA=94%:6%) to obtain 12-A2 (1.15 g, 59.2%) as a light yellow oily liquid. $^1$H-NMR (400M, $CDCl_3$): δ ppm 10.00 (s, 1H), 8.08 (d, J=8.0 Hz, 1H), 7.76 (dd, $J_1$=8.4 Hz, $J_2$=1.6 Hz, 1H), 7.46 (d, J=1.6 Hz, 1H), 7.33-7.34 (m, 1H), 7.27-7.28 (m, 1H), 7.26-7.53 (m, 1H).

Under the protection of nitrogen, 12-A2 (620 mg, 1.9 mmol) and $TMSCF_3$ (539 mg, 3.8 mmol, 2 eq.) were dissolved in THF (6 mL). The temperature was reduced to 0° C. TBAF (0.04 ml, 0.04 mmol, 1 MinTHF, commercially available) was added dropwise to the system. After the temperature was kept at 0° C. for 30 min, 12-A2 disappeared completely. 3N HCl (3 ml) was added dropwise to the system, and the system became clear. After stirring at 0° C. for 1 h, all the raw materials were converted to products. Post-treatment was performed as follows. Extraction was performed with DCM (5 mL×3). The organic phase was washed with water (5 ml×3), dried and spin-dried. The sample was mixed with 300-400 silica gel (7 times) (n-heptane:EA=95:5) to obtain 12-A3 (600 mg, 79.1%) as a light yellow oil. $^1$H-NMR (400M, $CDCl_3$): δ ppm 8.02 (d, J=8.4 Hz, 1H), 7.41 (d, J=8.4 Hz, 1H), 7.29 (dd, $J_1$=6.4 Hz, $J_2$=2.8 Hz, 1H), 7.24-7.18 (m, 3H), 5.08 (dd, $J_1$=12.4 Hz, $J_2$=6.0 Hz, 1H).

Under the protection of nitrogen, $POCl_3$ (384 mg, 2.5 mmol, 2 eq.) was dissolved in DCM (5 ml). After that, the temperature was reduced to −40° C. Then, 12-A3 (500 mg, 1.3 mmol) was dissolved in DCM (2 ml) before being added dropwise to the system with TEA (317 mg, 3.1 mmol, 2.5 eq.). After the temperature was kept at −40° C. for 2 h, 12-A3 was completely converted to an intermediate. Then, 2-bromoethylamine hydrobromide (2.1 g, 10.0 mmol, 8 eq.) and TEA (1.0 g, 10.0 mmol) were added to the system. Monitoring was performed. The reaction was complete in 30 min. Post-treatment was performed as follows. At 0° C., saturated ammonium chloride aqueous solution (10 mL) was added. Extraction was performed with DCM (20 ml×3). The organic phase was washed with water and with brine and was spin-dried. After that, the sample was mixed with 200-300 silica gel (8 times) (n-heptane:EA=1:1) to obtain 12-A4 (350 mg, 39.0%) as a light yellow oil. $^1$H-NMR (400M, $CDCl_3$): δ ppm 8.06 (d, J=8.4 Hz, 1H), 7.44 (d, J=8.4 Hz, 1H), 7.33-7.35 (m, 1H), 7.24-7.29 (m, 2), 7.17 (s, 1H), 5.70 (dd, J=11.5, 6.0 Hz, 1H), 3.86-2.96 (m, 10H). LCMS: Calculated 690.9, found 691.8 ([M+1]$^+$).

Under the protection of nitrogen, 12-A4 (350 mg, 0.5 mmol) was dissolved in THF (10 ml). Then, $Ag_2O$ (587 mg, 2.5 mmol) and DIEA (327 mg, 2.5 mmol, 5 eq.) were added to the system. The temperature was increased to reflux temperature, the reaction was monitored, and the reaction was complete in 2 h. The temperature was reduced to room temperature. Suction filtration through Celite® was performed. Washing was performed with DCM. The mother liquor was spin-dried. Compound No. 12 (74 mg, 26.4%) was obtained as a light yellow solid by neutral preparative chromatography. $^1$H-NMR (400M, $CDCl_3$): δ ppm 8.04 (d, J=8.4 Hz, 1H), 7.43 (dd, J=8.4 Hz, 1H), 7.28-7.26 (m, 1H), 7.23-7.22 (m, 2H), 7.18 (s, 1H), 5.76-5.71 (m, 1H), 2.27-2.02 (m, 8H).

LCMS: Calculated 529.1, found 530.0 ([M+1]$^+$)

Synthesis of Compound No. 13

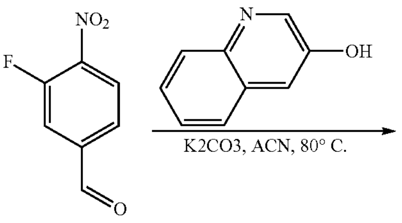

13-A1

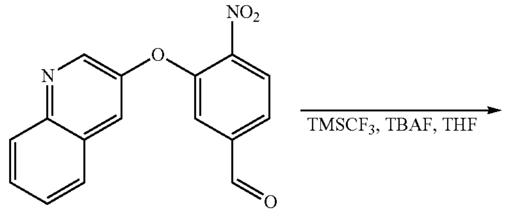

13-A2

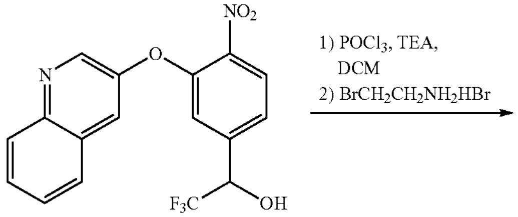

13-A3

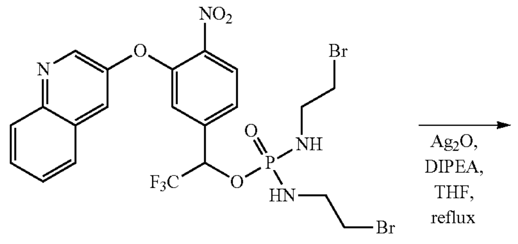

13-A4

-continued

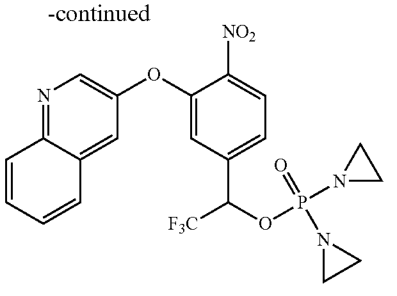

13

Under the protection of nitrogen, 13-A1 (500 mg, 2.95 mmol) and 3-hydroxyquinoline (470 mg, 3.24 mmol, commercially available) were dissolved in acetonitrile ACN (5 ml). Potassium carbonate (830 mg, 6 mmol) was added. The temperature was increased to 80° C. and stirring was performed for 4 h. After the completion of the reaction, suction filtration through Celite® was performed followed by concentration. The sample was mixed and was subjected to column chromatography separation (100-200 mesh silica gel, n-heptane:EA=10:1) to obtain a product (560 mg, 64.5%) as a white solid, which was directedly used in the next step. $^1$H-NMR (300 MHz, DMSO): δ ppm 10.02 (s, 1H), 8.92 (d, J=2.6 Hz, 1H), 8.34 (d, J=8.2 Hz, 1H), 8.09 (d, J=8.6 Hz, 2H), 7.94 (t, J=8.2 Hz, 2H), 7.82 (s, 1H), 7.76 (t, J=7.1 Hz, 1H), 7.65 (t, J=7.2 Hz, 1H). LCMS: Calculated 294.0, found 295.0 ([M+H]$^+$).

Under the protection of nitrogen, 13-A2 (460 mg, 1.56 mmol), and trifluoromethyltrimethylsilane (430 mg, 3 mmol) were dissolved in THF (5 mL). At 0° C., THF solution (0.1 mL, 0.1 mmol, 1 M) of tetrabutylammonium fluoride was added dropwise. The temperature was maintained for 6 h. 1N hydrochloric acid (2 mL) was added and stirred for 10 min. THF was removed by concentration. Water (10 ml) was added to the crude product and extraction was performed with DCM (20 ml). The organic phase was separated and concentrated, and the sample was mixed. The crude product was subjected to column chromatography separation (100-200 mesh silica gel, n-heptane:EA=10:1) to obtain a product (400 mg) as a light yellow solid. $^1$H-NMR (400 MHz, DMSO): δ ppm 8.87 (d, J=2.8 Hz, 1H), 8.23 (d, J=8.5 Hz, 1H), 8.08 (d, J=8.4 Hz, 1H), 8.00 (d, J=2.7 Hz, 1H), 7.96 (d, J=7.4 Hz, 1H), 7.76 (ddd, J=8.4, 6.9, 1.4 Hz, 1H), 7.69-7.62 (m, 1H), 7.58 (d, J=8.5 Hz, 1H), 7.43 (s, 1H), 7.19 (d, J=5.9 Hz, 1H), 5.43-5.31 (m, 1H). LCMS: Calculated 364.0, found 365.0 ([M+H]$^+$).

Under the protection of nitrogen, $POCl_3$ (168 mg, 1.1 mmol) was added dropwise to ultra-dry DCM (5 ml). The temperature was reduced to −30° C. DCM (5 ml) solution of 13-A3 (200 mg, 0.55 mmol) was added dropwise, then TEA (170 mg, 1.65 mmol) was added dropwise, and the temperature was kept at −30° C. for 6 h until the raw materials disappeared completely. 2-Bromoethylamine hydrobromide (897 mg, 4.4 mmol) was added at −30° C., and then TEA (440 mg, 4.4 mmol) was added dropwise. After the completion of the reaction, the temperature was reduced to 0° C. $NH_4Cl$ saturated solution (10 ml) was added. Extraction was performed with DCM (15 ml×2) followed by washing with water (5 mL×4), drying and concentration to obtain 150 mg of the crude product as a yellow solid, which was directedly used in the reaction in the next step.

Under the protection of nitrogen, 13-A4 (150 mg, 0.23 mmol) was dissolved in THF (10 ml), and $Ag_2O$ (170 mg, 1.38 mmol) and N,N-diisopropylethylamine (163 mg, 1.38 mmol) were added. The temperature was increased to 65° C. After the reaction was complete in 2 h, suction filtration through Celite® was performed. The solid was washed with DCM (20 ml), the mother liquor was concentrated, and pure Compound No. 13 (41 mg, 36%) was obtained as a white solid by high-performance liquid preparative chromatography. $^1$H-NMR (400 MHz, MeOD): δ ppm 8.82 (d, J=2.8 Hz, 1H), 8.22 (d, J=8.5 Hz, 1H), 8.10 (d, J=8.6 Hz, 1H), 7.94-7.87 (m, 2H), 7.77 (ddd, J=8.4, 6.9, 1.4 Hz, 1H), 7.69-7.62 (m, 2H), 7.52 (s, 1H), 6.13-6.02 (m, 1H), 2.29-1.98 (m, 8H).

LCMS: Calculated 494.1, found 495.0 ([M+H]$^+$).

Synthesis of Compound No. 14

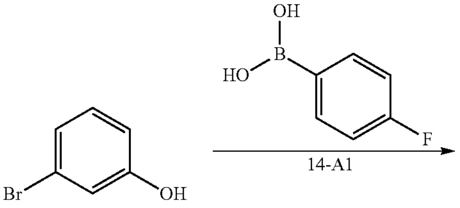

14-A0

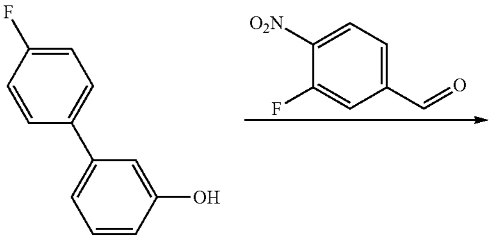

14-A2

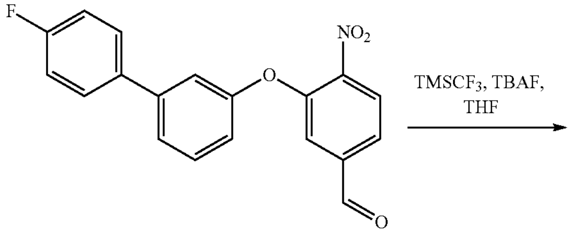

14-A3

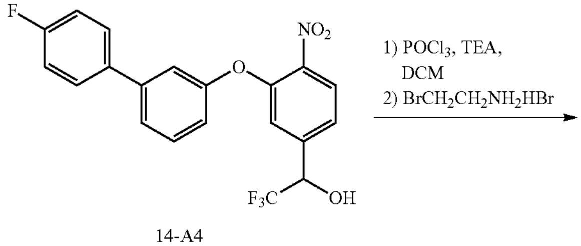

14-A4

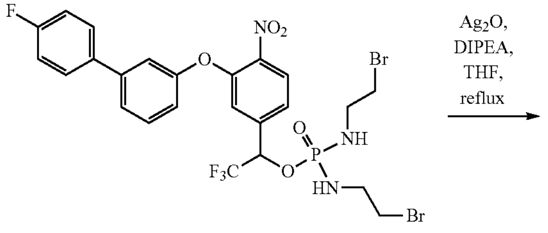

14-A5

-continued

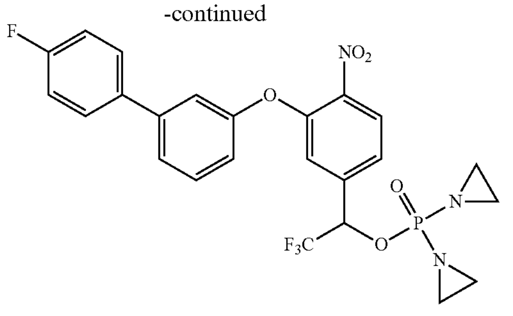

14

Under the protection of nitrogen, m-bromophenol (14-A0, 1.5 g, 8.57 mmol) and p-fluorophenylboronic acid (14-A1, 1.0 g, 7.15 mmol, commercially available) were added to a mixed liquid of dioxane (30 ml) and $H_2O$ (5 ml). Evacuation and filling with nitrogen were performed 3 times. After $Pd(AcO)_2$ (80 mg, 0.36 mmol), $PPh_3$ (94 mg, 0.36 mmol) and $K_2CO_3$ (3.0 g, 21.44 mmol) were added, evacuation and filling with nitrogen were performed 3 times again, and the temperature was increased to 100° C. The reaction was monitored for 1 h before it was complete. Post-treatment was performed as follows. The temperature was reduced to room temperature. After suction filtration, extraction was performed with EtOAc (50 ml×3). The organic phase was washed with water and washed with brine and was subjected to column separation (200-300 mesh silica gel, n-heptane: EA=12:1 to 9:1) to obtain the product 14-A2 (1.1 g, yield=62.7%) as a white solid. $^1$H-NMR (300 MHz, MeOD): δ ppm 7.59-7.54 (m, 2H), 7.23-7.10 (m, 3H), 7.04-6.99 (m, 2H), 6.76 (dd, J=8.1, 1.5 Hz, 1H). LCMS: Calculated 188.1, found 189.1 ([M+H]$^+$).

14-A2 (580 mg, 3.08 mmol) and 3-fluoro-4-nitrobenzaldehyde (434 mg, 2.57 mmol, commercially available) were dissolved in acetonitrile (10 mL). Under nitrogen, $K_2CO_3$ (887 mg, 6.42 mmol) was added to the system. The temperature was increased to 80° C. After monitored for 2 h, the reaction was complete. After the temperature was reduced to room temperature, suction filtration through Celite® was performed, followed by washing with DCM. The mother liquor was concentrated, and subjected to column separation (flash reversed-phase column, acetonitrile: $H_2O$=50%:50%) to obtain the product 14-A3 (320 mg, 33.7%) as a yellow oil. $^1$H-NMR (400 MHz, $CDCl_3$): δ ppm 9.98 (s, 1H), 8.05 (d, J=8.4 Hz, 1H), 7.71 (d, J=1.6 Hz, 1H), 7.69-7.43 (m, 5H), 7.28-7.27 (m, 1H), 7.15-7.11 (m, 2H), 7.08-7.05 (m, 1H).

Under the protection of nitrogen, 14-A3 (350 mg, 1.04 mmol) and $TMSCF_3$ (296 mg, 2.08 mmol) were dissolved in THF (4 mL). The temperature was reduced to 0° C. TBAF (0.01 mL, 0.01 mmol, 1 M in THF) was added dropwise to the system. After the temperature was kept at 0° C. for 30 min, the reactant 14-A3 disappeared completely. 3N HCl (2 ml) was added dropwise to the system, and the system became clear. After stirring at 0° C. for 1 h, all the raw materials were converted to products. Extraction was performed with DCM (5 mL×3). The organic phase was washed with water (5 ml×3), dried, concentrated, and subjected to column separation (200-300 mesh silica gel, n-heptane: EA=12:1 to 10:1) to obtain the product (350 mg, yield=82.8%) as a yellow solid. $^1$H-NMR (400 MHz, $CDCl_3$): δ ppm 8.00 (d, J=8.4 Hz, 1H), 7.53-7.34 (m, 5H), 7.24-7.23 (m, 2H), 7.15-7.11 (m, 2H), 7.03-7.00 (m, 1H), 5.03-5.02 (m, 1H). LCMS: Calculated 407.1, found 408.0 ([M+H]$^+$).

Under the protection of nitrogen, $POCl_3$ (188 mg, 1.23 mmol) was dissolved in DCM (5 ml). After that, the temperature was reduced to −40° C. Then, 14-A4 (250 mg, 0.61 mmol) was dissolved in DCM (2 ml) before being added dropwise to the system with TEA (155 mg, 1.53 mmol). After the temperature was kept at −40° C. for 3 h, 15-A3 was completely converted to an intermediate. Then, bromoethylamine hydrobromide (1.0 g, 4.91 mmol) and TEA (497 mg, 4.91 mmol) were added to the system. Monitoring was performed. The reaction was complete in 30 min. At 0° C., saturated $NH_4Cl$ (5 ml) was added. Extraction was performed with DCM (20 ml×3). The organic phase was washed with water and washed with brine, dried, concentrated, and subjected to column separation (200-300 mesh silica gel, n-heptane:EA=2:1 to 1:1) to obtain a product (200 mg, 46.6%) as a yellow solid. $^1$H-NMR (400 MHz, $CDCl_3$): δ ppm 8.01 (d, J=8.4 Hz, 1H), 7.54-7.33 (m, 5H), 7.25 (d, J=2.0 Hz, 1H), 7.18 (s, 1H), 7.15-7.10 (m, 2H), 7.03 (d, J=1.2 Hz, 1H), 5.70-5.60 (m, 1H), 3.38-3.08 (m, 8H). LCMS: Calculated 699.0, found 699.9 ([M+H]$^+$).

Under the protection of nitrogen, 15-A5 (150 mg, 0.22 mmol) was dissolved in THF (15 ml), and then silver oxide (497 mg, 2.1 mmol) and DIPEA (277 mg, 2.1 mmol) were added. The temperature was increased to 65° C. and stirring was performed for 1.5 h. After the reaction was complete, the temperature was reduced to room temperature. Suction filtration through Celite® was performed. The solid was washed with DCM, the mother liquor was concentrated, and a pure product (56 mg, 48.6%) was obtained as a white solid by high-performance liquid preparative chromatography. $^1$H-NMR (400 MHz, MeOD) δ8.08 (d, J=8.4 Hz, 1H), 7.67-7.59 (m, 2H), 7.56-7.46 (m, 3H), 7.31 (d, J=2.2 Hz, 2H), 7.22-7.13 (m, 2H), 7.10-7.05 (m, 1H), 6.05-5.95 (m, 1H), 2.29-1.89 (m, 8H). LCMS: Calculated 537.1, found 538.1 ([M+H]$^+$).

Synthesis of Compound No. 15

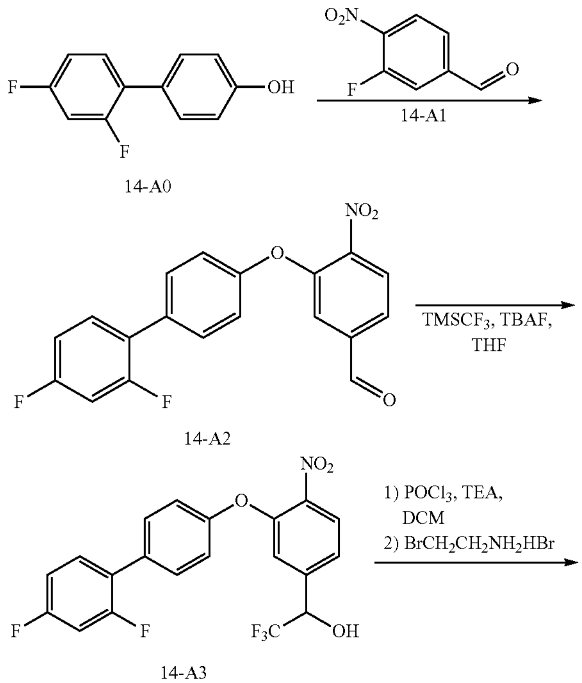

14-A0

14-A2

14-A3

-continued

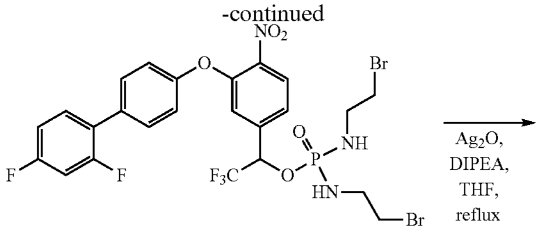

14-A5

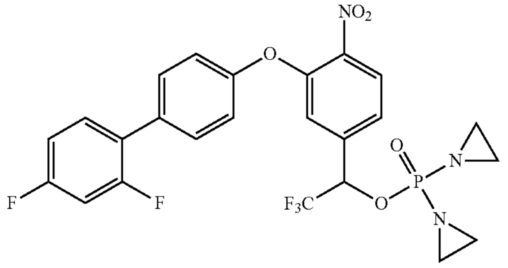

14

15-A1 (500 mg, 2.96 mmol, commercially available) and 15-A0 (554 mg, 2.69 mmol) were dissolved in acetonitrile (10 mL). Under nitrogen, $K_2CO_3$ (743 mg. 5.38 mmol) was added to the system. The temperature was increased to 80° C. After monitored for 1.5 h, the reaction was complete. After the temperature was reduced to room temperature, suction filtration through Celite® was performed, and washing was performed with DCM. The mother liquor was concentrated, and subjected to column separation (200-300 mesh silica gel, n-heptane:EA=15:1 to 10:1) to obtain a product (535 mg, yield=56.0%) as a brown oil. $^1$H-NMR (400 MHz, $CDCl_3$): δ ppm 9.99 (s, 1H), 8.05 (d, J=8.4 Hz, 1H), 7.71 (d, J=8.4 Hz, 1H), 7.56-7.55 (m, 3H), 7.41 (dd, $J_1$=8.44.8 Hz, 1H), 7.16 (d, J=8.4 Hz, 2H), 7.00-6.91 (m, 2H).

Under the protection of nitrogen, 15-A2 (400 mg, 1.13 mmol) and TMSCF3 (320 mg, 2.25 mmol) were dissolved in the THF (4 mL). The temperature was reduced to 0° C. TBAF (0.02 ml, 0.02 mmol, 1 MinTHF) was added dropwise to the system. After the temperature was kept at 0° C. for 30 min 15-A2 disappeared completely. 3N HCl (2 ml) was added dropwise to the system, and the system became clear. After stirring at 0° C. for 1 h, extraction was performed with DCM (5 mL×3). The organic phase was washed with water (5 ml×3), dried, and concentrated to obtain the crude product (405 mg, yield=56.4%) as a yellow solid, which was directly used in the next step. LCMS: Calculated 425.3, found 426.0 ([M+1]$^+$).

Under the protection of nitrogen, $POCl_3$ (209 mg, 1.36 mmol, commercially available) was dissolved in DCM (5 ml). After that, the temperature was reduced to −40° C. Ten, 15-A3 (290 mg, 0.68 mmol) was dissolved in DCM (2 ml) before being added dropwise to the system with TEA (173 mg, 1.70 mmol). After the temperature was kept at −40° C. for 2 h, 15-A3 was completely converted to an intermediate. Then, bromoethylamine hydrobromide (1.1 g, 5.46 mmol) and TEA (552 mg, 5.46 mmol) were added to the system. Monitoring was performed. The reaction was complete in 30 min. At 0° C., saturated $NH_4Cl$ (5 ml) was added. Extraction was performed with DCM (20 ml×3). The organic phase was washed with water and washed with brine. The organic phase was dried, concentrated and subjected to column separation (200-300 mesh silica gel, n-heptane:EA=5:1 to 3:1) to obtain a product (250 mg, yield=51.1%) as a yellow solid. $^1$H-NMR (400 MHz, $CDCl_3$): δ ppm 8.00 (d, J=8.4 Hz, 1H), 7.54 (d, J=7.6 Hz, 2H), 7.44-7.38 (m, 1H), 7.35 (d, J=8.4 Hz, 1H), 7.21 (s, 1H), 7.13 (d, J=8.8 Hz, 1H), 7.00-6.95 (m, 2H), 5.68-5.62 (m, 1H), 3.42-3.11 (m, 8H). LCMS: Calculated 717.2, found 717.9 ([M+H]$^+$).

Under the protection of nitrogen, 15-A4 (230 mg, 0.32 mmol) was dissolved in THF (15 ml), and then silver oxide (372 mg, 1.60 mmol) and DIPEA (207 mg, 1.60 mmol) were added. The temperature was increased to 65° C. and stirring was performed for 1.5 h. After the reaction was complete, the temperature was reduced to room temperature. Suction filtration through Celite® was performed. The solid was washed with DCM, the mother liquor was concentrated, and a pure product (102 mg, 57.5%) was obtained as a white solid by high-performance liquid preparative chromatography. $^1$H-NMR (400 MHz, $CDCl_3$): δ ppm 8.01 (d, J=8.4 Hz, 1H), 7.54 (d, J=1.6 Hz, 2H), 7.51-7.36 (m, 2H), 7.24 (s, 1H), 7.12-7.11 (m, 2H), 6.97-6.93 (m, 2H), 5.72-5.69 (m, 1H), 2.26-2.01 (m, 8H). LCMS: Calculated 555.1, found 556.1 ([M+H]$^+$).

Synthesis of Compound No. 16

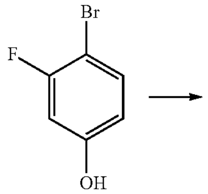

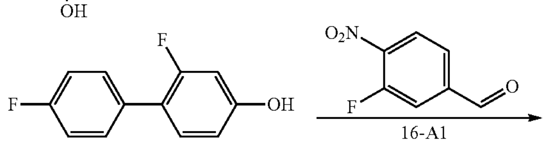

16-A0

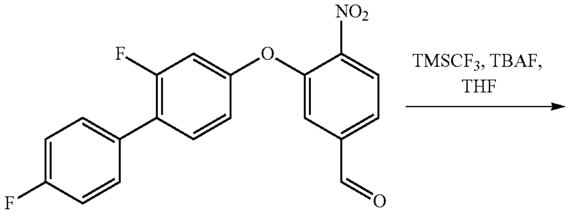

16-A2

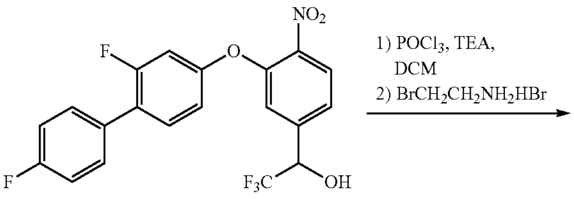

16-A3

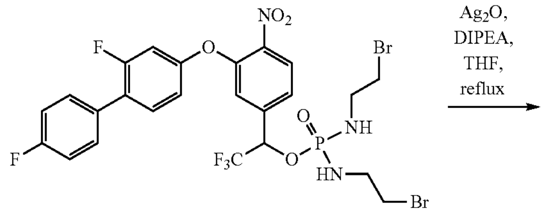

16-A4

-continued

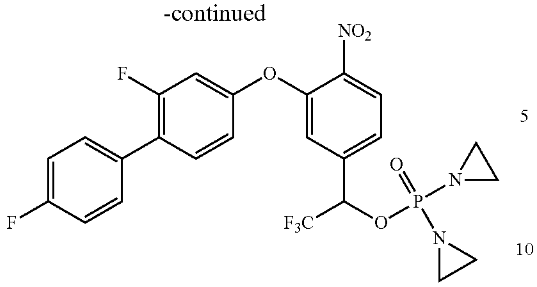

16

Under the protection of nitrogen, 3-fluoro-4-bromophenol (5.0 g, 26.2 mmol, commercially available, 97%) and p-fluorophenylboronic acid (4.0 g, 28.8 mmol, commercially available, 97%) were dissolved in a mixed solvent (100 ml, dioxane:water=9:1) of dioxane and water. After that, potassium carbonate was added (10.8 g, 78.6 mmol). Evacuation and filling with gas were performed three times. After palladium acetate (295 mg, 1.31 mmol, commercially available, 95%), and triphenylphosphine (345 mg, 1.31 mmol, commercially available, 97%) were added, evacuation and filling with gas were again performed three times. The temperature was increased to 100° C. and stirring was performed overnight. After the completion of the reaction, the temperature was reduced to room temperature. Suction filtration through Celite® was performed, and washing was performed with EA The mother liquor was concentrated, and adjusted to pH=3 with 1N hydrochloric acid. Extraction was performed with EA (50 ml×3) followed by washing with water (10 ml×3) and washing with brine, drying, concentration and column separation (100-200 mesh silica gel, n-heptane:EA=20:1) to obtain the product 16-A0 (3.5 g, 64.8%) as a white solid. $^1$H-NMR (300M, DMSO-$d_6$): δ ppm 10.02 (s, 1H), 7.52-7.47 (m, 2H), 7.34-7.23 (m, 3H), 6.71-6.64 (m, 2H). LCMS: Calculated 206.1, found 204.8 ([M−H]$^-$).

Under the protection of nitrogen, 16-A1 (930 mg, 5.50 mmol, commercially available, 97%) and 16-A0 (1.36 g, 6.60 mmol) were dissolved in acetonitrile (20 ml). Potassium carbonate (1.52 g, 11.0 mmol, commercially available, 99%) was added. The temperature was increased to 85° C. and stirring was performed for 2 h before the completion of the reaction. After the temperature was reduced to room temperature, suction filtration was performed. The mother liquor was concentrated, and subjected to column separation (200-300 mesh silica gel, n-heptane:EA=15:1) to obtain 16-A2 (1.10 g, 56.4%) as a light yellow solid. $^1$H-NMR (400 MHz, DMSO-$d_6$): δ ppm 10.05 (s, 1H), 8.30 (d, J=8.3 Hz, 1H), 7.92 (dd, J=8.3, 1.5 Hz, 1H), 7.78 (d, J=1.5 Hz, 1H), 7.69-7.55 (m, 3H), 7.36-7.28 (m, 2H), 7.27-7.21 (m, 1H), 7.09 (dd, J=8.5, 2.3 Hz, 1H).

Under the protection of nitrogen, 16-A2 (700 mg, 1.970 mmol) was dissolved in anhydrous THF (10 mL), and then (trifluoromethyl)-trimethylsilane (476 mg, 3.35 mmol, commercially available, 98%) was added dropwise. The temperature was reduced to 0° C., and TBAF (0.04 mL, 1 MinTHF) was added dropwise. The temperature was kept at 0° C. for 1.5 h until the completion of the reaction. 2 mL of 3N hydrochloric acid was added dropwise. The temperature was naturally increased to room temperature. Stirring was performed for 1 h. 5 mL of water was added. Extraction was performed with DCM (10 ml×3) followed by washing with water (5 mL×3), drying, concentration and column separation (200-300 mesh silica gel, n-heptane:EA=15:1 to 10:1) to obtain the product 16-A3 (810 mg, 96.7%) as a yellow oil. $^1$H-NMR (400 MHz, DMSO-$d_6$): δ ppm 8.19 (d, J=8.5 Hz, 1H), 7.63-7.52 (m, 4H), 7.44 (s, 1H), 7.32 (t, J=8.9 Hz, 2H), 7.21 (d, J=5.8 Hz, 1H), 7.14 (dd, J=11.7, 2.4 Hz, 1H), 6.97 (dd, J=8.5, 2.1 Hz, 1H), 5.44-5.37 (m, 1H).

Under the protection of nitrogen, phosphorus oxychloride (580 mg, 3.76 mmol, commercially available, 97%) was added dropwise to anhydrous DCM (10 mL). The temperature was reduced to −40° C. DCM solution (4 mL) of 16-A3 (800 mg, 1.88 mmol) was added dropwise, then triethylamine (476 mg, 4.70 mmol) was added dropwise, and the temperature was kept at a temperature ranging from −40° C. to −35° C. for 2 h. As monitored by LC-LCMS, 16-A3 disappeared and was converted to an intermediate. 2-Bromoethylamine hydrobromide (3.08 g, 15.04 mmol) was added at −40° C., and then DCM solution (2 ml) of triethylamine (1.52 g, 15.04 mmol) was added dropwise. The temperature was kept at −40° C. for 1 h, and the intermediate was completely converted. The temperature was naturally increased to 0° C., and saturated ammonium chloride aqueous solution (5 mL) was added dropwise. Extraction was performed with DCM (10 mL×3) followed by washing with pure water (3 mL×3), drying, concentration and column separation (200-300 mesh silica gel, n-heptane:EA=1:1 to 100) to obtain the product 16-A4 (totaling 600 mg, yield=44.4%) as a white solid. $^1$H-NMR (400M, $CDCl_3$): δ ppm 8.04 (d, J=8.4 Hz, 1H), 7.55-7.47 (m, 2H), 7.46-7.38 (m, 2H), 7.27 (s, 1H), 7.19-7.10 (m, 2H), 6.95-6.83 (m, 2H), 5.69 (dd, J=11.4, 6.1 Hz, 1H), 3.50-3.18 (m, 8H). LCMS: Calculated 716.9, found 717.8 ([M+H]$^+$).

Under the protection of nitrogen, 16-A4 (600 mg, 0.837 mmol) was dissolved in THF (15 ml), and then silver oxide (1.16 mg, 5.02 mmol) and DIPEA (649 mg, 5.02 mmol) were added. The temperature was increased to 65° C. and stirring was performed for 3 h. After the reaction was complete, the temperature was reduced to room temperature. Suction filtration through Celite® was performed. The solid was washed with DCM, and the mother liquor was concentrated. Crystallization was performed by adding 1.5 ml of anhydrous ether, and suction filtration was performed to obtain pure Compound No. 16 (159 mg, yield=34.2%) as a white solid. $^1$H-NMR (400 MHz, MeOD) δ ppm 8.12 (t, J=8.1 Hz, 1H), 7.55 (m, 4H), 7.45 (s, 1H), 7.19 (t, J=8.8 Hz, 2H), 6.98 (dd, J=7.8, 5.3 Hz, 2H), 6.15-5.98 (m, 1H), 2.39-1.93 (m, 8H). LCMS: Calculated 555.1, found 556.1 ([M+H]$^+$).

Synthesis of Compound No. 17

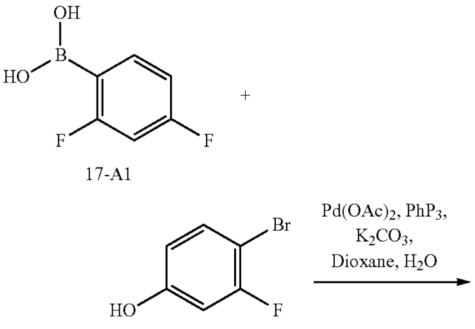

17-A1

17-A2

-continued

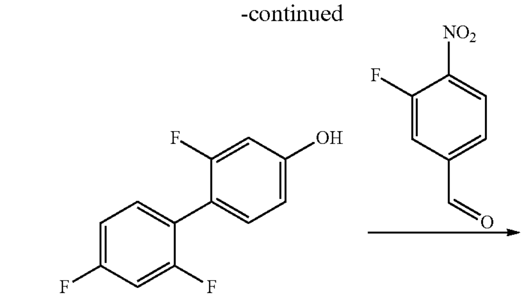

17-A3

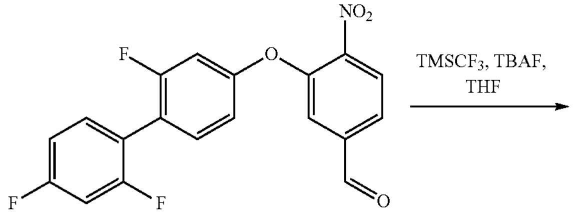

17-A4

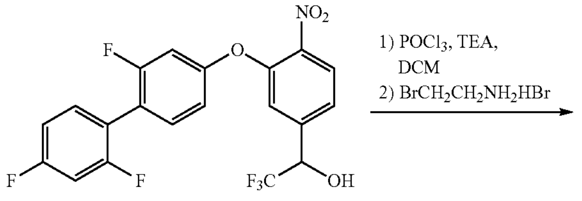

17-A5

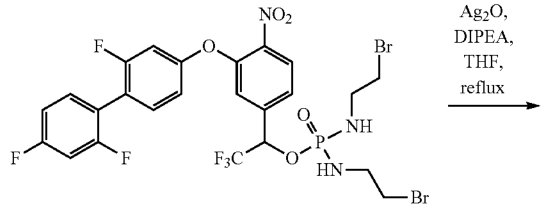

17-A6

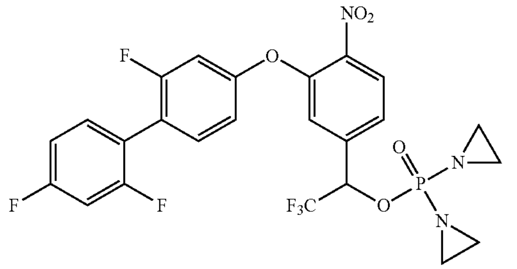

17

Under the protection of nitrogen, 17-A1 (1.7 g, 11 mmol, commercially available), 17-A2 (2 g, 10 mmol), palladium acetate (21.5 mg, 0.1 mmol), triphenylphosphine (39 mg, 0.15 mmol) and potassium carbonate (2.8, 20 mmol) were dissolved in dioxane (20 ml) and water (2 ml). The temperature was increased to 80° C. and stirring was performed overnight. After the completion of the reaction, suction filtration through Celite® was performed followed by concentration. The sample was mixed and subjected to column chromatography separation (100-200 mesh silica gel, n-heptane:EA=5:1) to obtain the product 17-A3 (900 mg, 40%) as a white solid. $^1$H-NMR (300 MHz, DMSO) δ 10.17 (s, 1H), 7.55-7.08 (m, 3H), 6.79-6.50 (m, 3H). LCMS: Calculated 224.0, found 222.6 [(M−H)$^-$].

Under the protection of nitrogen, 17-A3 (500 mg, 2.2 mmol), and 3-fluoro-4-nitrobenzaldehyde (370 mg, 2.2 mmol, commercially available) were dissolved in ACN (5 ml). Potassium carbonate (830 mg, 6 mmol) was added. The temperature was increased to 80° C. and stirring was performed for 4 h. After the completion of the reaction, suction filtration through Celite® was performed followed by concentration. The sample was mixed and subjected to column chromatography separation (100-200 mesh silica gel, n-heptane:EA=10:1) to obtain 700 mg of the crude product 17-A4 (a white solid, with a purity of 80%), which was directedly used in the next step. $^1$H-NMR (300 MHz, DMSO) δ 10.03 (s, 1H), 8.31 (d, J=8.2 Hz, 1H), 7.94 (d, J=8.4 Hz, 1H), 7.83 (s, 1H), 7.59-7.50 (m, 2H), 7.40 (t, J=8.8 Hz, 1H), 7.32-7.16 (m, 2H), 7.10 (d, J=8.6 Hz, 1H).

Under the protection of nitrogen, 17-A4 (680 mg, 1.82 mmol) and trifluoromethyltrimethylsilane (510 mg, 3.6 mmol, commercially available) were dissolved in THF (8 mL). At 0° C., THF solution (0.1 mL, 0.1 mmol, 1 M, commercially available) of tetrabutylammonium fluoride was added dropwise. The temperature was maintained for 6 h. 1N hydrochloric acid (2 mL) was added and stirred for 10 min. THF was removed by concentration. Water (10 ml) was added to the crude product and extraction was performed with DCM (20 ml). The organic phase was separated and concentrated, and the sample was mixed. The crude product was subjected to separation by column chromatography (100-200 mesh silica gel, n-heptane:EA=10:1) to obtain the product 17-A5 (400 mg, yield=49.6%, purity=90%) as a light yellow solid. $^1$H-NMR (300 MHz, DMSO) δ 8.19 (d, J=7.8 Hz, 1H), 7.76 (t, J=8.5 Hz, 1H), 7.57-7.51 (m, 2H), 7.38 (s, 1H), 7.28-7.19 (m, 3H), 6.89 (dd, J=8.8, 1.7 Hz, 1H), 5.40-5.36 (m, 1H).

Under the protection of nitrogen, $POCl_3$ (168 mg, 1.1 mmol, commercially available) was added dropwise to ultra-dry DCM (5 ml). The temperature was reduced to −30° C. DCM (5 ml) solution of 17-A5 (220 mg, 0.5 mmol) was added dropwise, then TEA (170 mg, 1.65 mmol) was added dropwise, and the temperature was kept at −30° C. for 6 h until the raw materials disappeared completely. 2-Bromoethylamine hydrobromide (897 mg, 4.4 mmol) was added at −30° C., and then TEA (440 mg, 4.4 mmol) was added dropwise. After the completion of the reaction, the temperature was reduced to 0° C. $NH_4Cl$ saturated solution (10 ml) was added. Extraction was performed with DCM (15 ml×2) followed by washing with water (5 mL×4), drying and concentration to obtain 250 mg of the crude product 17-A6 as a yellow solid, which was directedly used in the reaction in the next step. LCMS: Calculated 732.9, found 733.9 ([M+H]$^+$).

Under the protection of nitrogen, 17-A6 (250 mg, 0.34 mmol) was dissolved in THF (10 ml), and $Ag_2O$ (210 mg, 1.7 mmol, commercially available) and N,N-diisopropylethylamine (220 mg, 1.7 mmol) were added. The temperature was increased to 65° C. After the reaction was complete in 2 h, suction filtration through Celite® was performed. The solid was washed with DCM (20 ml), the mother liquor was concentrated, and 22 mg of pure Compound No. 17 (a white solid, 11%) was obtained by high-performance liquid preparative chromatography. $^1$H-NMR (400 MHz, DMSO) δ 8.26 (d, J=8.5 Hz, 1H), 7.67 (d, J=8.5 Hz, 1H), 7.59-7.48 (m, 3H), 7.41 (dt, J=10.3, 2.5 Hz, 1H), 7.24-7.19 (m, 2H), 7.03 (dd, J=8.5, 2.3 Hz, 1H), 6.36-6.32 (m, 1H), 2.20-1.91 (m, 8H). LCMS: Calculated 573.1, found 574.1 ([M+H]$^+$).

Synthesis of Compound No. 18

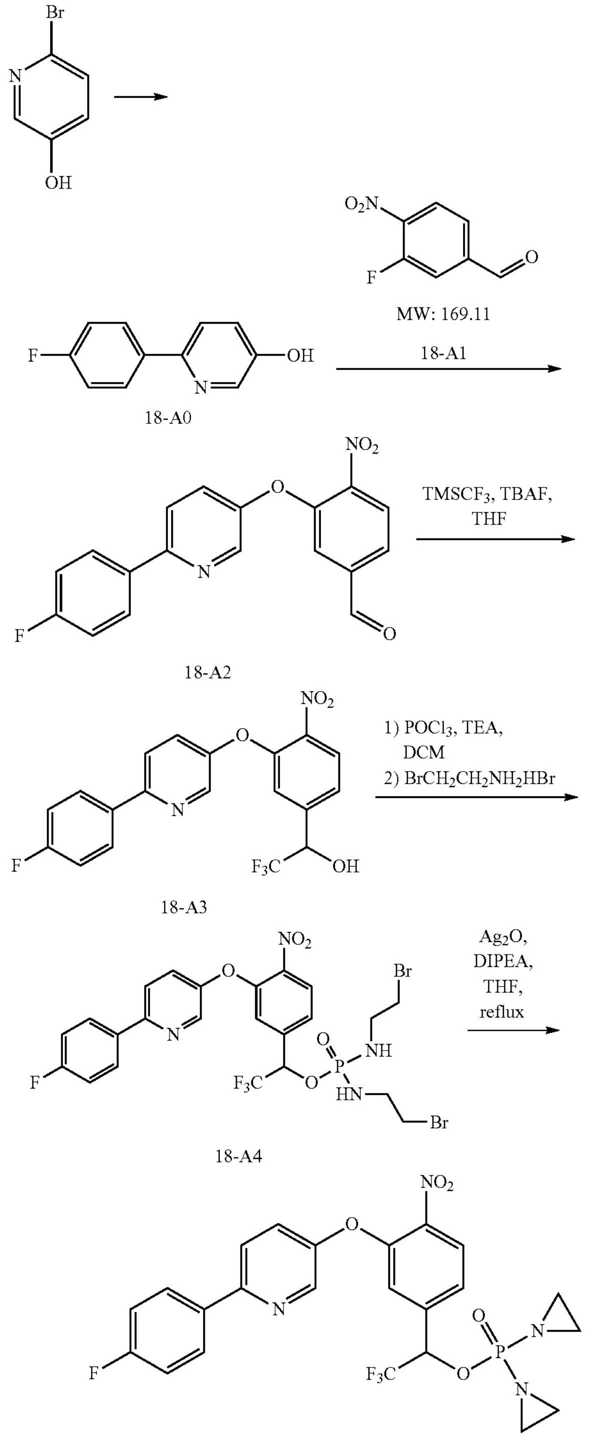

18

Under the protection of nitrogen, 2-bromo-5-hydroxypyridine (3.0 g, 17.2 mmol, from Xingtai All Fine) and p-fluorophenylboronic acid (18-A0, 2.7 g, 19.0 mmol, commercially available) were dissolved in a mixed solvent (60 ml, dioxane:water=9:1) of dioxane and water. After that, potassium carbonate (4.7 g, 34.4 mmol) was added. Evacuation and filling with gas were performed three times. After palladium acetate (193 mg, 0.86 mmol, commercially available), and triphenylphosphine (225 mg, 0.86 mmol, commercially available) were added, evacuation and filling with gas were performed three times again. The temperature was increased to 100° C. and stirring was performed overnight. After the completion of the reaction, the temperature was reduced to room temperature. Suction filtration through Celite® was performed, and washing was performed with EA. The mother liquor was concentrated. 15 mL of water was added. Extraction was performed with EA (50 mlx3) followed by washing with water (10 mlx3) and washing with brine, drying, concentration and column separation (200-300 mesh silica gel, n-heptane:EA=15:1) to obtain a product (1.2 g, 36.9%) as a white solid. $^1$H-NMR (400M, DMSO-$d_6$): δ ppm 10.03 (s, 1H), 8.20 (d, J=2.7 Hz, 1H), 8.00 (dd, J=8.8, 5.6 Hz, 2H), 7.78 (d, J=8.6 Hz, 1H), 7.32-7.18 (m, 3H). LCMS: Calculated 189.1, found 190.2 ([M+H]$^+$).

Under the protection of nitrogen, 18-A1 (600 mg, 3.55 mmol) and 18-A0 (806 mg, 4.26 mmol) were dissolved in acetonitrile (15 ml). After that, potassium carbonate (980 mg, 7.1 mmol, commercially available) was added. The temperature was increased to 85° C. and stirring was performed for 2 h before the completion of the reaction. The temperature was reduced to room temperature. Suction filtration was performed. The mother liquor was concentrated, and subjected to column separation (200-300 mesh silica gel, n-heptane:EA=10:1) to obtain the product 18-A2 (760 mg, 63.3%) as a light yellow solid. $^1$H-NMR (400 MHz, DMSO-$d_6$): δ ppm 10.03 (s, 1H), 8.59 (d, J=2.8 Hz, 1H), 8.31 (d, J=8.3 Hz, 1H), 8.19-8.11 (m, 2H), 8.07 (d, J=8.7 Hz, 1H), 7.90 (dd, J=8.3, 1.6 Hz, 1H), 7.78-7.70 (m, 2H), 7.37-7.26 (m, 2H). LCMS: Calculated 338.1, found 339.0 ([M+H]$^+$).

Under the protection of nitrogen, 18-A2 (700 mg, 2.07 mmol) was dissolved in anhydrous THF (10 mL), and then (trifluoromethyl)-trimethylsilane (500 mg, 3.52 mmol) was added dropwise. The temperature was reduced to 0° C., and TBAF (0.03 mL, 1 MinTHF) was added dropwise. The temperature was kept at 0° C. for 1.5 h until the completion of the reaction. 3N hydrochloric acid (2 mL) was added dropwise. The temperature was naturally increased to room temperature. Stirring was performed for 1 h. 5 mL of water was added. Extraction was performed with DCM (10 mlx3) followed by washing with water (5 mLx3), drying, concentration and column separation (200-300 mesh silica gel, n-heptane:EA=15:1 to 10:1) to obtain a product (550 mg, 65.1%) as a yellow oil. $^1$H-NMR (400 MHz, DMSO-$d_6$): δ ppm 8.52 (d, J=2.9 Hz, 1H), 8.19 (d, J=8.5 Hz, 1H), 8.16-8.10 (m, 2H), 8.06 (d, J=8.8 Hz, 1H), 7.64 (dd, J=8.8, 2.9 Hz, 1H), 7.55 (dd, J=8.7, 3.3 Hz, 1H), 7.38 (s, 1H), 7.36-7.28 (m, 2H), 7.18 (dd, J=5.8, 3.4 Hz, 1H), 5.43-5.34 (m, 1H). LCMS: Calculated 408.1, found 409.2 [M+H]$^+$).

Under the protection of nitrogen, phosphorus oxychloride (414 mg, 2.70 mmol, commercially available) was added dropwise to anhydrous DCM (10 mL). The temperature was reduced to −40° C. DCM solution (4 mL) of 18-A3 (550 mg, 1.35 mmol) was added dropwise, then triethylamine (342 mg, 3.36 mmol) was added dropwise, and the temperature was kept at a temperature ranging from −40° C. to −35° C. for 2 h. As monitored by LC-LCMS, 18-A3 disappeared and was converted to an intermediate. 2-Bromoethylamine hydrobromide (2.2 g, 10.8 mmol) was added at −40° C., and then DCM solution (2 ml) of triethylamine (1.1 g, 10.8 mmol) was added dropwise. The temperature was kept at −40° C. for 1 h, and the intermediate was completely converted. The temperature was naturally increased to 0° C., and saturated ammonium chloride aqueous solution (5 mL) was added dropwise. Extraction was performed with DCM (10 mL×3) followed by washing with pure water (3 mL×3), drying, concentration and column separation (200-300 mesh silica gel, n-heptane:EA=1:1 to 100% EA) to obtain a product (520 mg, 55.0%) as a white solid. $^1$H-NMR (400M, $CDCl_3$): δ ppm 8.49 (d, J=2.7 Hz, 1H), 8.06 (dd, J=8.4, 2.7 Hz, 1H), 8.01-7.94 (m, 2H), 7.77 (d, J=8.7 Hz, 1H), 7.54-7.48 (m, 1H), 7.43 (d, J=8.3 Hz, 1H), 7.26-7.24 (m, 1H), 7.18 (t, J=8.7 Hz, 2H), 5.69 (dq, J=12.3, 6.2 Hz, 1H), 3.49-3.16 (m, 8H). LCMS: Calculated 700.0, found 700.9 ([M+H]$^+$).

Under the protection of nitrogen, 18-A4 (520 mg, 0.743 mmol) was dissolved in THF (15 ml), and then silver oxide (1.03 g, 4.46 mmol, commercially available) and DIPEA (580 mg, 4.46 mmol) were added. The temperature was increased to 65° C. and stirring was performed for 3 h. After the reaction was complete, the temperature was reduced to room temperature. Suction filtration through Celite® was performed. The solid was washed with DCM, and the mother liquor was concentrated. Pure Compound No. 18 (106.7 mg, 26.7%) was obtained as a white solid by high-performance liquid preparative chromatography. $^1$H-NMR (400 MHz, MeOD): δ ppm 8.43 (d, J=2.9 Hz, 1H), 8.16 (d, J=8.5 Hz, 1H), 8.07-7.97 (m, 2H), 7.92 (d, J=8.8 Hz, 1H), 7.65-7.54 (m, 2H), 7.46 (s1H), 7.24-7.19 (m, 2H), 6.13-6.03 (m, 1H), 2.26-2.08 (m, 8H). LCMS: Calculated 538.1, found 539.1 ([M+H]$^+$).

Synthesis of Compound No. 19

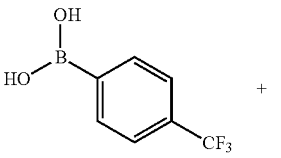

19-A1

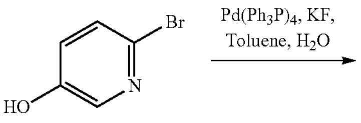

19-A2

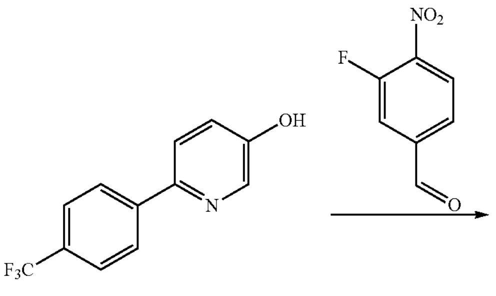

19-A3

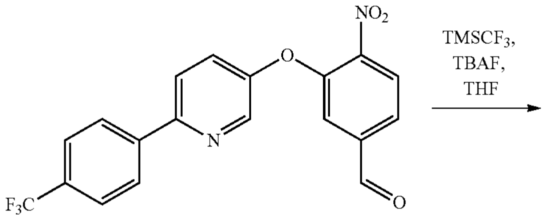

19-A4

-continued

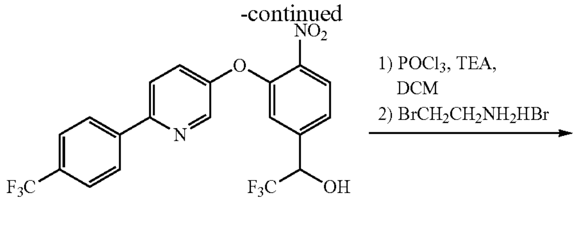

19-A5

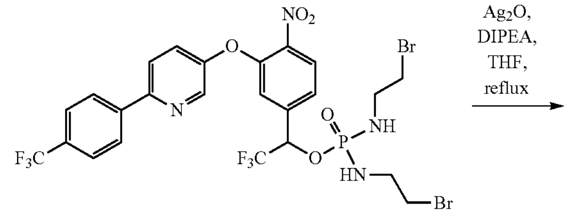

19-A6

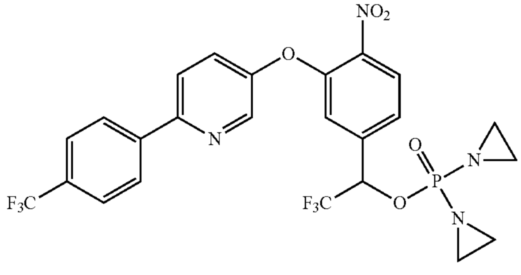

19

Under the protection of nitrogen, 19-A1 (500 mg, 2.65 mol, commercially available), 19-A2 (460 mg, 2.65 mmol, commercially available), tetrakistriphenylphosphine palladium (373 mg, 0.3 mmol) and potassium fluoride (300 mg, 5.2 mmol) were dissolved in toluene (10 ml) and water (1 mL). The temperature was increased to 80° C. and stirring was performed for overnight After the completion of the reaction, suction filtration through Celite® was performed followed by concentration. The sample was mixed and subjected to column chromatography separation (100-200 mesh silica gel, n-heptane:EA=10:1) to obtain the product 19-A3 (600 mg, 94.7%) as a white solid. $^1$H-NMR (300 MHz, DMSO) δ 10.24 (0, H), 8.26 (d, J=2.4 Hz, H), 8.19 (d, J=8.1 Hz, 2H), 7.91 (d, 0.8.7 Hz, H), 7.78 (d, J=8.1 Hz, 2H), 7.29 (dd, J=8.6, 2.7 Hz, 1H). LCMS: Calculated 239.0, found 240.0 ([M+H]$^+$).

Under the protection of nitrogen, 19-A3 (870 mg, 2.9 mmol), and 3-fluoro-4-nitrobenzaldehyde (490 mg, 2.9 mmol, commercially available) were dissolved in ACN (8 ml). Potassium carbonate (830 mg, 6 mmol) was added. The temperature was increased to 80° C. and stirring was performed for 4 h. After the completion of the reaction, suction filtration through Celite® was performed followed by concentration. The sample was mixed and subjected to column chromatography separation (100-200 mesh silica gel, n-heptane:EA=10:1) to obtain the product 19-A4 (640 mg) as a white solid. $^1$HNMR (300 MHz, $CDCl_3$) δ 10.03 (s, 1H), 8.57 (d, J=2.7 Hz, DH), 8.15-8.12 (d, 3H), 7.87-7.75 (m, 4H), 7.60-7.51 (m, 2H). LCMS: Calculated 388.0, found 389.1 ([M+H]$^+$).

Under the protection of nitrogen, 19-A4 (640 mg, 1.64 mmol) and trifluoromethyltrimethylsilane (430 mg, 3 mmol, commercially available) were dissolved in THF (5 mL). At 0° C., THF solution (0.1 mL, 0.1 mmol, 1M, commercially available) of tetrabutylammonium fluoride was added dropwise. The temperature was maintained for 6 h. 1N hydrochloric acid (2 mL) was added and stirred for 10 min THF was removed by concentration. Water (10 ml) was added to the crude product and extraction was performed with DCM (20 ml). The organic phase was separated and concentrated, and the sample was mixed. The crude product was isolated by column chromatography (100-200 mesh silica gel, n-heptane:EA=10:1) to obtain a product (640 mg, 85.2%) as a light yellow solid. $^1$H-NMR (300 MHz, DMSO) δ 8.59 (d, J=2.7 Hz, 1H), 8.30 (d, J=7.5 Hz, 2H), 8.19 (t, J=9.2 Hz, 2H), 7.86 (d, J=8.5 Hz, 2H), 7.72-7.65 (m, 1H), 7.59-7.56 (m, 1H), 7.43 (s, 1H), 7.20 (d, J=5.8 Hz, 1H), 5.39-5.37 (m, 1H). LCMS: Calculated 458.0, found 459.0 ([M+H]$^+$).

Under the protection of nitrogen, $POCl_3$ (200 mg, 1.3 mmol) was added dropwise to ultra-dry DCM (5 ml). The temperature was reduced to −30° C. DCM (5 ml) solution of 19-A5 (300 mg, 0.65 mmol) was added dropwise, then TEA (270 mg, 2.6 mmol) was added dropwise, and the temperature was kept at −30° C. for 6 h until the raw materials disappeared completely. 2-Bromoethylamine hydrobromide (1.1 g, 5.2 mmol) was added at −30° C., and then TEA (530 mg, 5.2 mmol) was added dropwise. After the completion of the reaction, the temperature was reduced to 0° C. $NH_4Cl$ saturated solution (10 ml) was added. Extraction was performed with DCM (15 ml×2) followed by washing with water (5 mL×4), drying and concentration to obtain 200 mg of a crude product, which, as a yellow solid, was directedly used in the reaction in the next step. $^1$H-NMR (400 MHz, $CDCl_3$) δ 8.46 (d, J=2.6 Hz, 1H), 8.07-7.99 (m, 3H), 7.78-7.75 (m, 1H), 7.68 (d, J=8.2 Hz, 2H), 7.48-7.33 (m, 3H), 5.65-5.61 (m, 1H), 3.51-3.04 (m, 10H). LCMS: Calculated 747.9, found 748.9 ([M+H]$^+$).

Under the protection of nitrogen, 19-A6 (150 mg, 0.23 mmol) was dissolved in THF (10 ml), and $Ag_2O$ (170 mg, 1.38 mmol, commercially available) and N,N-diisopropylethylamine (163 mg, 1.38 mmol) were added. The temperature was increased to 65° C. After the reaction was complete in 2 h, suction filtration through Celite® was performed. The solid was washed with DCM (20 ml), the mother liquor was concentrated, and a pure product (41 mg, 36%) was obtained as a white solid by high-performance liquid preparative chromatography. $^1$H-NMR (400 MHz, DMSO) δ 8.61 (d, J=2.8 Hz, 1H), 8.31 (d, J=8.2 Hz, 2H), 8.27 (d, J=8.5 Hz, 1H), 8.21 (d, J=8.8 Hz, 1H), 7.87 (d, J=8.4 Hz, 2H), 7.72 (dd, J=8.8, 2.9 Hz, 1H), 7.65 (d, J=8.5 Hz, 1H), 7.56 (s, 1H), 6.32-6.28 (m, 1H), 2.17-1.90 (m, 8H). LCMS: Calculated 588.1, found 589.1 ([M+H]$^+$).

Synthesis of Compound No. 20

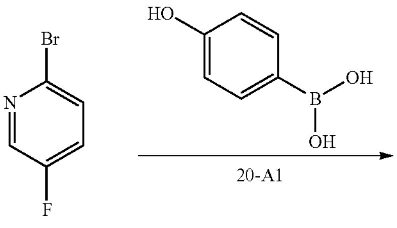

20-A0

20-A1

-continued

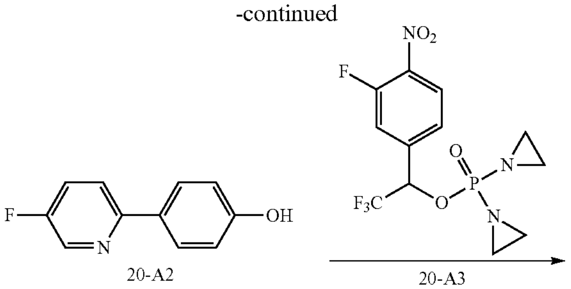

20-A2

20-A3

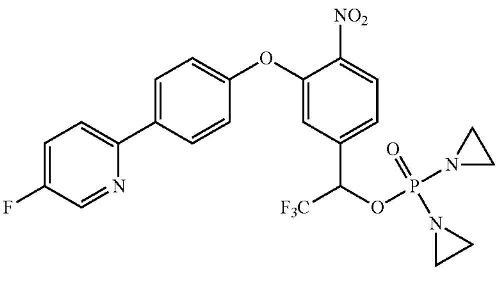

20

Under the protection of nitrogen, 2-bromo-5-hydroxypyridine (1.5 g, 8.52 mmol, commercially available) and p-hydroxyphenylboronic acid (1.4 g, 10.23 mmol, commercially available) were added to a mixed liquid of DME (33 mL) and $H_2O$ (7 mL). Evacuation and filling with nitrogen were performed 3 times. After $Pd(PPh_3)_4$ (300 mg, 0.26 mmol, commercially available) and $Na_2CO_3$ (1.8 g, 17.05 mmol) were added, evacuation and filling with nitrogen were performed three times again. The temperature was increased to 80° C. to carry out the reaction. The reaction was monitored for 2.5 h before it was complete. The temperature was reduced to room temperature. Extraction was performed with EtOAc (50 ml×3). The organic phase was washed with water and washed with brine, and was subjected to column separation (200-300 mesh silica gel, n-heptane:EA=12:1 to 9:1) to obtain a product (1.4 g, yield=86.8%) as a white solid. $^1$H-NMR (300 MHz, MeOD): δ ppm 8.43 (d, J=2.7 Hz, 1H), 7.81-7.77 (m, 3H), 7.64-7.58 (m, 1H), 6.87 (d, J=8.7 Hz, 2H). LCMS: Calculated 189.1, found 190.1 ([M+H]$^+$).

Under the protection of nitrogen, 20-A3 (i.e., Compound No. 46, 100 mg, 0.27 mmol) was dissolved in acetone (15 ml), and then 20-A2 (102 mg, 0.54 mmol), and $Cs_2CO_3$ (309 mg, 0.95 mmol) were stirred for 2 h at room temperature. After the reaction was complete, suction filtration through Celite® was performed. The solid was washed with acetone, and the mother liquor was concentrated. Pure Compound No. 20 (17 mg, 11.7%) was obtained as a brown solid by high-performance liquid preparative chromatography. $^1$H-NMR (400 MHz, MeOD) δ8.52 (d, J=2.9 Hz, 1H), 8.10 (d, J=8.5 Hz, 1H), 8.06 (d, J=8.8 Hz, 2H), 7.92 (dd, J=8.8, 4.3 Hz, 1H), 7.68 (dt, J=8.6, 2.9 Hz, 1H), 7.54 (d, J=8.6 Hz, 1H), 7.37 (s, 1H), 7.19 (d, J=8.8 Hz, 2H), 6.06-5.99 (m, 1H), 2.27-1.97 (m, 8H). LCMS: Calculated 538.1, found 539.1 ([M+H]$^+$).

Synthesis of Compound No. 21

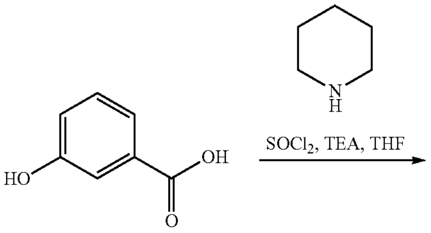

21-A1

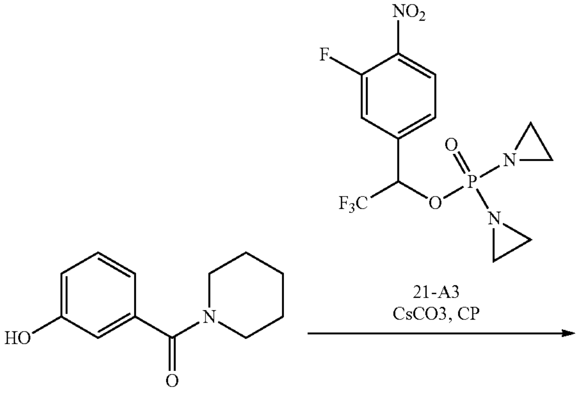

21-A2

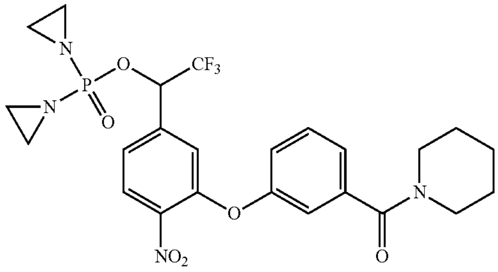

21

Under the protection of nitrogen, 21-A1 (2.0 g, 14.5 mmol) and thionyl chloride (8 ml) were stirred at room temperature for 1 h, and thionyl chloride was removed by spinning. 10 ml of THF was added, the system was cooled to 0° C., and a mixture of piperidine (1.85 g, 21.8 mmol) and TEA (2.2 g, 21.8 mmol) was added. After completion, the temperature of the system was naturally raised to room temperature. Monitoring was performed for 1 h before the completion of the reaction. The system was dissolved in EtOAc (50 ml) and washed with $H_2O$ (30 ml×5). The organic phase was dried and concentrated, and was subjected to column separation (200-300 mesh silica gel, n-heptane:EA=1:1 to 0:1) to obtain a product (720 mg, yield=24.3%) as a white solid. $^1$H-NMR (400 MHz, DMSO-$d_6$): δ ppm, 9.64 (s, 1H) 7.23 (t, J=8.0 Hz, 1H), 6.79-6.82 (m, 1H), 6.73 (d, J=7.6 Hz, 1H), 6.70 (d, J=1.2 Hz, 1H) 3.54 (m, 2H) 3.26 (m, 2H), 1.61-1.50 (m, 6H). LCMS: Calculated 205.1, found 206.2 ([M+H]$^+$).

Under the protection of nitrogen, 21-A2 (60 mg, 0.25 mmol) was dissolved in acetone (10 ml), and then 21-A3 (i.e., Compound No. 46, 55.6 mg, 0.25 mmol), and $Cs_2CO_3$ (245 mg, 0.75 mmol) were added and stirred for 2.5 h at room temperature. After the reaction was complete, suction filtration through Celite® was performed. The solid was washed with acetone, and the mother liquor was concentrated. Pure Compound No. 21 (25.0 mg, 16.9%) was obtained as an off-white solid by high-performance liquid preparative chromatography. $^1$H-NMR (400 MHz, $CD_3OD$): δ ppm, 8.21 (d, J=8.0 Hz, 1H), 7.60 (d, J=8.0 Hz, 1H), 7.53 (t, J=8.0 Hz, 1H), 7.41 (s, 1H), 7.24 (d, J=8.0 Hz, 1H) 7.20 (dd, J=8.0, 2.4 Hz, 1H), 7.05 (s, 1H), 6.33-6.25 (m, 1H), 3.55 (m, 2H), 3.25 (m, 2H), 2.15-1.93 (m, 8H), 1.59-1.52 (m, 6H). LCMS: Calculated 554.2, found 555.2 ([M+H]$^+$).

Synthesis of Compound No. 22

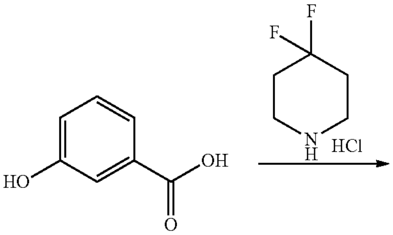

22-A1

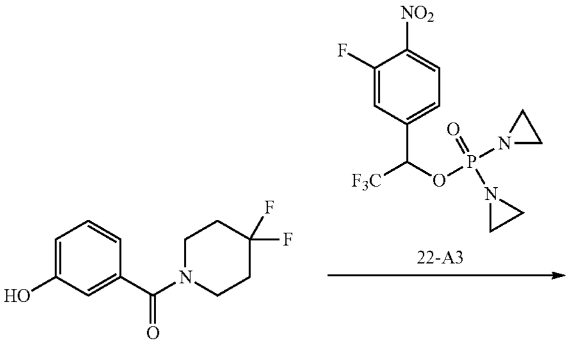

22-A2

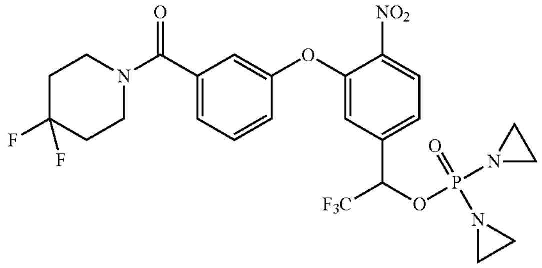

22

Under the protection of nitrogen, 22-A1 (0.2 g, 1.45 mmol), and $T_3P$ solution (propylphosphonic anhydride coupling reagent, CAS:68957-94-8, 50% EA solution) were dissolved in 5 ml of DCM. 4,4-Difluoropiperidine (0.25 g, 1.6 mmol) was added and stirred at room temperature. Monitoring was performed for 2 h before the completion of the reaction. The system was dissolved in DCM (20 ml) and washed with water (10 ml×5), and the organic phase was dried, concentrated, and subjected to column separation (200-300 mesh silica gel, n-heptane:EA=1:1) to obtain a product (190 mg, yield=54.4%) as a white solid. $^1$H-NMR (400 MHz, $CDCl_3$): δ ppm 6.94-6.89 (m, 2H), 6.87 (d, J=8.0 Hz, 1H), 6.36 (s, 1H), 3.87 (m, 2H), 3.56 (m, 2H), 2.04-1.97 (m, 4H). LCMS: Calculated 241.1, found 242.1 ([M+H]$^+$).

Under the protection of nitrogen, 22-A2 (60 mg, 0.25 mmol) was dissolved in acetone (10 ml), and then 22-A3

(i.e., Compound No. 46, 55.6 mg, 0.25 mmol), and $Cs_2CO_3$ (245 mg, 0.75 mmol) were stirred for 2.5 h at room temperature. After the reaction was complete, suction filtration through Celite® was performed. The solid was washed with acetone, and the mother liquor was concentrated. Pure Compound No. 22 (25.0 mg, 16.9%) was obtained as a light yellow solid by high-performance liquid preparative chromatography. $^1$H-NMR (400 MHz, MeOD): δ ppm 8.21 (d, J=8.4 Hz, 1H), 7.60-7.54 (m, 2H), 7.40 (s, 1H), 7.33 (d, J=8.0 Hz, 1H), 7.25-7.21 (m, 2H), 6.33-6.26 (m, 1H), 3.68 (m, 2H), 3.40 (m, 2H) 2.15-1.93 (m, 12H). LCMS: Calculated 590.1, found 591.1 ([M+H]$^+$).

Synthesis of Compound No. 23

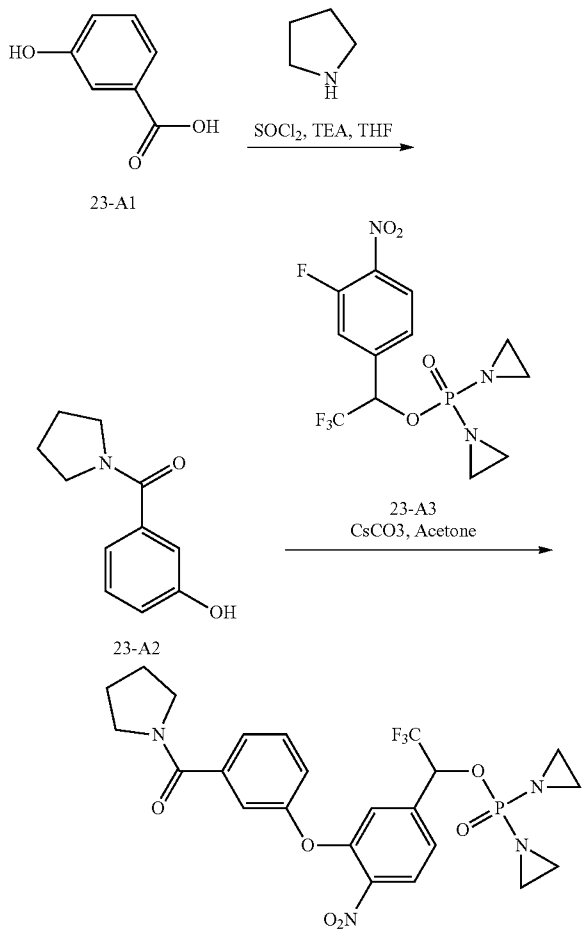

23-A1

23-A2

23

Under the protection of nitrogen, 23-A1 (2.0 g, 14.5 mmol) and thionyl chloride (8 ml) were stirred at room temperature for 1 h, and thionyl chloride was removed by spinning. 10 ml of THF was added, the system was cooled to 0° C., and a mixture of tetrahydropyrrole (1.5 g, 21.8 mmol) and TEA (2.2 g, 21.8 mmol) was added. After completion, the temperature of the system was naturally raised to room temperature. Monitoring was performed for 1 h before the completion of the reaction. The system was dissolved in EtOAc (40 ml) and washed with $H_2O$ (40 ml×5). The organic phase was dried and concentrated, and was subjected to column separation (200-300 mesh silica gel, n-heptane:EA=1:1 to EA) to obtain a crude product (850 mg, 30.7%, the content of the crude product being 80%) as a colorless oil.

Under the protection of nitrogen, 23-A2 (103 mg, 0.54 mmol) was dissolved in acetone (10 ml), and then 23-A3 (i.e., Compound No. 46, 120 mg, 0.54 mmol), and $Cs_2CO_3$ (265 mg, 0.81 mmol) were stirred for 2.5 h at room temperature. After the reaction was complete, suction filtration through Celite® was performed. The solid was washed with acetone, and the mother liquor was concentrated. Pure Compound No. 23 (35.0 mg, 18.8%) was obtained as an off-white solid by high-performance liquid preparative chromatography. $^1$H-NMR (400 MHz, MeOD): δ ppm 8.20 (d, J=8.0 Hz, 1H), 7.59 (d, J=8.0 Hz, 1H) 7.53 (t, J=8.0 Hz, 1H) 7.39-7.38 (m, 2H), 7.24-7.21 (m, 2H), 6.32-6.25 (m, 1H). 3.43 (t, J=6.8 Hz, 2H) 3.36-3.34 (m, 2H) 1.92-2.14 (m, 8H) 1.84-1.77 (m, 4H). LCMS: Calculated 540.1, found 541.1 ([M+H]$^+$).

Synthesis of Compound No. 24

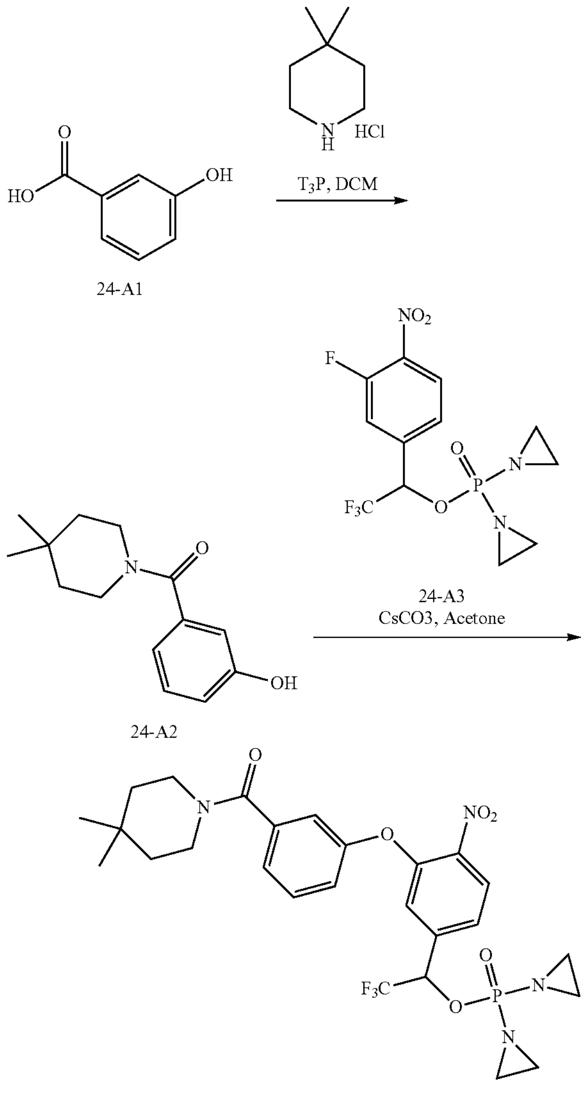

24-A1

24-A2

24

Under the protection of nitrogen, 24-A1 (500 mg, 3.6 mmol, commercially available) and $T_3P$ (4.6 g, 14.4 mmol, 50% EA solution) were dissolved 10 ml of DCM, and 4, 4-dimethylpiperidine hydrochloride (540 mg, 3.6 mmol, from Shanghai Anmike) was added and stirred at room temperature. Monitoring was performed for 2 h before the completion of the reaction. The system was dissolved in DCM (20 ml) and washed with $H_2O$ (10 ml×5). The organic phase was dried and concentrated, and was subjected to column separation (200-300 mesh silica gel, n-heptane: EA=1:1-EA) to obtain a product (600 mg, yield=71.4%) as a light yellow solid. $^1$H-NMR (400 MHz, MeOD): δ ppm 7.20 (t, J=8.0 Hz, 1H), 6.82-6.81 (m, 1H), 6.80-6.75 (m, 1H), 6.73-6.72 (m, 1H), 3.66 (m, 2H) 3.34 (s, 2H), 1.41 (m, 2H). 1.30-1.29 (m 2H), 0.97 (s, 6H). LCMS: Calculated 233.1, found 234.1 ([M+H]$^+$).

Under the protection of nitrogen, 24-A2 (103 mg, 0.54 mmol) was dissolved in acetone (10 ml), and then 24-A3 (i.e., Compound No. 46, 120 mg, 0.54 mmol), and $Cs_2CO_3$ (265 mg, 0.81 mmol) were stirred for 2.5 h at room temperature. After the reaction was complete, suction filtration through Celite® was performed. The solid was washed with acetone, and the mother liquor was concentrated. Pure Compound No. 24 (35.0 mg, 18.8%) was obtained as an off-white solid by high-performance liquid preparative chromatography. $^1$H-NMR (400 MHz, DMSO): δ ppm 8.21 (d, J=8.4 Hz, 1H), 7.59 (d, J=8.4 Hz, 1H), 7.53 (t, J=8.0 Hz, 1H), 7.40 (s, 1H). 7.24 (d, J=76 Hz, 1H) 7.19 (dd/=:76, 2.4 Hz, 1H), 7.06-7.07 (m, 1H), 6.32-6.27 (m, 1H), 3.57 (m, 2H), 3.26 (m, 2H) 2.13-1.94 (m, 8H). 1.23 (m, 2H) 1.14 (m, 2H), 0.94 (s, 6H). LCMS: Calculated 582.2, found 583.2 ([M+H]$^+$).

Synthesis of Compound No. 25

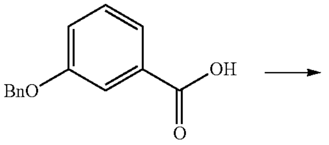

25-A1

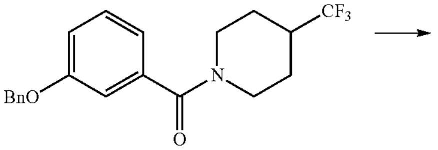

25-A2

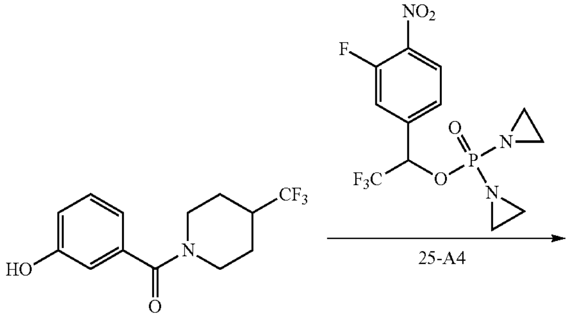

25-A3

-continued

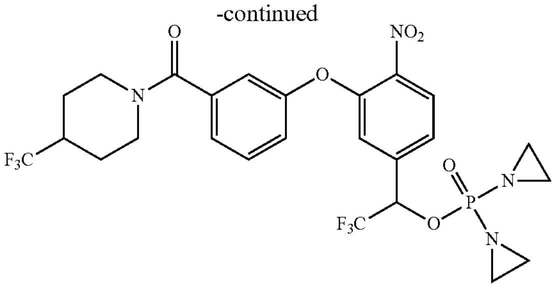

25

Under the protection of nitrogen, 25-A1 (500 mg, 2.19 mmol) and 4-(trifluoromethyl)piperidine (1.0 g, 6.57 mmol, commercially available) were added to DCM (10 ml), and then $T_3P$ (5.6 g, 8.77 mmol, 50% in EtOAc, commercially available) was added dropwise to the system. Then, the system was cooled to 5° C., and DIEA (1.2 g, 8.77 mmol, commercially available) was added dropwise to the system. After completion, the temperature was naturally raised to room temperature. Monitoring was performed for 2 h before the completion of the reaction. The solvent was removed by concentration followed by dissolving in EtOAc (20 ml) and washing with $H_2O$ (20 ml×5). The organic phase was dried and concentrated to obtain a product (790 mg, yield=98.9%) as a white solid. $^1$H-NMR (400 MHz, MeOD): δ ppm 7.42 (d, J=7.1 Hz, 2H), 7.40-7.33 (m, 3H), 7.32-7.26 (m, 1H), 7.13-7.10 (m, 1H), 6.98-6.95 (m, 2H), 5.14 (s, 2H), 4.70 (m, 1H), 3.75-7.72 (m, 1H), 3.08-3.08 (m, 1H), 2.84 (m, 1H), 2.54-2.46 (m, 1H), 1.98 (m, 1H), 1.81-1.76 (m, 1H), 1.55-1.53 (m, 1H), 1.44-1.35 (m, 1H). LCMS: Calculated 363.1, found 364.1 ([M+H]$^+$).

Under the protection of nitrogen, 25-A2 (780 mg, 2.15 mmol) and $Pd(OH)_2$ (90 mg, commercially available) were added to EtOH (10 ml). Evacuation and filling with nitrogen were performed three times. After evacuation and filling with hydrogen were performed three times, the temperature was increased to 35° C. overnight. The next day, monitoring was performed until the completion of the reaction. Suction filtration through Celite® was performed, washing was performed with DCM. The mother liquor was concentrated to obtain 25-A3 (390 mg, yield=66.6%) as a white solid. $^1$H-NMR (400 MHz, MeOD): δ ppm 77.26 (t, J=7.9 Hz, 1H), 6.87 (dd, J=8.1, 2.3 Hz, 1H), 6.83 (d, J=7.5 Hz, 1H), 6.80-6.76 (m, 1H), 4.70 (m, 1H), 3.84 (m, 1H), 3.13 (m, 1H), 2.85 (m, 1H), 2.57-2.47 (m, 1H), 2.06-1.79 (m, 2H), 1.50-1.46 (m, 2H). LCMS: Calculated 273.1, found 274.2 ([M+H]+).

Under the protection of nitrogen, 25-A4 (i.e., Compound No. 46, 100 mg, 0.27 mmol) was dissolved in acetone (10 ml), and then 25-A3 (148 mg, 0.54 mmol) and $Cs_2CO_3$ (309 mg, 0.95 mmol, commercially available) were stirred for 2 h at room temperature before the completion of the reaction. Post-treatment was carried out as follows. Suction filtration through Celite® was performed, washing was performed with acetone, and the mother liquor was concentrated. Pure Compound No. 25 (40.8 mg, 24.2%) was obtained as a yellow solid by high-performance liquid preparative chromatography. $^1$H-NMR (400 MHz, DMSO) δ 8.20 (d, J=8.5 Hz, 1H), 7.59 (d, J=8.6 Hz, 1H), 7.54 (t, J=7.9 Hz, 1H), 7.39 (s, 1H), 7.28 (d, J=7.6 Hz, 1H), 7.22 (dd, J=8.2, 2.0 Hz, 1H), 7.13 (s, 1H), 6.28 (dq, J=12.9, 6.4 Hz, 1H), 4.53 (m, 1H), 3.60 (m, 1H), 3.08 (m, 1H), 2.78 (m, 1H), 2.71-2.57 (m, 1H), 2.13-1.92 (m, 8H), 1.87-1.76 (m, 2H), 1.39-1.37 (m, 2H). LCMS: Calculated 622.1, found 623.1 ([M+H]$^+$).

Synthesis of Compound No. 26

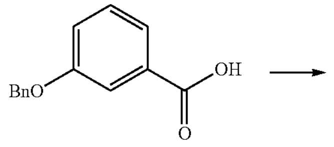

26-A1

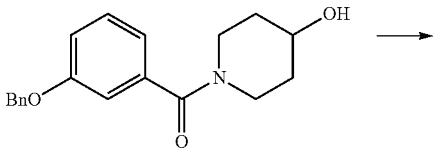

26-A2

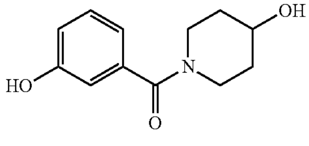

26-A3

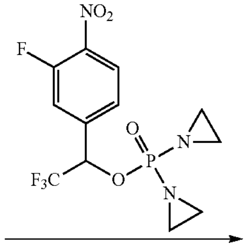

26-A4

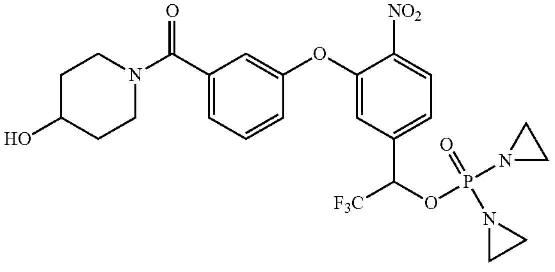

26

Under the protection of nitrogen, 26-A1 (1.0 g, 4.38 mmol) and p-hydroxy piperidine (1.3 g, 13.12 mmol) were added to DCM (20 ml), and then $T_3P$ (11.2 g, 8.77 mmol, 50% in EtOAc) was added dropwise to the system. The system was cooled to 5° C., and then DIEA (2.4 g, 17.54 mmol, commercially available) was added dropwise to the system. After completion, the temperature was naturally raised to room temperature. Monitoring was performed for 5 h before the completion of the reaction. Post-treatment was carried out as follows. The system was concentrated, dissolved in in EtOAc (40 ml) and washed with $H_2O$ (40 ml×5). The organic phase was dried and concentrated and was subjected to column separation (200-300 mesh silica gel, n-heptane:EA=1:1-0:1) to obtain 26-A2 (920 mg, yield=67.4%) as a colorless oil. $^1$H-NMR (400 MHz, MeOD): δ ppm 7.43 (d, J=8.0 Hz, 2H), 7.38 (t, J=7.6 Hz, 3H), 7.32-7.28 (m, 1H), 7.10 (d, J=8.4 Hz, 1H), 6.98 (m, 1H), 5.95 (d, J=8.0 Hz, 1H), 5.13 (s, 2H), 4.14 (s, 1H), 3.89-3.85 (m, 1H), 3.56 (s, 1H), 3.17 (s, 1H), 1.92 (s, 1H), 1.74 (s, 1H), 1.54 (s, 1H), 1.40 (s, 1H), 1.03 (s, 1H). LCMS: Calculated 311.2, found 312.2 ([M+H]$^+$).

Under the protection of nitrogen, 26-A2 (900 mg, 2.89 mmol) and PdOH catalyst (121 mg) were added to EtOH (10 ml). Evacuation and filling with nitrogen were performed three times. After evacuation and filling with hydrogen were performed three times, the temperature was increased to 35° C. overnight The next day, monitoring was performed until the completion of the reaction. Post-treatment was carried out as follows. Under the protection of nitrogen, suction filtration through Celite® was performed, and washing was performed with DCM. The mother liquor was concentrated to obtain the product 26-A3 (460 mg, yield=71.9%) as a colorless oily liquid. $^1$H-NMR (400 MHz, MeOD): δ ppm 7.26 (d, J=8.0 Hz, 1H), 6.87 (dd, J=8.4, 2.0 Hz, 1H), 6.82 (d, J=7.2 Hz, 1H), 6.79 (d, J=2.0 Hz, 1H), 4.16 (m, 1H), 3.91-3.85 (m, 1H), 3.62 (m, 2H), 3.31-3.22 (s, 1H), 1.80-1.64 ((m, 1H), 1.54-1.45 (m, 2H). LCMS: Calculated 221.1, found 222.1 ([M+H]$^+$).

Under the protection of nitrogen, 26-A4 (i.e., Compound No. 46, 100 mg, 0.27 mmol) and 26-A3 (120 mg, 0.54 mmol) were dissolved in acetone (10 ml), and then $Cs_2CO_3$ (265 mg, 0.81 mmol) was added and stirred for 2.5 h at room temperature before the completion of the reaction. Post-treatment was carried out as follows. Suction filtration through Celite® was performed, washing was performed with acetone, and the mother liquor was concentrated. Pure Compound No. 26 (29.0 mg, 18.8%) was obtained as an off-white solid by high-performance liquid preparative chromatography. $^1$H-NMR (400 MHz, DMSO) δ 8.20 (d, J=8.5 Hz, 1H), 7.59 (d, J=8.5 Hz, 1H), 7.53 (t, J=7.9 Hz, 1H), 7.40 (s, 1H), 7.25 (d, J=7.7 Hz, 1H), 7.20 (dd, J=7.9, 2.2 Hz, 1H), 7.07 (d, J=1.4 Hz, 1H), 6.29 (dq, J=13.0, 6.4 Hz, 1H), 4.77 (d, J=3.7 Hz, 1H), 3.95 (s, 1H), 3.72-3.71 (m, 1H), 3.44 (m, 1H), 3.20-3.11 (m, 2H), 2.23-1.90 (m, 8H), 1.76-1.66 (m, 2H), 1.52-1.18 (m, 2H). LCMS: Calculated 570.1, found 571.2 ([M+H]$^+$).

Synthesis of Compound No. 27

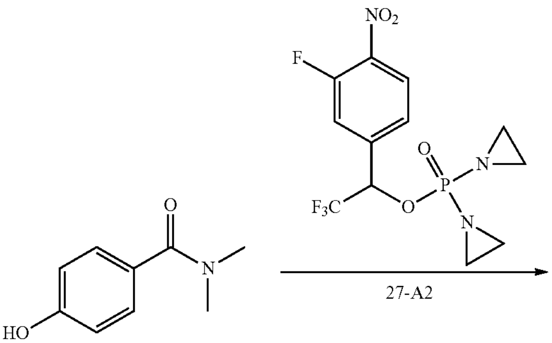

27-A2

27-A1

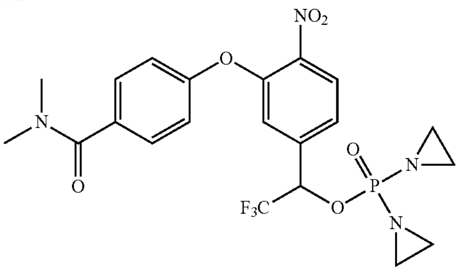

27

Under the protection of nitrogen, 27-A2 (i.e., Compound No. 46, 100 mg, 0.27 mmol) and 27-A1 (89 mg, 0.54 mmol) were dissolved in acetone (10 ml), and then $Cs_2CO_3$ (265 mg, 0.81 mmol) was added and stirred for 2 h at room temperature before the completion of the reaction. Post-treatment was carried out as follows. Suction filtration through Celite® was performed, washing was performed with acetone, and the mother liquor was concentrated. Pure Compound No. 27 (21.0 mg, 15.9%) was obtained as a yellow wax by high-performance liquid preparative chromatography. $^1$H-NMR (400 MHz, DMSO) δ 8.22 (d, J=8.5 Hz, 1H), 7.61 (d, J=8.6 Hz, 1H), 7.50 (d, J=8.6 Hz, 2H), 7.42 (s, 1H), 7.14 (d, J=8.6 Hz, 2H), 6.31 (dq, J=13.0, 6.4 Hz, 1H), 2.97 (s, 3H), 2.96 (s, 3H), 2.22-1.90 (m, 8H). LCMS: Calculated 514.1, found 515.1 ([M+H]$^+$).

Compound No. 28

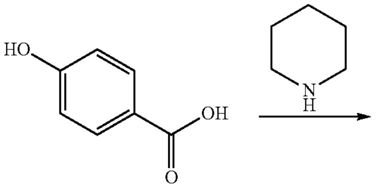

28-A1

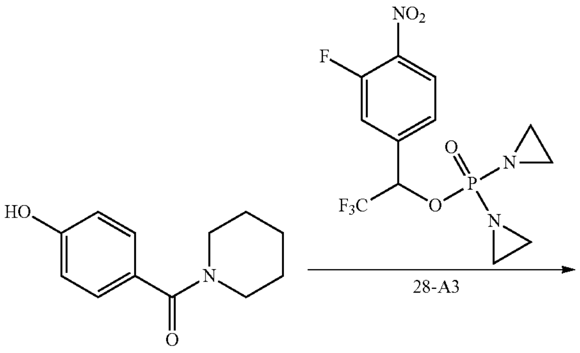

28-A3

28-A2

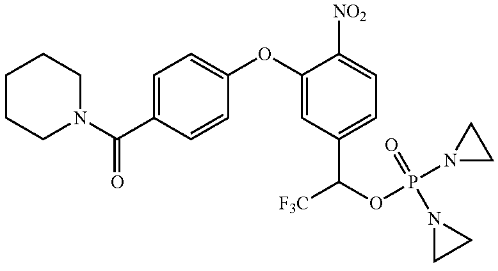

28

Under the protection of nitrogen, p-hydroxybenzoic acid (28-A1, 2.0 g, 14.48 mmol, commercially available) was added to DCM (40 ml) and then oxalyl chloride (5.5 g, 43.44 mmol) and DMF (53 mg, 0.72 mmol) were added and stirred at room temperature. After monitored for 2.5 h, the raw materials disappeared. Oxalyl chloride was removed by concentration. After the system was dissolved in DCM (50 ml), under the protection of nitrogen, piperidine (3.7 g, 43.44 mmol) and TEA (5.9 g, 57.92 mmol) were added dropwise to the system. Monitoring was performed for 30 min before the completion of the reaction. Post-treatment was performed as follows. After the reaction mixture was concentrated, it was dissolved in 1N NaOH solution (50 ml) and then stirred for 5 min. Extraction was performed with DCM (50 ml×3). The aqueous phase was made acidic with 6N HCl to precipitate white solid. After the solid was filtered with suction and dried, the product 28-A2 (2.0 g, yield=67.3%) was obtained as a white solid. $^1$H-NMR (400 MHz, MeOD): δ ppm 7.26 (dd, di, J=6.8, 2.0 Hz, 2H), 6.82 (dd, J=6.4, 2.0 Hz, 2H), 3.64-3.48 (m, 4H), 1.72-1.60 (m, 6H). LCMS: Calculated 205.1, found 206.1 ([M+H]$^+$).

Under the protection of nitrogen, 28-A3 (i.e., Compound No. 46, 150 mg, 0.41 mmol) and 28-A2 (167 mg, 0.81 mmol) were dissolved in acetone (10 ml), and then $Cs_2CO_3$ (463 mg, 1.42 mmol) was added to the system and stirred for 2 h at room temperature before the completion of the reaction. Post-treatment was carried out as follows. Suction filtration through Celite® was performed, washing was performed with acetone, and the mother liquor was concentrated. Pure Compound No. 28 (57 mg, 25.3%) was obtained as a yellow solid by high-performance liquid preparative chromatography. $^1$H-NMR (400 MHz, DMSO) δ 8.22 (d, J=8.5 Hz, 1H), 7.61 (d, J=8.5 Hz, 1H), 7.47-7.43 (m, 3H), 7.13 (t, J=5.6 Hz, 2H), 6.30 (dt, J=12.9, 6.5 Hz, 1H), 3.84-3.34 (m, 4H), 2.25-1.86 (m, 8H), 1.70-1.38 (m, 6H). LCMS: Calculated 554.2, found 555.1 ([M+H]$^+$).

Synthesis of Compound No. 29

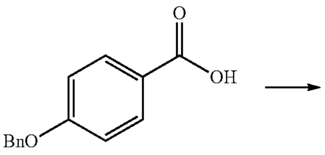

29-A1

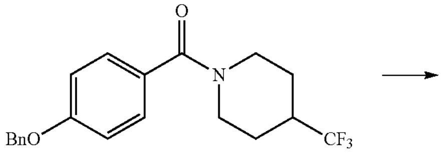

29-A2

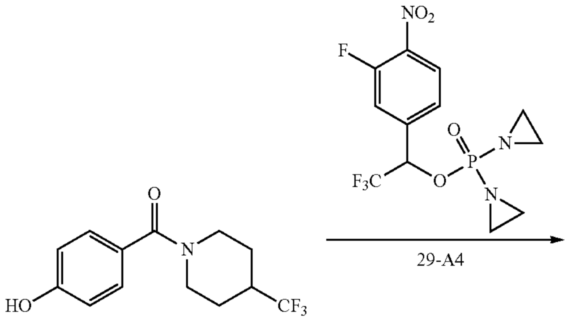

29-A4

29-A3

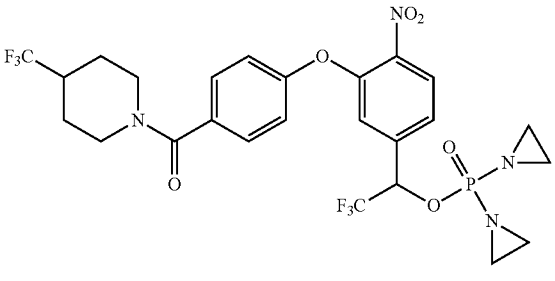

29

Under the protection of nitrogen, 29-A1 (500 mg, 2.19 mmol) and 4-(trifluoromethyl)piperidine (1.0 g, 6.57 mmol, commercially available) were added to DCM (10 ml), and then $T_3P$ (5.6 g, 4.38 mmol, 50% in EtOAc, commercially available) was added dropwise to the system. After the system was cooled to 5° C., DIEA (1.2 g, 8.77 mmol) was added dropwise to the system. After completion, the temperature was naturally raised to room temperature. The reaction was performed overnight before it was complete. Post-treatment was carried out as follows. The system was concentrated, dissolved in EtOAc (20 ml) and washed with $H_2O$ (20 ml×5). The organic phase was dried and concentrated to obtain 29-A2 (790 mg, yield=98.9%) as a white solid. $^1$H-NMR (400 MHz, MeOD): δ ppm 7.44-7.31 (m, 7H), 7.09-7.06 (m, 2H), 5.14. (s, 2H), 4.66 (m, 1H), 3.97 (m, 1H), 3.04 (m, 2H), 2.55-2.47 (m, 1H), 1.92 (m, 2H), 1.54-1.51 (m, 2H). LCMS: Calculated 363.1, found 364.2 ($[M+H]^+$).

Under the protection of nitrogen, 29-A2 (790 mg, 2.20 mmol) and PdOH (100 mg) were added to EtOH (10 ml). Evacuation and filling with nitrogen were performed three times. After evacuation and filling with hydrogen were performed three times, the temperature was increased to 35° C. overnight The next day, monitoring was performed until the completion of the reaction. Suction filtration through Celite® was performed, washing was performed with DCM, and the mother liquor was concentrated to obtain 29-A3 (450 mg, yield=75.2%) as a white solid. $^1$H-NMR (400 MHz, MeOD): δ ppm 7.29 (d, J=8.4 Hz, 2H), 6.84 (d, J=8.4 Hz, 2H), 4.59 (s, 1H), 4.06 (s, 1H), 3.00 (m, 2H), 2.55-2.47 (m, 1H), 1.92 (sm2H), 1.54-1.50 (m, 2H). LCMS: Calculated 273.1, found 274.0 ($[M+H]^+$).

Under the protection of nitrogen, 29-A4 (i.e., Compound No. 46, 100 mg, 0.27 mmol) and 29-A3 (118 mg, 0.54 mmol) were dissolved in acetone (10 ml), and then $Cs_2CO_3$ (265 mg, 0.81 mmol) was added and stirred for 3 h at room temperature before the completion of the reaction. Post-treatment was carried out as follows. Suction filtration through Celite® was performed, washing was performed with acetone, and the mother liquor was concentrated. Pure Compound No. 29 (55.0 mg, 32.6%) was obtained as a light yellow solid by high-performance liquid preparative chromatography. $^1$H-NMR (400 MHz, DMSO) δ 8.22 (d, J=8.5 Hz, 1H), 7.62 (d, J=8.5 Hz, 1H), 7.51 (d, J=8.6 Hz, 2H), 7.44 (s, 1H), 7.14 (d, J=8.6 Hz, 2H), 6.31 (dq, J=12.8, 6.2 Hz, 1H), 4.54 (s, 1H), 3.71 (s, 1H), 2.86 (s, 2H), 2.67-2.63 (m, 1H), 2.20-1.93 (m, 8H), 1.84 (m, 2H), 1.43 (qd, J=12.6, 4.2 Hz, 2H). LCMS: Calculated 622.1, found 623.2 ($[M+H]^+$).

Synthesis of Compound No. 30

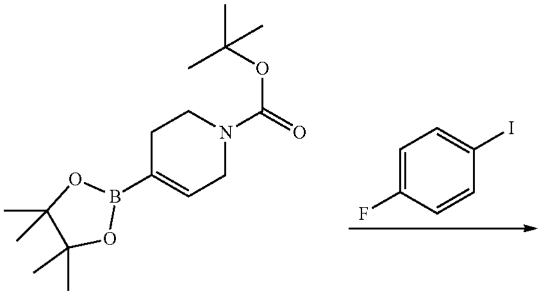

30-A1

-continued

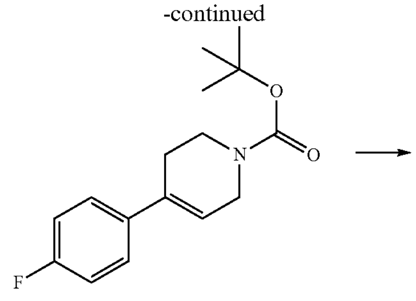

30-A2

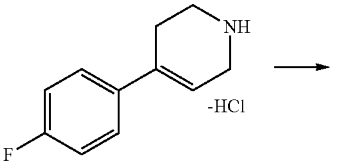

30-A3

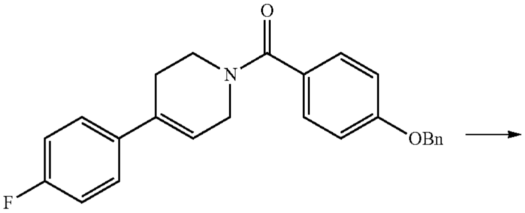

30-A4

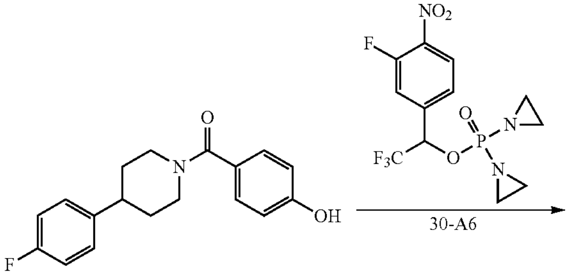

30-A5

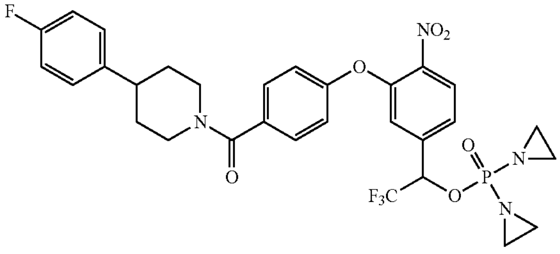

30

Under the protection of nitrogen, 30-A1 (1.5 g, 4.95 mmol, commercially available) and p-fluoroiodobenzene (1.0 g, 4.50 mmol, commercially available) were added to DMF (90 ml). After evacuation and filling with nitrogen were performed three times, dppf $PdCl_2$, i.e., 1,1'-bis(diphenylphosphino)ferrocene]dichloropalladium(330 mg, 0.45 mmol, commercially available), and $K_2CO_3$ (1.9 g, 13.51 mmol) were added to the system. After completion, evacuation and filling with nitrogen were performed 3 times again. The temperature of the system was increased to 110° C. overnight The next day, monitoring was performed until the completion of the reaction. After the system was cooled to room temperature, it was poured in water (100 ml), and extracted with EtOAc (100 ml×3). The organic phase was washed with water and washed with brine, and dried, concentrated and was subjected to column separation (200-300 mesh silica gel, n-heptane:EA=15:1 to 10:1) to obtain the product 30-A2 (920 mg, yield=73.6%) as a light green liquid. $^1$H-NMR (400 MHz, $CDCl_3$): δ ppm 7.34-7.31 (m, 2H), 7.03-6.99 (t, J=8.8 Hz, 2H), 5.97 (m, 1H), 4.06 (d, J=2.4 Hz, 2H), 3.64-3.61 (m, 2H), 2.49 (m, 2H), 1.49 (s, 9H). LCMS: Calculated 277.1, found 222.1 ($[M-56+H]^+$). 30-A2 (800 g, 2.88 mmol) was dissolved in MTBE (methyl tert-butyl ether, 2 ml), and then dioxane hydrochloride solution (4 M, 2 ml, 7.21 mmol) was added dropwise to the system. The temperature was kept at room temperature overnight The next day, monitoring was performed until the completion of the reaction. Suction filtration was performed, and the solid was washed with MTBE to obtain the product 30-A3 (460 mg, 74.70%) as an off-white solid. $^1$H-NMR (400 MHz, DMSO): δ ppm 9.18 (s, 2H), 7.52 (d, J=8.8, 5.6 Hz, 2H), 7.23-7.19 (m, 2H), 6.16 (s, 1H), 3.72 (s, 2H), 3.29 (m, 2H), 2.66 (m, 2H). LCMS: Calculated 213.1, found 178.1 ($[M-HCl+H]^+$).

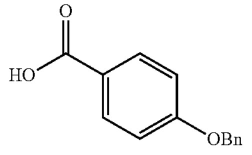 [SMILES: O=C(O)c1ccc(OCc2ccccc2)cc1]

Under the protection of nitrogen, (350 mg, 1.53 mmol) and 30-A3 (407 mg, 2.30 mmol) were added to DCM (10 ml), and then $T_3P$ (3.90 g, 6.12 mmol, 50% in EtOAc) was added dropwise to the system. After the system was cooled to 5° C., DIEA (791 mg, 6.12 mmol) was added dropwise to the system. After completion, the temperature was naturally raised to room temperature. Monitoring was performed 2 h before the completion of the reaction. The system was concentrated, dissolved in EtOAc (10 ml) and washed with $H_2O$ (10 ml×5). The organic phase was dried, concentrated and subjected to column separation (200-300 mesh silica gel, n-heptane:EA=1:1-0:1) to obtain the product 30-A4 (460 mg, yield=77.9%) as a light green oil. $^1$H-NMR (400 MHz, MeOD): δ ppm 7.45-7.43 (m, 6H), 7.39-7.36 (m, 2H), 7.32 (d, J=7.2 Hz, 1H), 7.10-7.03 (m, 4H), 6.13-5.97 (m, 1H), 5.15 (s, 2H), 4.29-4.22 (m, 2H), 3.93-3.69 (m, 2H), 2.60 (m, 2H).

Under the protection of nitrogen, 30-A4 (450 mg, 1.16 mmol) and $Pd(OH)_2$ (81 mg, commercially available) were added to EtOH (10 ml). Evacuation and filling with nitrogen were performed three times. After evacuation and filling with hydrogen were performed three times, the temperature was increased to 35° C. overnight. The next day, monitoring was performed until the completion of the reaction. Suction filtration through Celite®, and washing with DCM were performed. The mother liquor was concentrated to obtain the product 30-A5 (310 mg, yield=89.2%) as a colorless oil. $^1$H-NMR (400 MHz, MeOD): δ ppm 7.33-7.31 (m, 2H), 7.29-7.25 (m, 2H), 7.04-6.99 (m, 2H), 6.87-6.84 (m, 2H), 4.72 (m, 2H), 4.00 (m, 1H), 3.19-2.96 (m, 2H), 1.86 (m, 2H), 1.68-1.66 (m, 2H). LCMS: Calculated 299.1, found 300.1 ($[M+H]^+$).

Under the protection of nitrogen, 30-A6 (i.e., Compound No. 46, 100 mg, 0.27 mmol) was dissolved in acetone (10 ml), and then 30-A5 (97 mg, 0.33 mmol), and $Cs_2CO_3$ (265 mg, 0.81 mmol) were stirred for 3 h at room temperature. After the completion of the reaction, suction filtration through Celite® was performed, the solid was washed with acetone, and the mother liquor was concentrated. Pure Compound No. 30 (29.0 mg, 16.5%) was obtained as a light yellow solid by high-performance liquid preparative chromatography. $^1$H-NMR (400 MHz, DMSO-$d_6$): δ ppm 8.22 (d, J=8.5 Hz, 1H), 7.61 (d, J=8.5 Hz, 1H), 7.53 (d, J=8.6 Hz, 2H), 7.44 (s, 1H), 7.34-7.31 (m, 2H), 7.16-7.11 (m, 4H), 6.38-6.26 (m, 1H), 4.62 (m, 1H), 3.72 (m, 1H), 3.24-3.10 (m, 2H), 2.83 (m, 1H), 2.17-1.91 (m, 8H), 1.86-1.59 (m, 4H). LCMS: Calculated 648.2, found 649.2 ($[M+H]^+$).

Synthesis of Compound No. 33

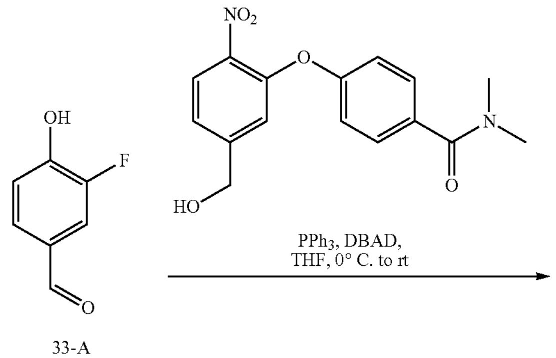

33-A

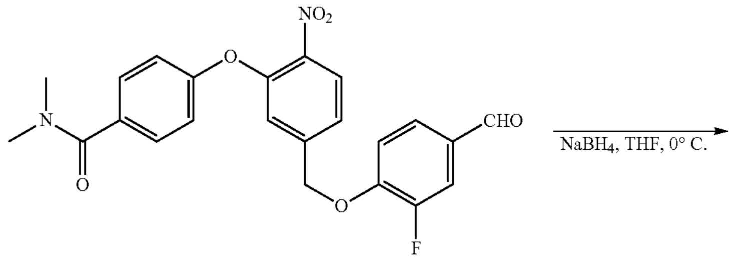

33-B

-continued

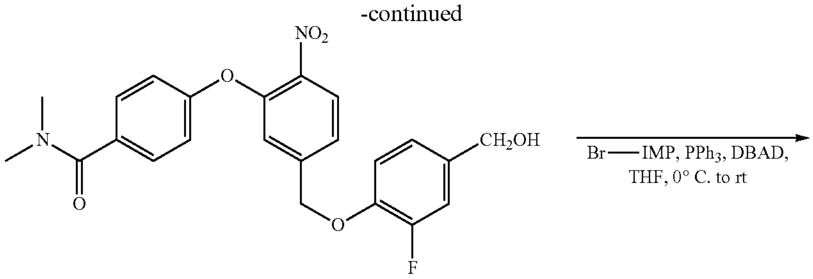

33-C

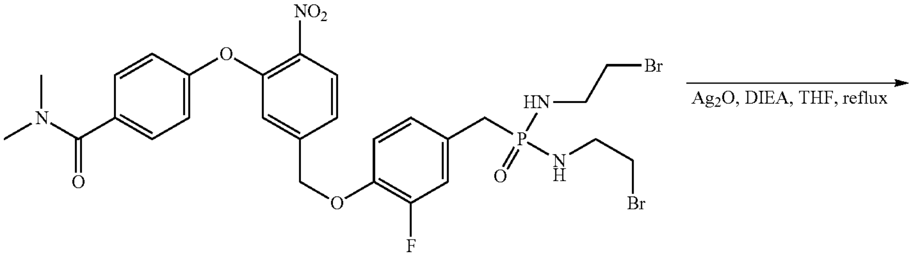

33-D

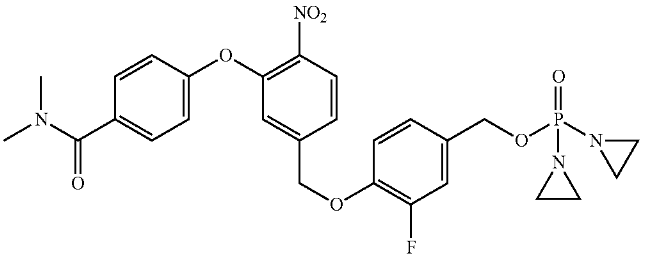

33

Under the protection of nitrogen,

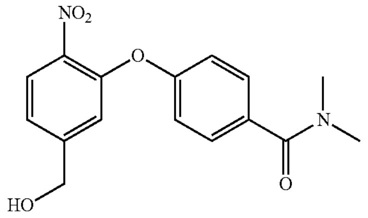 [SMILES: CN(C)C(=O)c1ccc(Oc2cc(CO)ccc2[N+](=O)[O-])cc1]

(1 g, 3.16 mmol) and 33-A (886 mg, 6.33 mmol, 1.2 eq., commercially available) were dissolved in THF (15 mL). Triphenylphosphine (1.66 g, 6.33 mml, 2 eq., commercially available) was added. The temperature was reduced to 0° C. A THF solution (8 mL) of di-tert-butyl azodicarboxylate (1.46 g, 6.33 mmol, 2 eq., commercially available) was added dropwise. The reaction was carried out at room temperature and was complete in 4 h. 10 ml of water was added. Extraction was performed with DCM (25 ml×3) followed by drying, and concentration. The sample was mixed and passed through a column (200-300 mesh silica gel, EA:n-heptane=2:1) to obtain the product 33-B (680 mg, yield=49.3%) as a light yellow solid. $^1$H-NMR (300M, $CDCl_3$): δ ppm 9.87 (s, 1H), 8.04 (d, J=7.8 Hz, 1H), 7.63 (d, J=9.6 Hz, 2H), 7.47 (d, J=8.1 Hz, 2H), 7.34 (d, J=7.5 Hz, 1H), 7.02-7.11 (m, 4H), 5.19 (s, 2H), 3.08 (brs, 6H). LCMS: Calculated 438.4, found 439.0 ([M+H]$^+$).

33-B (680 mg, 1.55 mmol) was dissolved in THF (10 ml), the temperature was reduced to 0° C., sodium borohydride (117 mg, 3.10 mmol, 2 eq.) was added in batches, and the temperature was kept at 0° C. and the reaction was complete in 1 h. Saturated ammonium chloride aqueous solution (5 ml) was added dropwise. Extraction was performed with DCM (10 ml×3) followed by drying, concentration, and column chromatography separation (100-200 mesh silica gel, EA) to obtain the product 33-C (410 mg, 60.3%) as a light yellow solid. $^1$H-NMR (300M, $CDCl_3$): δ ppm 8.02 (d, J=8.1 Hz, 1H), 7.43 (d, J=7.8 Hz, 2H), 7.31 (d, J=6.0 Hz, 1H), 7.12 (d, J=12.3 Hz, 1H), 6.99-7.03 (m, 4H), 6.84 (t, J=8.4 Hz, 1H), 5.16 (s, 2H), 4.62 (s, 2H), 3.08 (brs, 6H). LCMS: Calculated 440.4, found 441.0 ([M+H]$^+$).

Under the protection of nitrogen, 33-C (400 mg, 0.91 mmol) was dissolved in THF (5 ml). Triphenylphosphine (480 mg, 1.82 mmol) and Br-IPM (564 mg, 1.82 mmol, commercially available) were added. The temperature was reduced to 0° C. A THF solution (5 mL) of di-tert-butyl azodicarboxylate (420 mg, 1.82 mmol) was added dropwise at 0° C. The reaction was carried out at room temperature for 3 h. At 0° C., water (5 mL) was added. Extraction was performed with DCM (10 ml×3) followed by drying, concentration, and column chromatography separation (200-300 mesh silica gel, DCM:methanol=50:1) to obtain 33-D (300 mg, yield=45.0%) as a light yellow solid. $^1$H-NMR (400M, $CDCl_3$): δ ppm 8.01 (d, J=8.4 Hz, 1H), 7.45 (d, J=8.8 Hz, 2H), 7.32 (d, J=8.0 Hz, 1H), 7.26 (m, 1H), 7.16 (dd, J=11.5, 1.6 Hz, 1H), 7.10 (s, 1H), 7.02 (d, J=8.4 Hz, 2H), 6.89 (t, J=8.4 Hz, 1H), 5.13 (s, 2H), 4.95 (d, J=8.4 Hz, 2H), 3.45-3.41 (m, 4H), 3.34-3.30 (m, 4H), 3.08 (s, 6H). LCMS: Calculated 732.0, found 732.8 ([M+H]$^+$).

Under the protection of nitrogen, 33-D (200 mg, 0.27 mmol) was dissolved in THF (5 ml). Silver oxide (742 mg, 3.2 mmol, 11.8 eq.) was added, and diisopropylethylamine (176 mg, 1.365 mmol, 5 eq.) was added dropwise. The temperature was increased to reflux temperature. The reaction was performed for 2 h before the temperature was reduced to room temperature. Suction filtration through Celite® was performed, followed by washing with THF several times, and performing concentration at low temperature to prepare and obtain Compound No. 33 (5 mg, 3.2%) as a white solid. $^1$H-NMR (400M, $CDCl_3$): δ ppm 7.99 (d, J=8.4 Hz, 1H), 7.44 (d, J=8.8 Hz, 2H), 7.31 (d, J=8.0 Hz, 1H), 7.15 (dd, J=11.6, 2.0 Hz, 1H), 7.11 (s, 1H), 7.03-7.07 (m, 3H), 6.91 (t, J=8.4 Hz, 1H), 5.09 (s, 2H), 5.05 (d, J=8.0 Hz, 2H), 3.09 (s, 3H), 3.00 (s, 3H), 2.18-2.08 (m, 8H). (retention time: 7.359 min). LCMS: Calculated 570.0, found 571.0 ([M+H]$^+$).

Synthesis of Compound No. 34

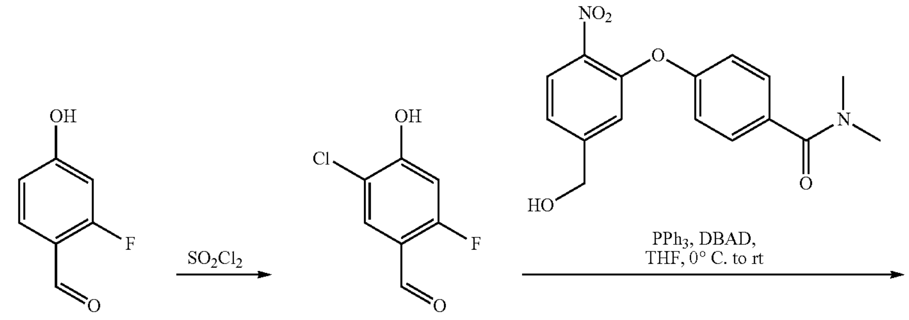

34-A 34-B

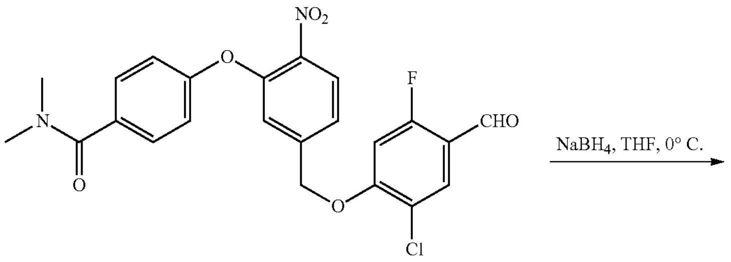

34-C

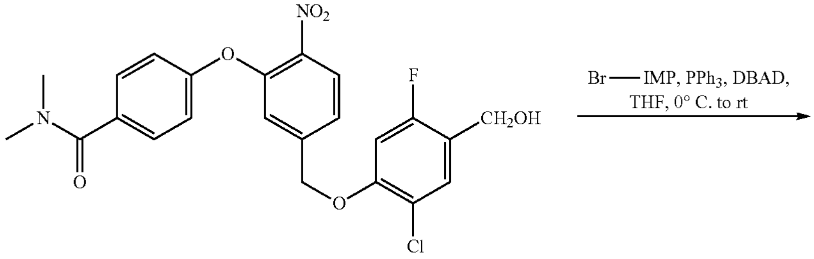

34-D

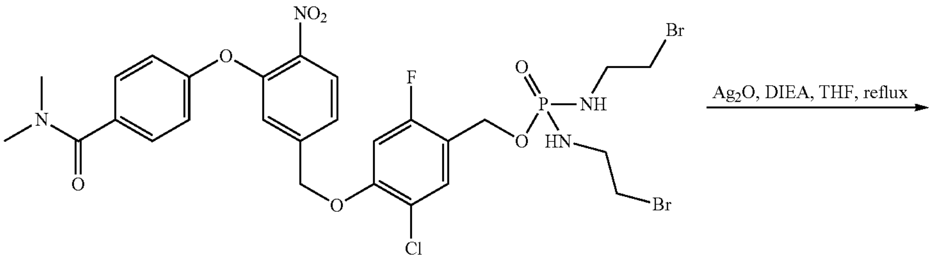

34-E

-continued

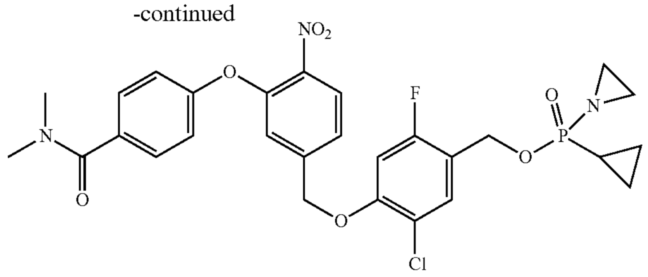

34

34-A (10.0 g, 71.4 mmol commercially available) was added to acetic acid (30 ml), and then sulfonyl chloride (14.4 g, 107 mmol, 1.5 eq.) was added, and reacted at room temperature for 17 h. 300 ml of ice water was added. Extraction was performed with EA (300 ml×2). The organic phase was washed with brine (20 ml×2) and dried with anhydrous $Na_2SO_4$, and the solvent was spin-dried to obtain a crude product. The crude product was slurried with methyl tert-butyl ether and filtered with suction to obtain 34-B (3.0 g, 25%) as a white solid. $^1$H-NMR (400M, DMSO-$d_6$): δ ppm 9.98 (s, 1H), 7.80 (d, J=8.4 Hz, 1H), 6.89 (d, H211.6 Hz, 1H). LCMS: Calculated 174.0, found 175.0 ([M+H]$^+$).

Under the protection of nitrogen, 34-C (375 mg, 2.15 mmol, 2 eq.) was added to THF (10 ml).

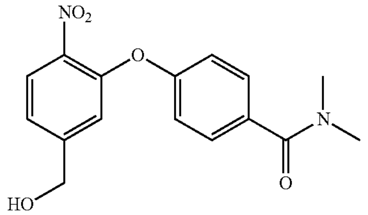 [SMILES: CN(C)C(=O)c1ccc(Oc2cc(CO)ccc2[N+](=O)[O-])cc1]

(340 mg, 1.08 mmol) and triphenylphosphine (563 mg, 2.15 mmol, 2 eq., commercially available) were added. DBAD (494.5 mg, 2.15 mmol, 2 eq., commercially available) was added at 0° C. The reaction was performed for 1 h at room temperature. DCM (50 ml) was added for dilution. The organic phase was washed with water (10 ml×2) and with saturated brine (10 ml), dried and spin-dried. The sample was mixed and passed through a FLASH column (300-400 mesh silica gel, EA and n-heptane, 33% to 100%) to obtain 34-C (400 mg, 78.7%) as a white product $^1$H-NMR (400M, DMSO-$d_6$): δ ppm 10.04 (s, 1H), 8.18 (d, J=8.4 Hz, 1H), 7.87 (d, J=7.2 Hz, 1H), 7.49 (d, J=8.4 Hz, 2H), 7.44 (d, J=8.4 Hz, 1H), 7.36 (d, J=8.4 Hz, 1H), 7.31 (s, 1H), 7.15 (d, J=8.4 Hz, 2H), 5.44 (s, 2H), 2.97 (s, 6H). LCMS: Calculated 472.1, found 472.9 ([M+H]$^+$).

Under the protection of nitrogen, 34-C (200 mg, 0.42 mmol) was added to THF (10 ml), sodium borohydride (32 mg, 0.84 mmol, 2 eq., commercially available) was added at 0° C., the temperature was naturally increased and the reaction was performed for 0.5 h. After the completion of the reaction, saturated ammonium chloride aqueous solution (10 ml) was added dropwise. Extraction was performed with DCM (20 ml×3) followed by washing with water (10 ml), washing with saturated brine (10 ml), drying and spin-drying, slurrying with isopropanol and filtering with suction to obtain 34-D (100 mg, 50%) as a white solid. $^1$H-NMR (400M, DMSO-$d_6$): δ ppm 8.16 (d, J=8.4 Hz, 1H), 7.49 (d, J=8.4 Hz, 2H), 7.46 (d, J=8.0 Hz, 1H), 7.43 (d, J=9.6 Hz, 1H), 7.30 (s, 1H), 7.15-7.12 (m, 3H), 5.32 (s, 2H), 5.27 (t, J=5.6 Hz, 1H), 4.45 (d, J=5.6 Hz, 2H), 2.97 (s, 6H). LCMS: Calculated 474.1, found 475.0 ([M+H]$^+$).

Under the protection of nitrogen, 34-D (100 mg, 0.21 mmol) was added to THF (10 ml). Triphenylphosphine (110 mg, 0.42 mmol, 2 eq.) and Br-IPM (129 mg, 0.42 mmol, 2 eq.) were added. Di-tert-butyl azodicarboxylate (97 mg, 0.42 mmol, 2 eq.) was added at 0° C. The reaction was performed at room temperature for 4 h. After completion, DCM (50 ml) was added. The organic phase was washed with saturated brine (10 ml), dried and spin-dried, and passed through a flash column (300-400 mesh silica gel, EA and n-heptane, 0-100%, and then DCM:MeOH (20:1)) to obtain 34-E (70 mg, 43.7%) as a yellow oil. $^1$H-NMR (400M, $CDCl_3$): δ ppm 7.96 (d, J=8.4 Hz, 1H), 7.40-7.38 (m, 3H), 7.25 (d, J=7.6 Hz, 1H), 7.07 (s, 1H), 6.99 (d, J=8.8 Hz, 2H), 6.57 (d, J=10.8 Hz, 1H), 5.04 (s, 2H), 4.92 (d, J=8.0 Hz, 2H), 3.36-3.39 (m, 4H), 3.24-3.29 (m, 4H), 3.01 (s, 6H). LCMS: Calculated 766.0, found 766.8 ([M+H]$^+$).

34-E (70 mg, 0.091 mmol) was added to THF (5 ml), and silver oxide (250 mg, 1.08 mmol, 11.8 eq.) and DIEA (55 mg, 0.428 mmol, 4.7 eq.) were added, heated to 65° C., and reacted for 6 h. After the completion of the reaction, suction filtration was performed, the filter cake was washed with THF (10 ml×2), the filtrate was filtered with suction again with a filter membrane, and the filtrate was spin-dried to obtain a crude product. 34 (5 mg, 9.1%) was obtained as a white solid by preparative HPLC. $^1$H-NMR (400M, $CD_3OD$): δ ppm 8.08 (d, J=8.4 Hz, 1H), 7.54-7.47 (m, 4H), 7.37 (s, 1H), 7.12 (d, J=8.8 Hz, 2H), 7.06 (d, J=11.2 Hz, 1H), 5.29 (s, 2H), 5.14 (d, J=8.0 Hz, 1H), 3.13 (s, 3H), 3.07 (s, 3H), 2.15-2.14 (m, 8H). LCMS: Calculated 604.0, found 605.0 ([M+H]$^+$).

For the synthesis of Compound No. 35-44/47-49, please refer to the above methods.

The properties, and NMR, and mass spectrum data were provided as follows.

Compound No. 35

A solid, $^1$H-NMR (400 MHz, $CDCl_3$) δ 7.99 (d, J=8.4 Hz, 1H), 7.47 (d, J=8.6 Hz, 2H), 7.32 (d, J=8.3 Hz, 1H), 7.17 (s, 1H), 7.05 (d, J=8.6 Hz, 2H), 6.95 (t, J=6.9 Hz, 2H), 5.54-5.48 (m, 1H), 5.14 (s, 2H), 3.11 (s, 3H), 3.03 (s, 3H), 2.21-2.00 (m, 8H), 1.57 (d, J=6.5 Hz, 3H). LCMS: Calculated 602.2, found 603.2 ([M+H]+).

Compound No. 36

A solid, $^1$H-NMR (400 MHz, $CDCl_3$) δ 8.01 (d, J=8.4 Hz, 1H), 7.71-7.62 (m, 2H), 7.34 (d, J=8.4 Hz, 1H), 7.22 (s, 1H), 7.04 (d, J=8.8 Hz, 2H), 6.95 (d, J=8.5 Hz, 2H), 5.47-5.28 (m, 1H), 5.17 (s, 2H), 5.06 (d, J=8.1 Hz, 2H), 4.62-4.48 (m, 2H), 4.38 (m, 2H), 2.32-2.04 (m, 8H). LCMS: Calculated 518.1, found 619.2 ([M+H]+).

Compound No. 37

A wax, $^1$H-NMR (400 MHz, $CDCl_3$) δ 8.05 (d, J=8.4 Hz, 1H), 7.71-7.63 (m, 2H), 7.46-7.38 (m, 1H), 7.31 (s, 1H), 7.09-7.01 (m, 2H), 6.97 (d, J=8.6 Hz, 2H), 5.20 (s, 2H), 5.07 (d, J=8.0 Hz, 2H), 2.31-2.06 (m, 8H). LCMS: Calculated 542.1, found 543.1 ([M+H]+).

Compound No. 38

An off-white solid, $^1$H-NMR (400 MHz, $CDCl_3$) δ 8.02 (d, J=8.4 Hz, 1H), 7.68 (d, J=8.7 Hz, 2H), 7.36 (d, J=8.5 Hz, 1H), 7.24 (s, 1H), 7.05 (d, J=8.7 Hz, 2H), 6.96 (d, J=8.5 Hz, 2H), 5.18 (s, 2H), 5.06 (d, J=8.1 Hz, 2H), 4.59-4.53 (m, 4H), 2.38-2.02 (m, 8H). LCMS: Calculated 536.1, found 637.1 ([M+H]+).

Compound No. 39

A wax, $^1$H-NMR (400 MHz, $CDCl_3$) δ 8.03 (d, J=8.4 Hz, 1H), 7.55-7.44 (m, 2H), 7.37 (d, J=8.4 Hz, 1H), 7.30-7.26 (m, 1H), 7.25-7.20 (m, 2H), 7.02-6.90 (m, 2H), 5.20 (s, 2H), 5.06 (d, J=8.0 Hz, 2H), 2.28-2.10 (m, 8H). LCMS: Calculated 542.1, found 543.1 ([M+H]+).

Compound No. 40

An off-white solid, $^1$H-NMR (400 MHz, DMSO-$d_6$): δ ppm 8.90-8.89 (s, 1H), 8.33 (d, J=1.2 Hz, 1H), 8.31 (d, J=1.2 Hz, 1H), 8.25 (d, J=8.4 Hz, 1H), 8.13 (d, J=10.0 Hz), 7.63-7.55 (m, 4H), 7.46 (d, J=1.2 Hz, 1H), 6.30-6.26 (m, 1H), 2.11-1.92 (m, 8H). LCMS: Calculated 494.1, found 495.1 ([M+H]+).

Compound No. 41

An off-white solid, $^1$H-NMR (400 MHz, MeOD): δ ppm 8.43 (d, J=2.9 Hz, 1H), 7.24-7.19 (m, 2H), 6.13-6.03 (m, 1H), 2.26-2.08 (m, 8H). LCMS: Calculated 576.1, found 577.2 ([M+H]+).

Compound No. 42

An off-white solid, $^1$H-NMR (400 MHz, DMSO-$d_6$): δ ppm 8.20 (d, J=8.2 Hz, 1H), 7.99-7.90 (m, 1H), 7.89 (s, 1H) 7.55 (d, J=8.4 Hz, 1H), 7.31-7.26 (m, 1H), 6.28-6.24 (m, 1H), 2.80 (s, 3H), 2.10-1.91 (m, 8H). LCMS: Calculated 514.1, found 515.0 ([M+H]+).

Compound No. 43

An off-white solid, $^1$H-NMR (400 MHz, MeOD): δ ppm 8.05 (d, J=8.0 Hz, 1H), 8.01 (s, 1H) 7.68 (d, J=8.0 Hz, 1H), 7.49 (d, J=2.0 Hz, 1H), 7.43 (d, J=8.0 Hz, 1 H), 7.27 (dd, J=8.8, 2.0 Hz, 1H), 7.17 (s, 1H), 5.99-5.94 (m, 1H), 2.20-2.02 (m, 8H). LCMS: Calculated 497.1, found 498.1 ([M+H]+).

Compound No. 44

An off-white solid, $^1$H-NMR (400 MHz, MeOD) δ8.07 (d, J=8.4 Hz, 1H), 7.75-7.67 (m, 2H), 7.65-7.59 (m, 2H), 7.49 (d, J=8.5 Hz, 1H), 7.44 (t, J=7.6 Hz, 2H), 7.35 (d, J=7.3 Hz, 1H), 7.31 (s, 1H), 7.20-7.14 (m, 2H), 6.07-5.97 (m, 1H), 2.26-2.03 (m, 8H). LCMS: Calculated 519.1, found 520.1 ([M+H]$^+$).

Compound No. 47

An off-white solid, $^1$H-NMR (400 MHz, MeOD) δ8.03 (d, J=8.4 Hz, 1H), 7.43 (d, J=8.4 Hz, 1H), 7.34 (d, J=8.5 Hz, 2H), 7.19 (s, 1H), 7.03 (t, J=5.7 Hz, 2H), 6.07-5.94 (m, 1H), 3.09-2.99 (m, 1H), 2.24-2.02 (m, 10H), 1.87-1.83 (m, 2H), 1.77-1.68 (m, 2H), 1.65-1.56 (m, 2H). LCMS: Calculated 511.1, found 512.2 ([M+H]+).

Compound No. 48

An off-white solid, $^1$H-NMR (400 MHz, MeOD) δ8.03 (d, J=8.4 Hz, 1H), 7.43 (d, J=8.6 Hz, 1H), 7.31 (d, J=8.5 Hz, 2H), 7.19 (s, 1H), 7.02 (d, J=8.5 Hz, 2H), 6.00-5.96 (m, 1H), 2.56 (m, 1H), 2.23-2.03 (m, 8H), 1.87 (m, 4H), 1.78-1.75 (m, 2H), 1.49-1.43 (m, 5H). LCMS: Calculated 525.2, found 526.2 ([M+H]+).

Compound No. 49

A yellow wax, $^1$H-NMR (400 MHz, MeOD) δ8.04 (d, J=8.4 Hz, 1H), 7.45 (d, J=8.2 Hz, 1H), 7.35 (d, J=8.6 Hz, 2H), 7.21 (s, 1H), 7.04 (d, J=8.6 Hz, 2H), 5.99 (dd, J=9.9, 6.2 Hz, 1H), 2.74 (t, J=12.5 Hz, 1H), 2.23-2.04 (m, 10H), 2.02-1.73 (m, 6H). LCMS: Calculated 561.1, found 562.2 ([M+H]+).

Synthesis of Compound No. 46

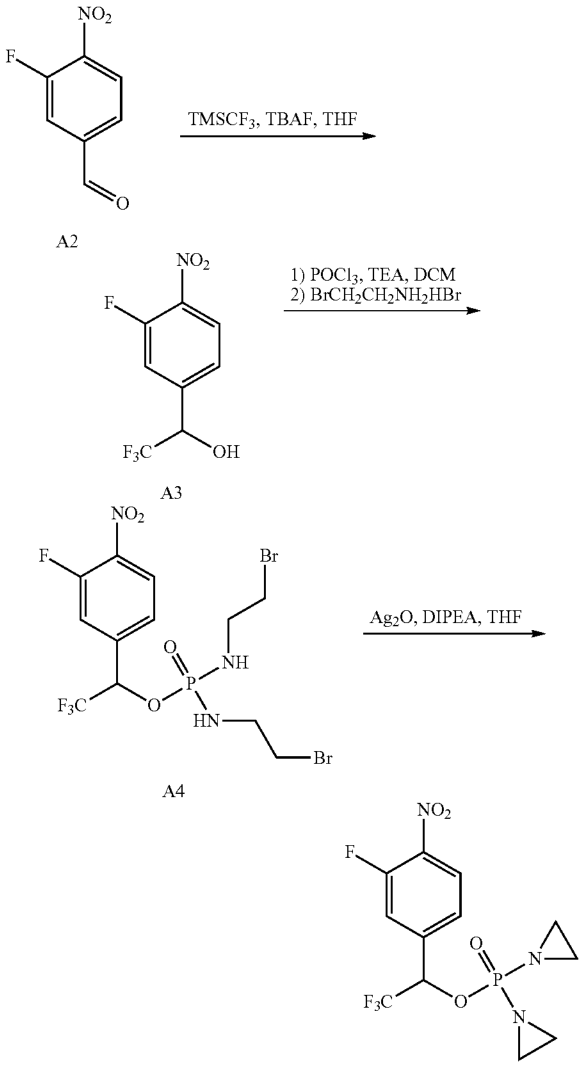

A2 A3 A4 46

Under the protection of nitrogen, A2 (2.0 g, 11.8 mmol, commercially available) and $TMSCF_3$ (2.5 g, 17.7 mmol, commercially available) were dissolved in THF (20 mL). The temperature was reduced to 0° C. TBAF (2.6 ml, 0.26 mmol, 1 mol/L THF solution, commercially available) was added dropwise to the system. The temperature was kept at 0° C. After 30 min, A2 disappeared completely. 3N HCl (2 ml) was added dropwise to the system, and the system became clear. After stirring at 0° C. for 1 h, all the raw materials were converted to products. Extraction was performed with DCM (10 ml×3). The organic phase was washed with water (10 ml×3), dried, concentrated and subjected to column separation (200-300 mesh silica gel, n-heptane:EA=12:1-10:1) to obtain the product A3 (1.5 g, yield=53.2%) as a yellow oil. $^1$H-NMR (400 MHz, $CDCl_3$): δ ppm 8.13-8.09 (m, 1H), 7.60 (d, J=11.6 Hz, 1H), 7.43 (d, J=8.4 Hz, 1H), 5.12-5.18 (m, 1H), 3.06 (d, J=4.4 Hz, 1H).

Under the protection of nitrogen, $POCl_3$ (963 mg, 4.61 mmol, commercially available) was dissolved in DCM (10 ml). After that, the temperature was reduced to −40° C. Then, A3 (1.5 g, 6.27 mmol) was dissolved in DCM (20 ml) before being added dropwise to the system with TEA (1.6 g, 15.70 mmol). After the temperature was kept at −40° C. for 2 h, 46-A3 was completely converted to an intermediate. Then, bromoethylamine hydrobromide (11.99 g, 50.16 mmol) and TEA (10.1 g, 0.1 mol) were added to the system. Monitoring was performed. The reaction was complete in 30 min. At 0° C., saturated $NH_4Cl$ (20 ml) was added. Extraction was performed with DCM (50 ml×3). The organic phase was washed with water and washed with brine, dried, concentrated, and subjected to column separation (200-300 mesh silica gel, n-heptane:EA=5:1-1:1) to obtain the product A4 (1.6 g, yield=65.3%) as a yellow oil. $^1$H-NMR (400 MHz, $CDCl_3$): δ ppm 8.15-8.11 (m, 1H), 7.47 (d, J=11.6 Hz, 1H), 7.44 (d, J=8.8 Hz, 1H), 5.78-5.30 (m, 1H), 3.53-3.05 (m, 10H). LCMS: Calculated 529.9, found 531.9 ($[M+H]^+$).

Under the protection of nitrogen, A4 (1.6 g, 3.0 mmol) was dissolved in THF (20 ml), and then silver oxide (4.2 g, 18.0 mmol), and DIPEA (2.3 g, 18.0 mmol) were added. The temperature was increased to 65° C. and stirring was performed for 1.5 h. After the reaction was complete, the temperature was reduced to room temperature. Suction filtration through Celite® was performed. The solid was washed with DCM, and the mother liquor was concentrated and subjected to column separation to obtain a crude product (520 mg, yield=46.8%)(200-300 mesh silica gel, n-heptane: EA=5:1-1:1). Pure Compound No. 46 (30 mg) was obtained as a white solid by high-performance liquid preparative chromatography. $^1$H-NMR (400 MHz, MeOD): δ ppm 8.24-8.20 (m, 1H), 7.70 (d, J=11.6 Hz, 1H), 7.63 (d, J=8.8 Hz, 1H), 6.14-6.10 (m, 1H), 2.28-2.14 (m, 8H). LCMS: Calculated 369.1, found 370.1 ($[M+H]^+$).

The experimental facts of the above specific compound examples verify that all the compounds provided by the present invention are either solids or waxes (semi-solids), which overcome the disadvantage that the previous DNA alkylating agents are oils (disclosed in PCT Application No. PCT/US2016/021581 (Publication No. WO2016145092), which corresponds to Chinese Patent Application No. 2016800150788 (Publication No. CN107530556A)), and facilitate preparation of formulations.

The invention claimed is:

1. A solid compound of formula II or III or a pharmaceutically acceptable salt, or a solvate thereof,

II

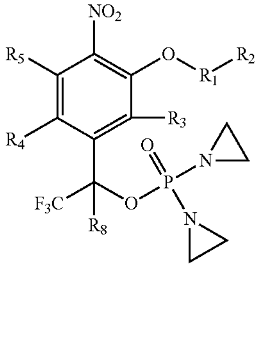

-continued

III

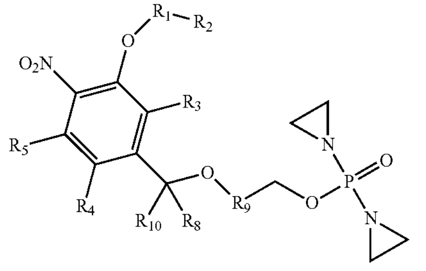

wherein $R_1$ is $C_6$-$C_{10}$ aryl or Z-substituted aryl, 4-15 membered heterocycle or Z-substituted heterocycle, 5-15 membered heteroaryl or Z-substituted heteroaryl, or a 7-15 membered fused ring or Z-substituted fused ring;

$R_2$ is hydrogen, a halogen atom, cyano or isocyano, hydroxy, sulfhydryl, amino, OTs, OLCMS, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ to aryl or Z-substituted aryl, 4-15 membered heterocycle or Z-substituted heterocycle, 5-15 membered heteroaryl or Z-substituted heteroaryl, ether having from 1 to 6 carbon atoms or Z-substituted alkoxy having from 1 to 6 carbon atoms, $—CONR^6R^7$, $—SO_2NR^6R^7$, $—SO_2R_6$, $—OCOO—R^6$, $—COOR^6$, $—NR^6COR^7$, $—OCOR^6$, $—NR^6SO_2R^7$ or $—NR^6SO_2NR^6R^7$, or $R^2$ together with the atom in the group $R_1$ to which it is bonded to form a 7-15 membered fused ring or Z-substituted fused ring;

$R_3$ is hydrogen;

$R_4$ and $R_5$ are each hydrogen;

$R^6$ and $R^7$ are each independently hydrogen, cyano or isocyano, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered heterocycle or Z-substituted heterocycle, 5-15 membered heteroaryl or Z-substituted heteroaryl, or $C_1$-$C_6$ alkoxy or Z-substituted $C_1$-$C_6$ alkoxy, or $R^6$ and $R^7$ together with the atom to which they are bonded to form 5-7 membered heterocyclyl or Z-substituted 5-7 membered heterocyclyl;

$R_8$ and $R_{10}$ are each hydrogen;

$R_9$ is substituted $C_6$-$C_{10}$ aryl which is substituted with at least one fluorine atom or nitro group, substituted 4-15 membered heterocycle which is substituted with at least one fluorine atom or nitro group, or substituted 5-15 membered heteroaryl which is substituted with at least one fluorine atom or nitro group;

the substituent Z is a halogen atom, cyano or isocyano, hydroxy, sulfhydryl, amino, OTs, OLCMS, $C_1$-$C_3$ alkyl or substituted alkyl, $C_1$-$C_3$ alkoxy or substituted alkoxy, $C_2$-$C_3$ alkenyl or substituted alkenyl, $C_2$-$C_3$ alkynyl or substituted alkynyl, $C_3$-$C_8$ cycloalkyl or substituted cycloalkyl, an aromatic ring, heterocycle, a heteroaromatic ring and fused ring or a substituted aromatic ring, heterocycle, or a heteroaromatic ring and fused ring, the pattern of substitution being mono- or geminal di-substitution;

the substitution in the substituted $C_6$-$C_{10}$ aryl, substituted 4-15 membered heterocycle or substituted 5-15 membered heteroaryl in $R_9$ is a halogen atom, nitro, cyano or isocyano, hydroxy, amino, $C_1$-$C_3$ alkyl or alkoxy, alkenyl, alkynyl, cycloalkyl or benzene ring, substituted benzene ring, $C_1$-$C_3$ alkoxy or halogen atom-substituted alkoxy.

2. The solid compound according to claim 1, wherein $R_1$ is phenyl or Z-substituted phenyl, six-membered nitrogen-containing heterocycle or Z-substituted heterocycle, six-membered nitrogen-containing heteroaryl or Z-substituted heteroaryl, or 9-14 membered fused ring or Z-substituted fused ring;

$R_2$ is hydrogen, a halogen atom, cyano or isocyano, hydroxy, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered nitrogen-containing heterocycle or Z-substituted nitrogen-containing heterocycle, 5-15 membered nitrogen-containing heteroaryl or substituted nitrogen-containing heteroaryl, $C_1$-$C_6$ alkoxy or fluorine-substituted $C_1$-$C_6$ alkoxy, —$CONR^6R^7$, —$SO_2NR^6R^7$, —$SO_2R^6$, —OCOO—$R^6$, —$COOR^6$, —$NR^6COR^7$, —$OCOR^6$, —$NR^6SO_2R^7$ or —$NR^6SO_2NR^6R^7$;

$R^6$ and $R^7$ are each independently $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered heterocycle or Z-substituted heterocycle, 5-15 membered heteroaryl or Z-substituted heteroaryl, $C_1$-$C_6$ alkoxy or fluorine-substituted $C_1$-$C_6$ alkoxy, or $R^6$ and $R^7$ together with the nitrogen atom to which they are bonded to form a 5-7 membered heterocyclic group or a Z-substituted 5-7 membered heterocyclic group.

3. The solid compound according to claim 1, wherein $R_1$ is phenyl or Z-substituted phenyl, six-membered nitrogen-containing heterocycle or Z-substituted heterocycle, six-membered nitrogen-containing heteroaryl or Z-substituted heteroaryl, or 9-14 membered fused ring or Z-substituted fused ring;

$R_2$ is hydrogen, a halogen atom, cyano or isocyano, hydroxy, $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered nitrogen-containing heterocycle or Z-substituted nitrogen-containing heterocycle, 5-15 membered nitrogen-containing heteroaryl or substituted nitrogen-containing heteroaryl, $C_1$-$C_6$ alkoxy or fluorine-substituted $C_1$-$C_6$ alkoxy, —$CONR^6R^7$, —$SO_2R_6$, —OCOO—$R^6$, —$COOR^6$, —$NR^6COR^6$, —$OCOR^6$, —$NR^6SO_2R_6$, or —$NR^6SO_2NR^6R^7$;

$R^6$ and $R^7$ are each independently $C_1$-$C_6$ alkyl or Z-substituted alkyl, $C_2$-$C_6$ alkenyl or Z-substituted alkenyl, $C_2$-$C_6$ alkynyl or Z-substituted alkynyl, $C_3$-$C_8$ cycloalkyl or Z-substituted cycloalkyl, $C_6$-$C_{10}$ aryl or Z-substituted aryl, 4-15 membered heterocycle or Z-substituted heterocycle, 5-15 membered heteroaryl or Z-substituted heteroaryl, $C_1$-$C_6$ alkoxy or fluorine-substituted $C_1$-$C_6$ alkoxy, or $R^6$ and $R^7$ together with the nitrogen atom to which they are bonded to form a 5-7 membered heterocyclic group or a Z-substituted 5-7 membered heterocyclic group.

4. The solid compound according to claim 1, wherein in formula II and formula III, $R_1$ is phenyl, tetrahydropyran, tetrahydrothiopyran, tetrahydrofuran, pyridine, furan, pyran, thiopyran, thiazole, dihydropyridine, morpholine, piperazine, pyridazine, pyrazine, 1,3,5-triazine, naphthalene, quinine, benzothiazole, benzothiopyran, benzofuran, benzimidazole, indole, imidazopyridine or Z-substituted phenyl, piperidine, tetrahydropyran, tetrahydrothiopyran, tetrahydrofuran, pyridine, furan, pyran, thiopyran, thiazole, dihydropyridine, morpholine, piperazine, pyridazine, pyrazine, 1,3,5-triazine, naphthalene, quinine, benzothiazole, benzothiopyran, benzofuran, benzimidazole, indole or imidazopyridine;

$R_2$ is —$CON(CH_3)_2$, —$SO_2CH_3$, —OCOO—$CH_3$, —$COOCH_3$, —$NHCOCH_3$, —$NMeCOCH_3$, —$NHCOCF_3$, —$OCOCH_3$, —$NHSO_2CH_3$, —$NMeSO_2CH_3$, —$NHSO_2CF_3$, —$NMeSO_2CF_3$, —$CF_3$, F, $C_1$, CN, Me, benzene, fluorobenzene, chlorobenzene, —$OCF_3$, $C_5$-$C_6$ cycloalkyl or F-substituted $C_5$-$C_6$ cycloalkyl, pyridyl, fluoropyridyl, chloropyridyl, furyl, thiopyran, thiazole, —CONMePh,

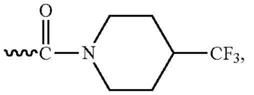,
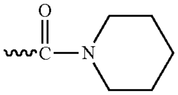,
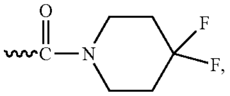,
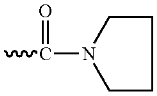,
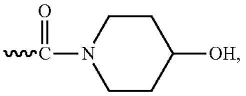,
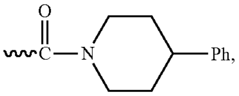,
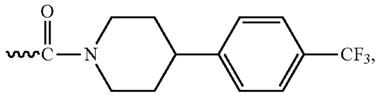,
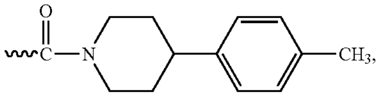,
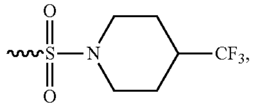,
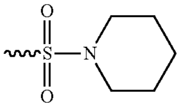,
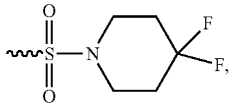,
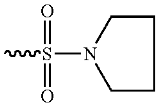,
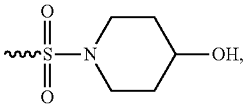,
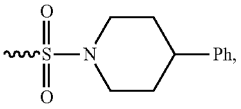,
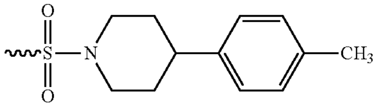
or
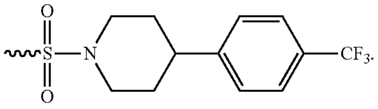.

5. The solid compound according to claim 1, wherein $R_9$ is monofluoro, monofluoro-monochloro, difluoro or tetrafluoro-substituted phenyl.

6. The solid compound according to claim 1, wherein $R_9$ is

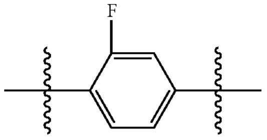
,
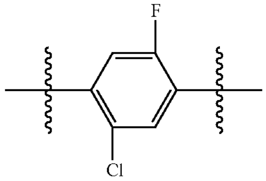
,
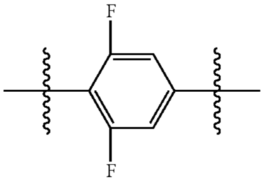
, or
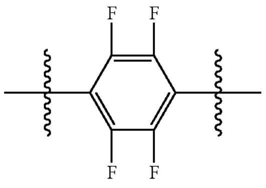
.
7. The solid compound according to claim 1, wherein the compound substituted with the isotope deuterium has the following structure:
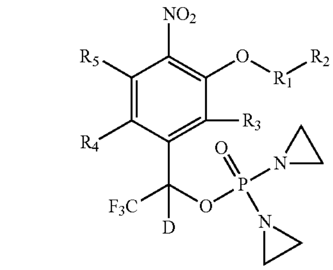
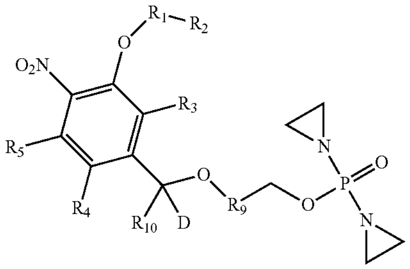
wherein the substituents are as defined in claim 1.
8. The solid compound according to claim 1, wherein the compound is selected from the following compounds:
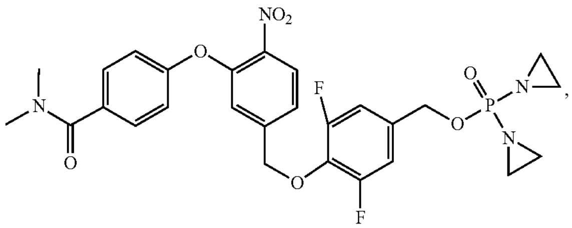
,
-continued
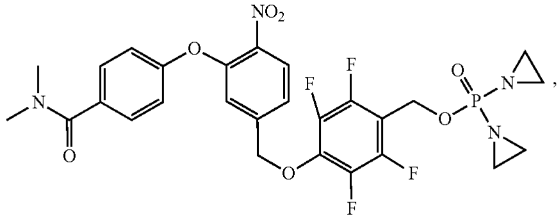
,
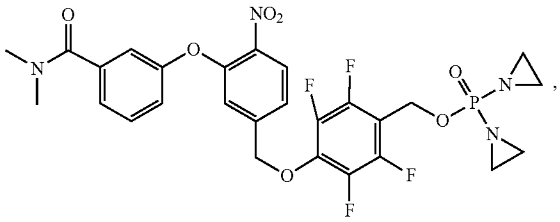
,
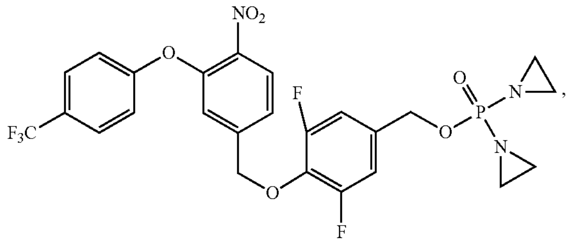
,
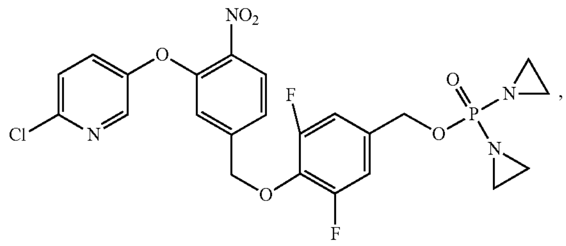
,
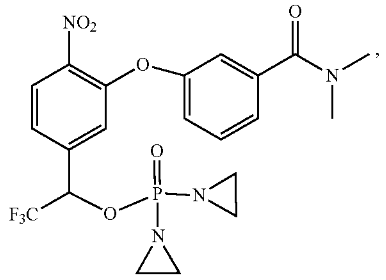
,
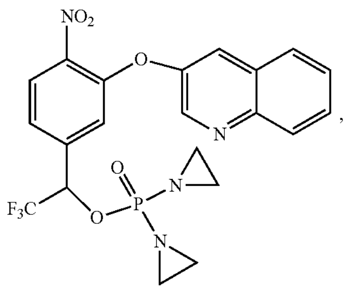
, -continued
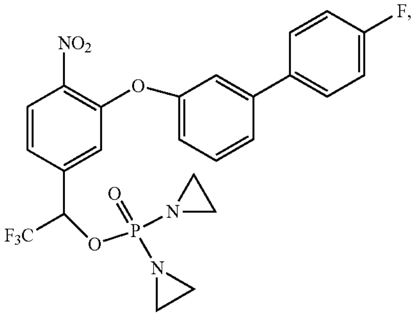
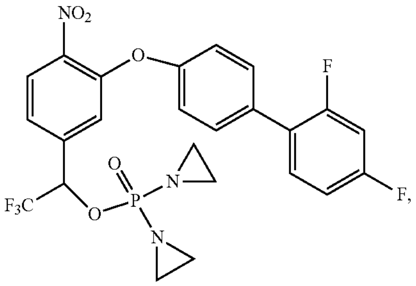
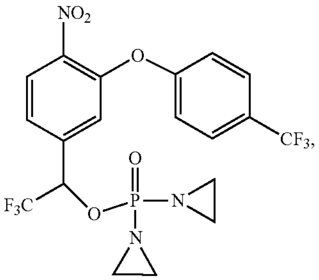
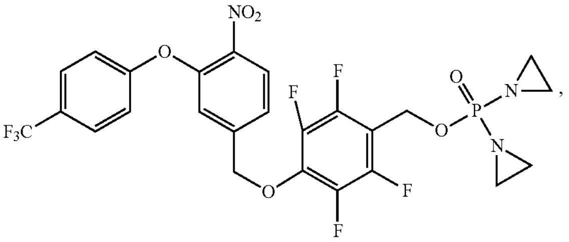
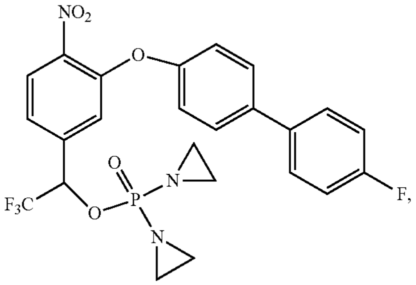
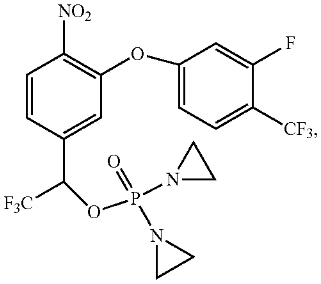
-continued
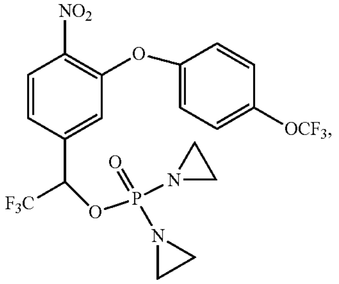
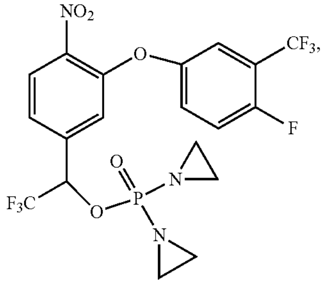
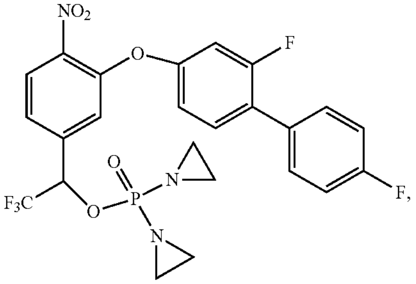
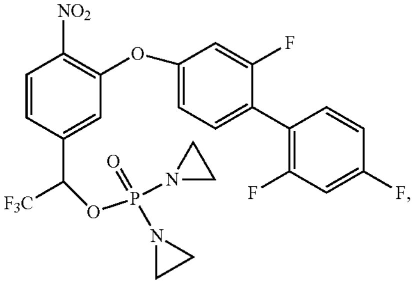
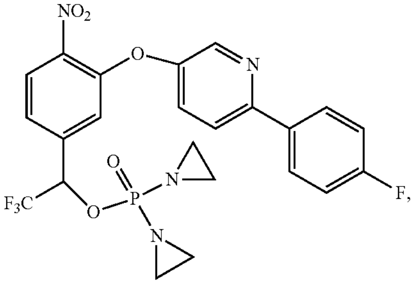
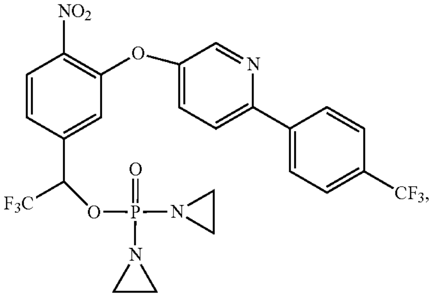

-continued
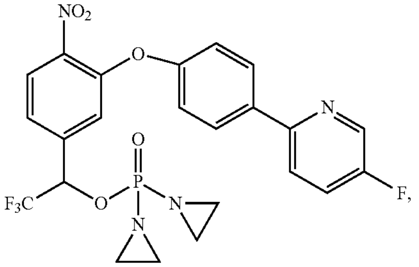
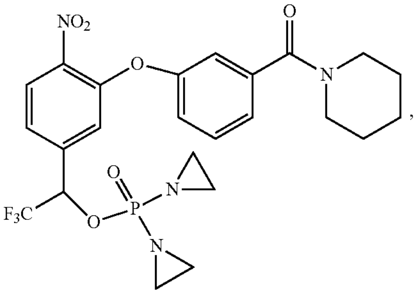
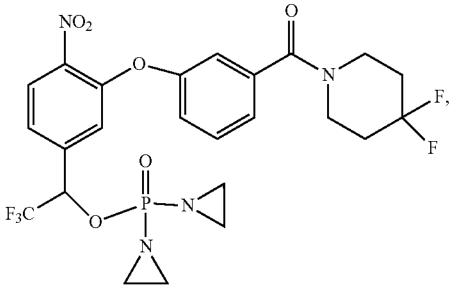
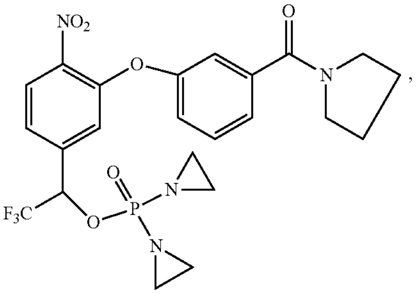
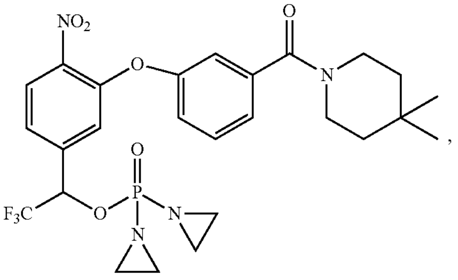
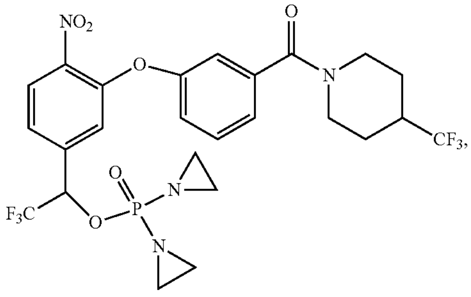
-continued
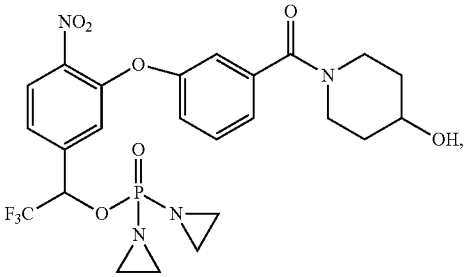
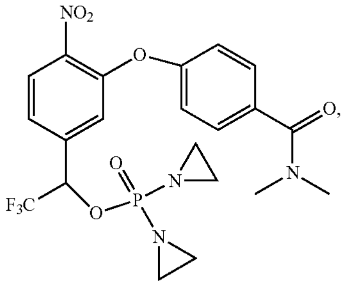
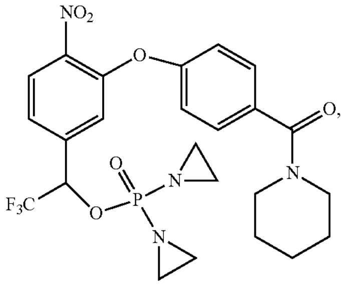
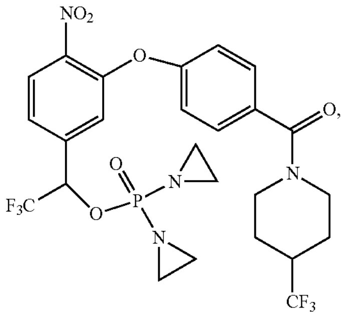
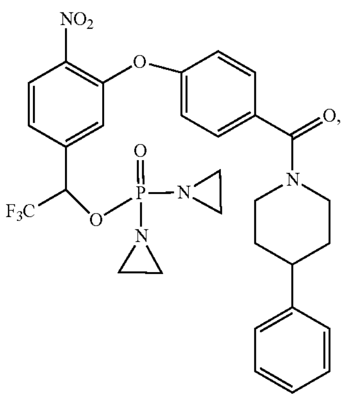

-continued

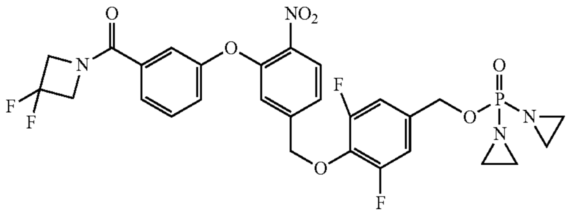

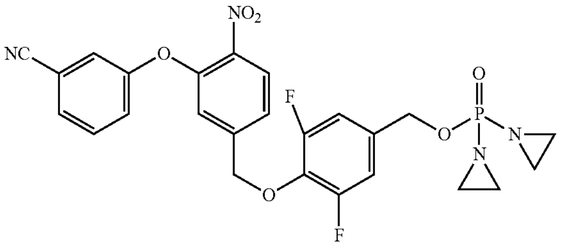

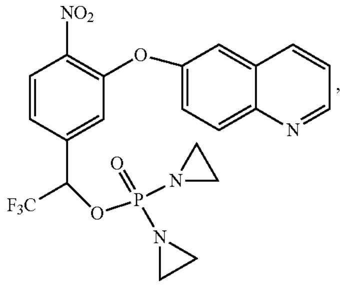

,

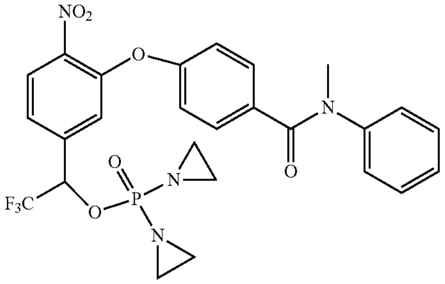

,

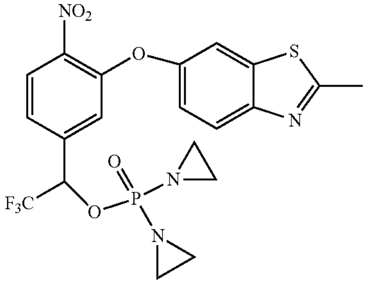

,

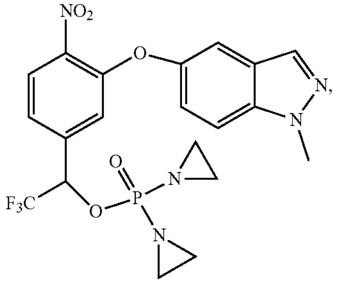

,

-continued

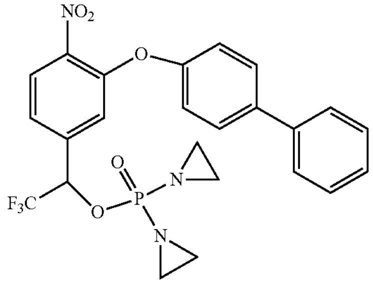

,

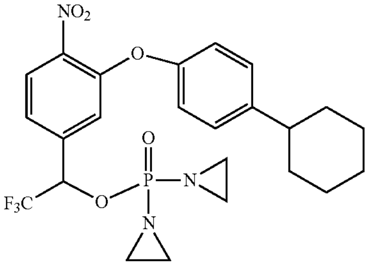

and

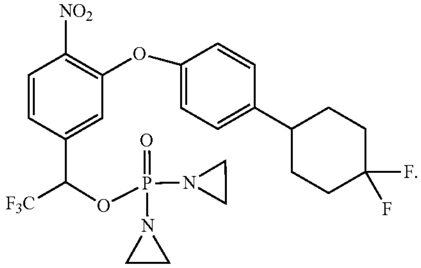

.

9. The solid compound according to claim 1, wherein the salt is a basic salt or an acid salt or the solvate is a hydrate or an alcoholate.

10. A medicament or formulation containing the solid compound according to claim 1.

11. A method of treating non-small cell lune cancer in a patient, the method comprising administering to the patient In need thereof the medicament or formulation according to claim 10.

12. A method for preparing the solid compound according to claim 1, characterized in that compounds V and VI are subjected to condensation reaction to close rings to provide the compounds of above formulae II and III:

V

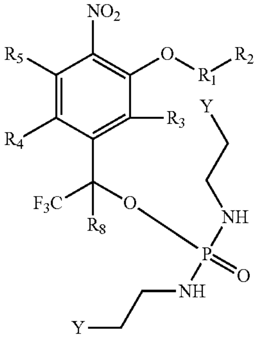

-continued

VI

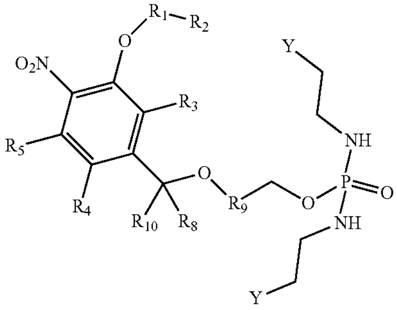

wherein Y is a leaving group, and the remaining variables are as defined in claim 1.

13. The method according to claim 12, wherein Y is Cl, Br, I, —OTs, —$ONO_2$, —OLCMS or —OTf, and in the condensation reaction, organic amines are used as acid-binding agents.

14. The method according to claim 13, wherein Y is Br, and in the condensation reaction, N,N-diisopropylethylamine (DIPEA) is used as the acid-binding agent, and silver oxide ($Ag_2O$) is used as the catalyst.

15. A method for preparing the solid compound according to claim 1, characterized by making

VII

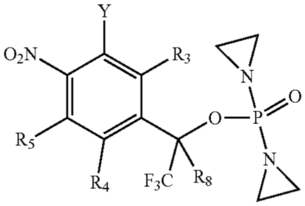

VIII

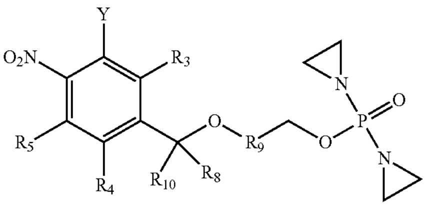

VII react with $R_2R_1OH$ to give II, and making VIII react with $R_2R_1OH$ to give III, or making IX and X

IX

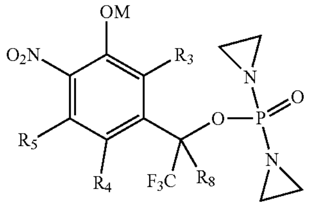

X

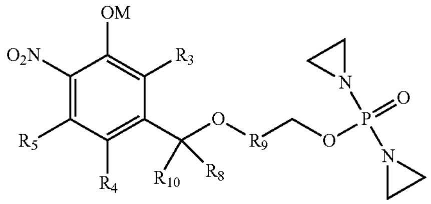

react with $YR_1R_2$ to obtain II and III, wherein Y is a leaving group, M is H or an alkali metal, and the remaining substituents are as defined in claim 1.

16. A method for preparing the compound according to claim 15, wherein Y is F, Cl, Br, I, —OTs, —$ONO_2$, —OLCMS or —OTf.

17. A solid compound having the following formula:

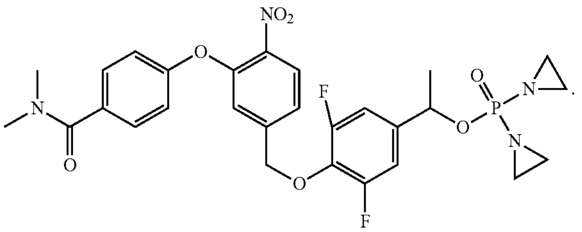 [SMILES: CC(OP(=O)(N1CC1)N1CC1)c1cc(F)c(OCc2ccc([N+](=O)[O-])c(Oc3ccc(C(=O)N(C)C)cc3)c2)c(F)c1]

* * * * *